United States Patent
Laleg et al.

(10) Patent No.: US 11,344,847 B2
(45) Date of Patent: May 31, 2022

(54) CONTROL OF DISTRIBUTED HEAT TRANSFER MECHANISMS IN MEMBRANE DISTILLATION PLANTS

(71) Applicant: King Abdullah University of Science and Technology, Thuwal (SA)

(72) Inventors: Taous Meriem Laleg, Thuwal (SA); Fadi Eleiwi, Thuwal (SA); Ayman Karam, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 667 days.

(21) Appl. No.: 15/741,468

(22) PCT Filed: Jun. 30, 2016

(86) PCT No.: PCT/IB2016/053946
§ 371 (c)(1),
(2) Date: Jan. 2, 2018

(87) PCT Pub. No.: WO2017/002077
PCT Pub. Date: Jan. 5, 2017

(65) Prior Publication Data
US 2018/0361320 A1     Dec. 20, 2018

Related U.S. Application Data

(60) Provisional application No. 62/187,618, filed on Jul. 1, 2015.

(51) Int. Cl.
*B01D 61/36*     (2006.01)
*G05B 13/04*     (2006.01)
(Continued)

(52) U.S. Cl.
CPC ......... *B01D 61/364* (2013.01); *B01D 61/366* (2013.01); *C02F 1/008* (2013.01);
(Continued)

(58) Field of Classification Search
CPC ............... B01D 61/364; B01D 61/366; B01D 2311/10; B01D 2311/06; B01D 2311/04;
(Continued)

(56) References Cited

U.S. PATENT DOCUMENTS 3,302,701 A * 2/1967 Thomas ................ F28F 13/06
165/109.1
3,419,144 A * 12/1968 Huntington ............ B01D 63/16
210/637

(Continued)

OTHER PUBLICATIONS

V.M. Castillo and Wm. G. Hoover, "Entropy production Lyapunov instability at the onset of turbulent convection", Dec. 1998, The American Physical Society, vol. 58, No. 6, pp. 7350-7354. (Year: 1998).*

(Continued)

*Primary Examiner* — Joseph W Drodge
(74) *Attorney, Agent, or Firm* — Patent Portfolio Builders PLLC

(57) ABSTRACT

Various examples are provided that are related to boundary control in membrane distillation (MD) processes. In one example, a system includes a membrane distillation (MD) process comprising a feed side and a permeate side separated by a membrane boundary layer; and processing circuitry configured to control a water production rate of the MD process based at least in part upon a distributed heat transfer across the membrane boundary layer. In another example, a method includes determining a plurality of estimated temperature states of a membrane boundary layer separating a feed side and a permeate side of a membrane distillation (MD) process; and adjusting inlet flow rate or (Continued)

inlet temperature of at least one of the feed side or the permeate side to maintain a difference temperature along the membrane boundary layer about a defined reference temperature based at least in part upon the plurality of estimated temperature states.

17 Claims, 26 Drawing Sheets

(51) Int. Cl.
| | |
|---|---|
| G05B 17/02 | (2006.01) |
| G16C 99/00 | (2019.01) |
| G06F 17/13 | (2006.01) |
| C02F 1/44 | (2006.01) |
| C02F 1/00 | (2006.01) |

(52) U.S. Cl.
CPC ............ *C02F 1/447* (2013.01); *G05B 13/045* (2013.01); *G05B 17/02* (2013.01); *B01D 2311/04* (2013.01); *B01D 2311/06* (2013.01); *B01D 2311/10* (2013.01); *B01D 2311/16* (2013.01); *G06F 17/13* (2013.01); *G16C 99/00* (2019.02)

(58) Field of Classification Search
CPC .. B01D 2311/16; B01D 65/10; B01D 61/368; B01D 2325/021; B01D 2313/345; B01D 61/10; B01D 61/12; B01D 61/20; B01D 61/22; B01D 61/36; B01D 65/08; B01D 2313/65; B01D 61/32; G05B 17/02; G05B 13/045; G16C 99/00; G06F 17/13; G01N 17/008; Y02A 20/131; C02F 1/447; C02F 2103/08; C02F 2209/005; C02F 2209/02; C02F 2209/006; C02F 2209/03; C02F 2209/40; C02F 1/008; Y02W 10/37
USPC ... 210/640, 649, 650, 739, 741, 742, 85, 87, 210/90, 96.2, 143, 149; 203/1, 2
See application file for complete search history.

(56) References Cited

U.S. PATENT DOCUMENTS

| | | | | | |
|---|---|---|---|---|---|
| 4,781,837 | A | * | 11/1988 | Lefebvre | A23C 9/1427 210/640 |
| 5,217,581 | A | * | 6/1993 | Ewing | B01D 1/0082 203/1 |
| 6,365,051 | B1 | * | 4/2002 | Bader | B01D 61/147 210/640 |
| 6,396,285 | B1 | * | 5/2002 | Blackham | G01R 27/32 324/601 |
| 9,568,258 | B1 | * | 2/2017 | Colas | F28F 13/00 |
| 2004/0104171 | A1 | * | 6/2004 | Zeiher | B01D 61/12 210/652 |
| 2004/0144112 | A1 | * | 7/2004 | He | G05B 11/42 62/225 |
| 2006/0184254 | A1 | * | 8/2006 | Carpency | F25J 3/0219 700/30 |
| 2009/0114594 | A1 | * | 5/2009 | Sirkar | B01D 61/38 210/640 |
| 2009/0150088 | A1 | * | 6/2009 | Seo | E02B 1/02 702/25 |
| 2009/0204234 | A1 | * | 8/2009 | Sustaeta | G05B 13/024 700/29 |
| 2009/0294122 | A1 | * | 12/2009 | Hansen | E21B 43/00 166/250.01 |
| 2010/0044310 | A1 | * | 2/2010 | Wan | B01D 61/145 210/637 |
| 2010/0170776 | A1 | * | 7/2010 | Ehrenberg | B01D 61/364 202/168 |
| 2011/0031100 | A1 | * | 2/2011 | Qtaishat | B01D 61/364 202/205 |
| 2013/0213885 | A1 | * | 8/2013 | Duan | B01D 61/002 210/636 |
| 2013/0240434 | A1 | * | 9/2013 | Yaeger | B01D 63/10 210/321.77 |
| 2014/0076728 | A1 | * | 3/2014 | Prakash | C02F 1/44 204/518 |
| 2015/0276209 | A1 | * | 10/2015 | Barenbrugge | F22B 35/104 122/449 |
| 2016/0107121 | A1 | * | 4/2016 | Lienhard | B01D 69/02 210/640 |
| 2018/0297867 | A1 | * | 10/2018 | Fleckner | C02F 1/008 |

OTHER PUBLICATIONS

Abdelkader Mojtabi and Michel Deville, "One-dimensional linear advection-diffusion equation: Analytical and finite element solutions ", Mar. 2015, Computers and Fluids, vol. 107, pp. 189-195. (Year: 2015).*

Notification of Transmittal of the International Search Report and the Written Opinion of the International Searching Authority, or the Declaration for PCT/IB2016/053946 dated Sep. 29, 2016.

Ashoor, et al., "Principles and applications of direct contact membrane distillation(DCMD): A comprehensive review", Desalination, vol. 398, ISSN: 0011-9164, DOI: 10.1016/J.Desal.2016.7.043 Section 2.2.3 Two-dimensional dynamic model, Aug. 3, 16, 222-246.

Dubrovnik, et al., "International Conference on Numerical and Mathematical Modeling of Flow and Transport in Porous Media Book of Abstracts", retrieved from the Internet: URL:http://nm2porousmedia.math.pmf.unizg.hr/NM2PorousMedia-2014-Book-Abstracts.pdf#page=62 [retrieved on Sep. 19, 2016]the whole document, Oct. 3, 2014.

Fadi, et al., "Dynamic modeling and experimental validation for direct contact membrane distillation(DCMD) process", Desalination 384, 2016, 1-11.

Fadi, et al., "Dynamic modeling and optimization of membrane distillation system", Proceedings of the 17th World Congress the International Federation of Automatic Control, Seoul, Korea, vol. 47, No. 3, Jan. 1, 2014, 3327-3332.

Fadi, et al., "Membrane Distillation Process Modeling: Dynamical Approach, International Journal of Chemical Molecular, Nuclear, Materials and Metallurgical Engineering, vol. 8, No. 6", Jan. 1, 2014, 516-521.

Fadi, et al., "Nonlinear Lyapunov-based boundary control of distributed heat transfer mechanisms in membrane distillation plant", 2015 American Control Conference (ACC),, Jul. 1, 2015, 4964-4969.

Hitsov, et al., "Modelling approaches in membrane distillation: A critical review,", Separation and Purification Technology, vol. 142,, Dec. 31, 2014, 48-64.

Shirazi, et al., "Computational Fluid Dynamc (CFD) opportunities applied to the membrane distillation process State-of-the-art and perspectives", Desalination, vol. 377,, Sep. 19, 2015, 73-90.

Communication pursuant to Article 94(3) EPC in corresponding/related EP Application No. 16735942.1, dated Jun. 26, 2019 (References D1 and D2 were cited in the IDS filed Jan. 2, 2018).

First Examination Report in corresponding/related GCC Application No. GC 2016-31647, dated Apr. 9, 2019 Documents D1, D2 and D2 were cited in the IDS filed Jan. 2, 2018).

Second Examination Report in corresponding/related GCC Application No. GC 2016-31647, dated Aug. 25, 2019 Documents D1, D2 and D2 were cited in the IDS filed Jan. 2, 2018).

* cited by examiner

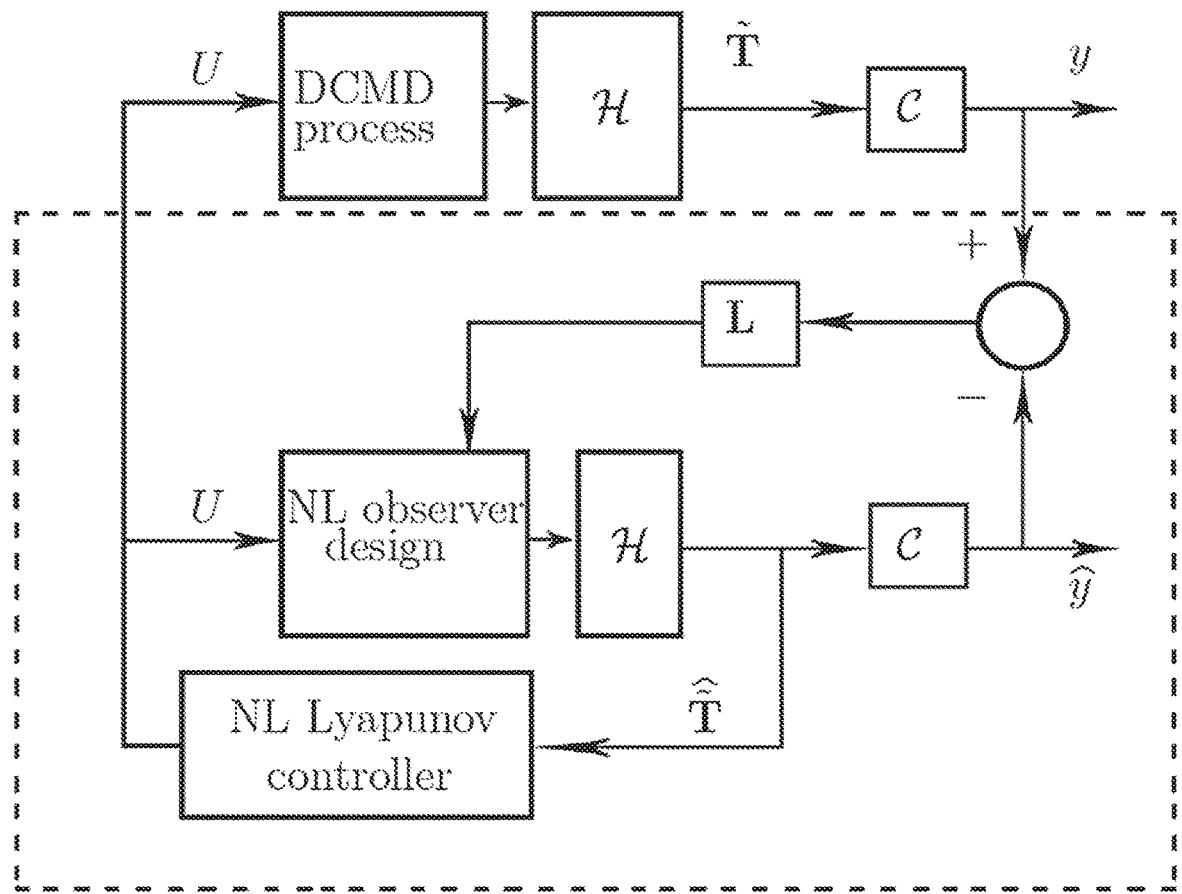

FIG. 5

MEMBRANE DISTILLATION PROCESS PARAMETERS

| Symbol | Parameter | Value |
|---|---|---|
| $v_z$ (or $v_z$) | Flow rate | 0.25 m/s |
| $v_x$ (or $v_x$) | Flow rate | 0.025 m/s |
| $C$ | Mass Transfer Coefficient | 0.0019 $Kg/h.Pa.m^2$ |
| $\delta_m$ | Thickness | $170 \pm 3 \ \mu m$ |
| $r$ | Mean flow pore size | $0.26 \ \mu m$ |
| $\epsilon$ | Porosity | $73 \pm 4$ |
| $LEP$ | Liquid Entry Pressure | 15 ($PSI$) |
| $k_f$ | Conductivity feed | 61,400 ($\mu s/cm$) |
| $k_p$ | Conductivity permeate | 8.5 ($\mu s/cm$) |

FIG. 6

Characteristics of the membrane.

| Parameter | Value |
|---|---|
| Membrane type | PTFE |
| Liquid Entry Pressure ($PSI$) | 15 |
| Thickness ($\mu m$) | 170 ±3 |
| Tortuosity | 1.35 |
| Mean flow pore size ($\mu m$) | 0.26 |
| First bubble point ($\mu m$) | 0.42 |
| Porosity (%) | 73 ±4 |
| Contact angle | 140° ± 3° |
| Mass Transfer Coefficient ($Kg/h.Pa.m^2$) | 0.001 |

FIG. 13A

Characteristics of the feed water (Redseawater).

| Parameter | Feed water (Redseawater) |
|---|---|
| pH | 8.03 |
| Conductivity ($\mu S/cm$) | 61,400 |
| Turbidity ($NTU$) | 0.96 |
| TOC ($mg/L$) | 1.94 |
| Calcuim ($mg/L$) | 480.5 |
| Magnesium ($mg/L$) | 1530 |
| Sodium ($mg/L$) | 12,628 |
| Boron ($mg/L$) | 5.1 |
| Potassium ($mg/L$) | 425 |
| Chloride ($mg/L$) | 23,128 |
| Sulfate ($mg/L$) | 2650 |

FIG. 13B

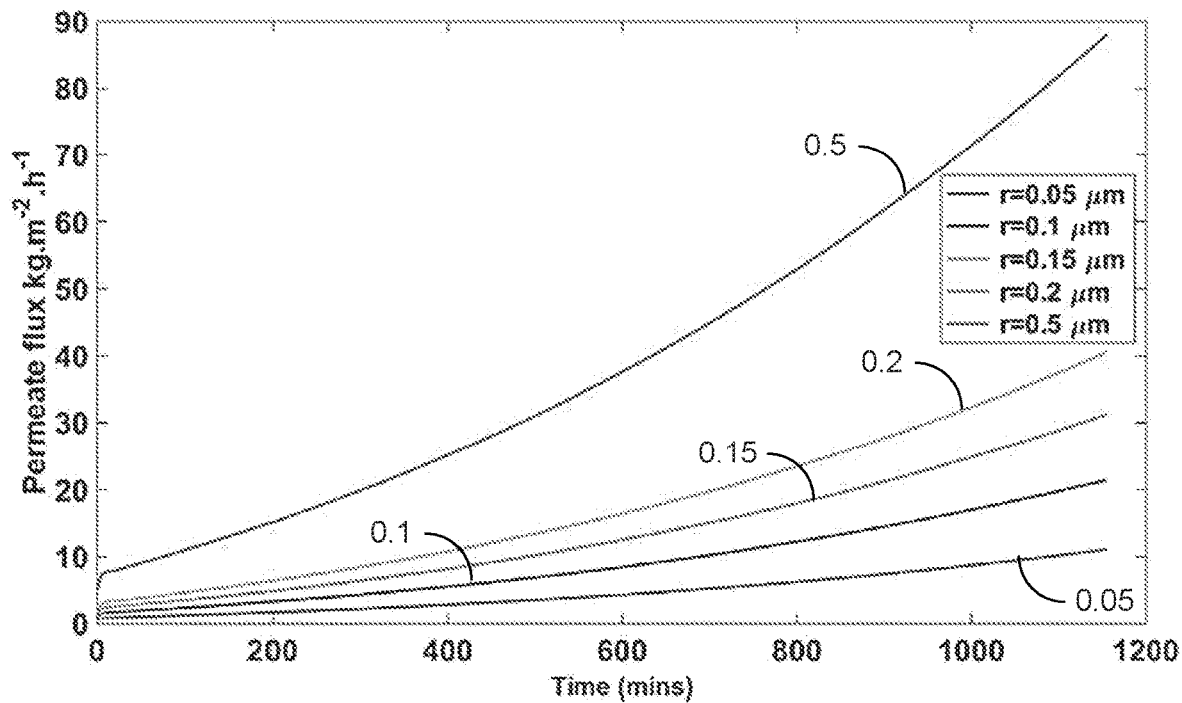

FIG. 14C

| Parameter | Value |
| --- | --- |
| Seawater thermal conductivity | $0.596\ W/m.K$ |
| Freshwater thermal conductivity | $0.607\ W/m.K$ |
| Flow rate of freshwater | $0.2\ m/s$ |
| Specific heat of freshwater | $3850\ J/kg.C$ |
| Specific heat of seawater | $4180\ J/kg.C$ |

| Parameter | Value |
| --- | --- |
| Seawater density | $1035\ kg/m^3$ |
| Freshwater density | $998.2\ kg/m^3$ |
| Flow rate of seawater | $0.25\ m/s$ |
| Molecular weight of water | $18.01489\ g/mol$ |
| Average thermal conductivity of membrane and vapor | $0.24\ W/mK$ |

FIG. 15

| Membrane material | PTFE (M1) |
|---|---|
| Liquid Entry Pressure (*PSI*) | 15 |
| Thickness ($\mu m$) | 176 |
| Mean flow pore size ($\mu m$) | 0.24 |
| First bubble point ($\mu m$) | 0.42 |
| Porosity (%) | 70 |
| Contact angle | $140°\pm 3°$ |
| Mass Transfer Coefficient ($Kg/h.Pa.m^2$) | 0.001 |
| Feed inlet temperature (°C) | 60 |
| Permeate inlet temperature (°C) | 20 |

DCMD Module Parameters

| Property | Value |
|---|---|
| Membrane material | PTFE |
| Pore size | 0.27 $\mu m$ |
| Total thickness | 0.170 mm |
| Porosity | 77% |
| Active area | $0.06 m^2$ |
| Module length | 0.4 m |
| Module width | 0.15 m |

CONTROL OF DISTRIBUTED HEAT TRANSFER MECHANISMS IN MEMBRANE DISTILLATION PLANTS

CROSS REFERENCE TO RELATED APPLICATIONS

This application is a National Stage Application of PCT/IB2016/053946, filed on Jun. 30, 2016, which claims priority to, and the benefit of, provisional application entitled "NONLINEAR LYAPUNOV-BASED BOUNDARY CONTROL OF DISTRIBUTED HEAT TRANSFER MECHANISMS IN MEMBRANE DISTILLATION PLANTS" having Ser. No. 62/187,618, filed Jul. 1, 2015, which is hereby incorporated by reference in its entirety.

BACKGROUND

A membrane distillation (MD) process is thermal, and includes a transfer of water vapor from a feed container to a permeate container through a micro-porous membrane, and reject other non-volatile constituents present in the influent water. The process is driven by the temperature difference along the membrane boundary layers. This gives significance to the temperature distribution among the process domain and especially along the membrane boundary layers. However, the MD process has a serious drawback in the production rate stability, and its energy consumption.

SUMMARY

Embodiments of the present disclosure are related to control of membrane distillation (MD) processes.

In one embodiment, among others, a system comprises a membrane distillation (MD) process comprising a feed side and a permeate side separated by a membrane boundary layer; and processing circuitry configured to control a water production rate of the MD process based at least in part upon a distributed heat transfer across the membrane boundary layer. In one or more aspects of these embodiments, the processing circuitry can maintain a temperature difference along the membrane boundary layer at a level that promotes the water production rate of the MD process. Control of the water production rate can be based upon nonlinear Lyapunov-based boundary control of the temperature difference of membrane boundary layer, perturbation-based extremum seeking control (PESC) of the temperature difference of membrane boundary layer, or Newton-based multivariable extremum seeking control (ESC) of the temperature difference of membrane boundary layer. In one or more aspects of these embodiments, a semi-discretized model of the membrane boundary layer can be utilized. The processing circuitry can monitor inlet temperatures of the feed side and the permeate side to control the water production rate of the MD process. The inlet temperatures of the feed side and the permeate side can be bounded by a defined minimum temperature and a defined maximum temperature. The processing circuitry can monitor inlet flow rates of the feed side and the permeate side to control the water production rate of the MD process.

In another embodiment, a method comprises determining a plurality of estimated temperature states of a membrane boundary layer separating a feed side and a permeate side of a membrane distillation (MD) process; and adjusting inlet flow rate or inlet temperature of at least one of the feed side or the permeate side to maintain a difference temperature along the membrane boundary layer about a defined reference temperature based at least in part upon the plurality of estimated temperature states. In one or more aspects of these embodiments, control of a water production rate of the MD process can be based upon nonlinear Lyapunov-based boundary control of the difference temperature of membrane boundary layer, perturbation-based extremum seeking control (PESC) of the difference temperature of membrane boundary layer, or Newton-based multivariable extremum seeking control (ESC) of the difference temperature of membrane boundary layer. The difference temperature along the membrane boundary layer can be determined based upon temperature estimates generated by a non-linear observer. The method can comprise adjusting a combination of inlet flow rate and inlet temperature of the feed side or the permeate side to control the water production rate of the MD process.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 5 is a block diagram illustrating an example of the structure of a nonlinear observer-based Lyapunov controller in accordance with various embodiments of the present disclosure.

FIG. 6 is a table illustrating an example of MD process parameters in accordance with various embodiments of the present disclosure.

FIGS. 13A, 13B and 15 are tables indicating characteristics of the membrane and feed water used in the experimental set-up of FIG. 12 in accordance with various embodiments of the present disclosure.

FIGS. 14A-14C and 16A-16D illustrated experimental and modeled results of the MD process of FIG. 12 in accordance with various embodiments of the present disclosure.

DETAILED DESCRIPTION

Figure 1:
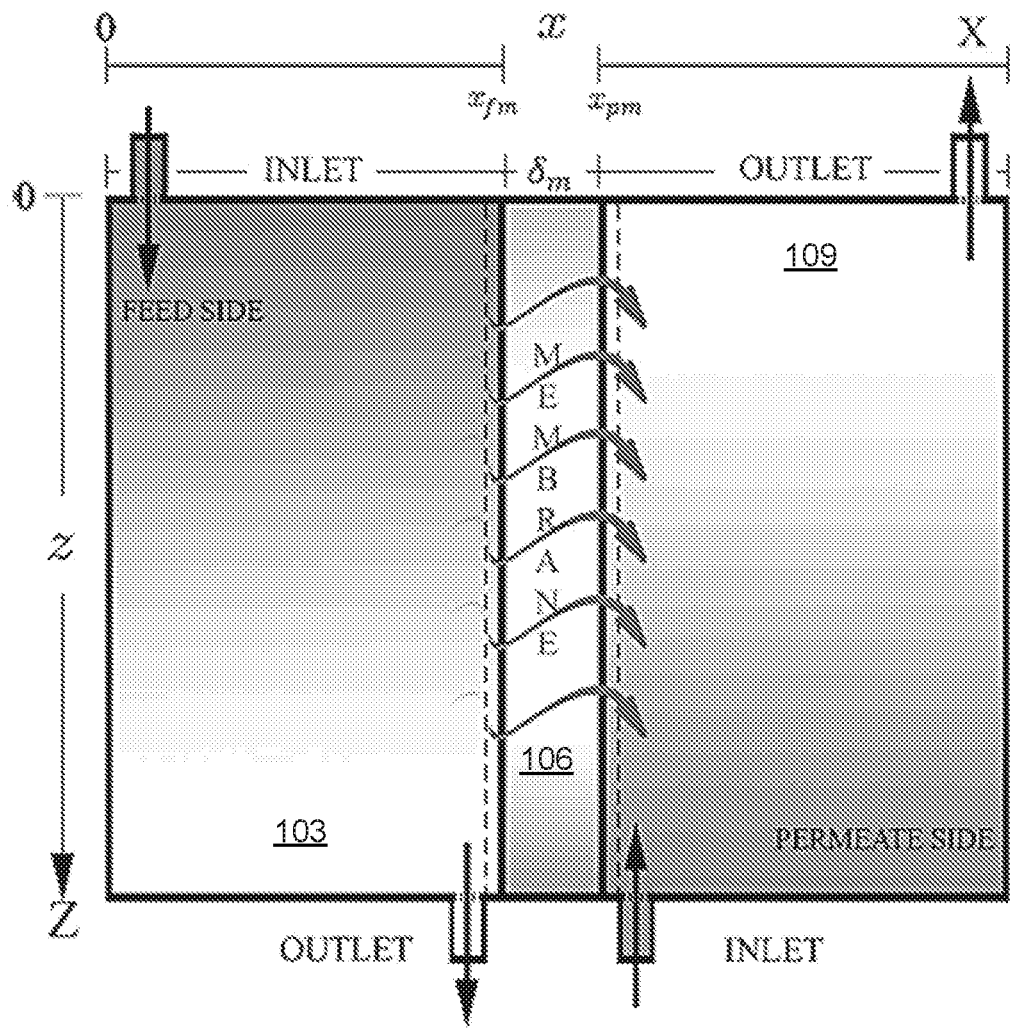
FIG. 1 is a schematic diagram depicting an example of a MD process in accordance with various embodiments of the present disclosure.

Disclosed herein are various embodiments related to boundary control in membrane distillation (MD) processes. Four common configurations include air-gap membrane distillation (AGMD), vacuum membrane distillation (VMD), sweeping-gas membrane distillation (SGMD), and direct-contact membrane distillation (DCMD). Control of MD processes can help with potential commercialization of MD systems, and take advantage of their interesting properties. For example, nonlinear Lyapunov-based boundary control can be applied to distributed heat transfer mechanisms in membrane distillation plants. Reference will now be made in detail to the description of the embodiments as illustrated in the drawings, wherein like reference numbers indicate like parts throughout the several views.

Boundary controls for the temperature difference of membrane distillation boundary layers are presented. The heat transfer mechanisms inside the MD process (e.g., DCMD) are modeled with a 2D advection diffusion equation (ADE). The model can be semi-discretized in space, and a nonlinear state-space representation can be provided. The control can be designed to force the temperature difference along the membrane sides to track a desired reference asymptotically, and hence a desired flux would be generated. Certain constraints can be put on the control law inputs to be within an economic range of energy supplies. The effect of the controller gain will be discussed. Simulations with real process parameters for the model, and the controller are provided.

To achieve the desired production rate for an MD plant, the temperature difference along the membrane boundary layer can be controlled, because of its driven role in the MD plant. The control strategies include considering both the feed and permeate inlet temperatures as control inputs leading to a boundary control. The heat transfer mechanisms that take place in the membrane distillation process can be modeled by a 2D advection diffusion equation. A Lyapunov-based boundary control for a nonlinear process, such as the MD, is presented. Controlling partial differential equations (PDE) models can be applied over the continuous model, a semi-discretized model, or a fully-discretized model. In this disclosure, a semi-discretized model is considered. The continuous PDE model is transformed from an infinite dimension system into a high dimension system of nonlinear ordinary differential equations (ODEs) given in the state-space representation. The advantages of adopting the semi-discretized model include that a good approximated model can be granted by refining the grid, and tuning the spatial step sizes. Furthermore, standard control strategies applicable for state-space representations can be extended to such systems.

Process Modeling

The dynamics of the heat transfer accompanied in the process of membrane distillation (MD) is modeled using the 2D advection diffusion equation (ADE). The convection mechanism can be assumed to be along the z-axis (membrane length), where the diffusion mechanism can be assumed to be along the x-axis (normal to the membrane). A further extension can be applied over the model, which can lead to better consistency and flexibility in manipulating the equation by an appropriate choice of the values of the flow rates and diffusion constants. In addition, the heat convection and heat diffusion can be extended along the x and z-coordinates, even if it is for a small amount.

Referring to FIG. 1, shown is a schematic diagram depicting an example of a MD process 100. The counter current MD process 100 includes a feed subsystem 103, a membrane 106, and a permeate subsystem 109. The MD process model considers the module of the membrane to be counter current for the hot and cold water streams. The heat transfer between the feed and the permeate subsystems 103 and 109 is driven by the transmembrane heat flux, and the latent heat of evaporation. Both of them are functions of the temperature difference between the membrane boundary layers of the feed and the permeate subsystems 103 and 109. This temperature difference makes the model nonlinear.

Mathematical Model.

The extended model of the MD process is general. Moreover, it is symmetric for the convection and the diffusion heat transfer mechanisms, which take place in the process domain. The model considers computing the time evolution of the temperature. In the system domain, temperature $T(x, z, t)$ is the variable of interest with feed inlet and permeate inlet as process inputs. The mathematical model for the heat transfer mechanisms in the MD process is illustrated in FIG. 1. A rectangular domain has final values for the time and the space coordinates as shown below. The model is based on the following 2D advection diffusion equation.

$$\frac{\partial T(x,z,t)}{\partial t} + v_z \frac{\partial T(x,z,t)}{\partial z} + v_x \frac{\partial T(x,z,t)}{\partial x} = \alpha_x \frac{\partial^2 T(x,z,t)}{\partial x^2} + \alpha_z \frac{\partial^2 T(x,z,t)}{\partial z^2}, \tag{1}$$

with $0<t<\tau_{final}$, $0<x<X$, $0<z<Z$, where $x\in[0,x_{fm}]$ is in the feed and $x\in[x_{pm}, X]$d is in the permeate. The terms $v_x$ and $v_z$ are the hot and the cold water stream flow rates along the x and z axes, respectively, which are assumed to be constant along the operation of the process. The terms $\alpha_x$ and $\alpha_z$ are constants that depend on physical properties of the used water:

$$\alpha = \frac{\kappa_e}{\rho c_p}, \tag{2}$$

where $\kappa_e$ is the thermal conductivity, $c_p$ is the specific heat, and $\rho$ is the density. The initial conditions can be set to be constant throughout the model domain as given by:

$$T_f(x,z,0)=T_{f_{initial}} \text{ for } x\in[0,x_{fm}], T_p(x,z,0)=T_{P_{initial}} \text{ for } x\in[x_{pm},X] \tag{3}$$

The associated boundary conditions with the model (e.g., feed solution) are assumed to be a Dirichlet condition for the inlet of each subsystem container as given by:

$$T(x,0,t)=T_{0_f} \text{ for } x\in[0,x_{f_m}], \tag{4}$$

$$T(x,z,t)=T_{0_p} \text{ for } x\in[x_{pm},X], \tag{5}$$

and Neumann conditions for the rest of the boundaries, such as: the process is isolated from the left side boundary of the feed side as given in:

$$\left.\frac{\partial T(x,z,t)}{\partial x}\right|_{x=0} = 0, \tag{6}$$

and the right boundary side for the permeate side as given in:

$$\left.\frac{\partial T(x,z,t)}{\partial x}\right|_{x=X} = 0, \tag{7}$$

and has a trans-membrane heat transfer formula for the heat flux and the latent heat of evaporation with the other subsystem (e.g. the permeate subsystem 109) such as given in:

$$\left.\frac{\partial T(x,y,t)}{\partial x}\right|_{x=x_{fm}} = \frac{\left[J(T)H(T) + \frac{k_m}{\delta_m}T(x_{fm},z,t) - \frac{k_m}{\delta_m}T(x_{pm},z,t)\right]}{k_f}, \tag{8}$$

for the feed side and as given in:

$$\left.\frac{\partial T(x,y,t)}{\partial x}\right|_{x=x_{pm}} = \frac{\left[J(T)H(T) + \frac{k_m}{\delta_m}T(x_{fm},z,t) - \frac{k_m}{\delta_m}T(x_{pm},z,t)\right]}{k_p}, \tag{9}$$

for the permeate side, and finally the process has a heat flux release at the bottom boundary for the feed side as given in:

$$\left.\frac{\partial T(x,z,t)}{\partial z}\right|_{z=Z} = \phi \tag{10}$$

and at the top boundary for the permeate side as given in:

$$\left.\frac{\partial T(x,z,t)}{\partial z}\right|_{z=0} = \phi. \tag{11}$$

The term $k_m$ is the average thermal conductivity of membrane, the term $\delta_m$ is the membrane thickness, $\phi\in\mathbb{R}^+$ is a positive constant that represents the amount of flux that is released outside the process domain (or containers). It may be considered to be zero in the simulations, $J(T)$ is the trans-membrane heat flux, and $H(T)$ is the latent heat of evaporation, which is responsible for the released sensible heat. The empirical formula for the latent heat of water is:

$$H(T)=2500.8-2.36T+0.0016T^2-0.00006T^3 J/g$$

The trans-membrane heat flux can be based on a Knudsen diffusion model for the mass transfer coefficient given by:

$$J(T) = 1.064 \frac{r\epsilon}{\chi\delta_m}\left(\frac{M}{RT_{mean}}\right)^{\frac{1}{2}}\Delta P(T)$$

where r is the membrane pore size, M is the molecular weight, R is the gas universal constant, $\chi$ is the membrane tortuosity, and ϵ is the membrane porosity. The term ΔP(T) is the vapor pressure gradient between the membrane sides, which is a function of the vapor temperature based on the Antoine equation. Both are nonlinear functions of the temperature distribution.

Semi-Discretized Model.

Figure 2:
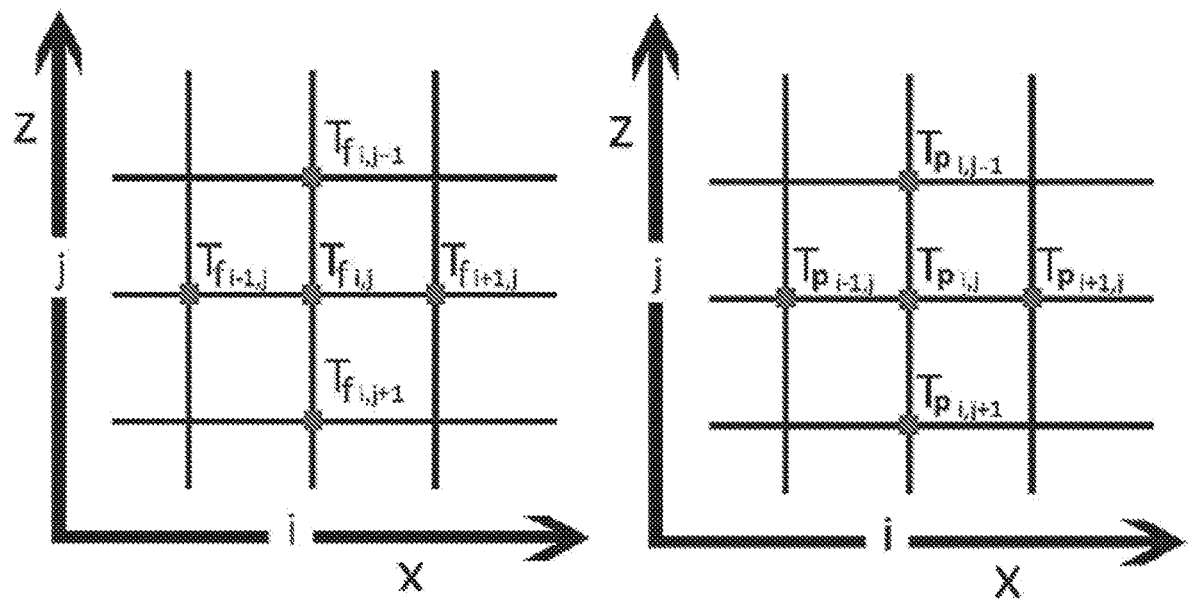
FIG. 2 is an example of discretization of a feed subsystem and a permeate subsystem of the MD process of FIG. 1 in accordance with various embodiments of the present disclosure.
Figure 3:
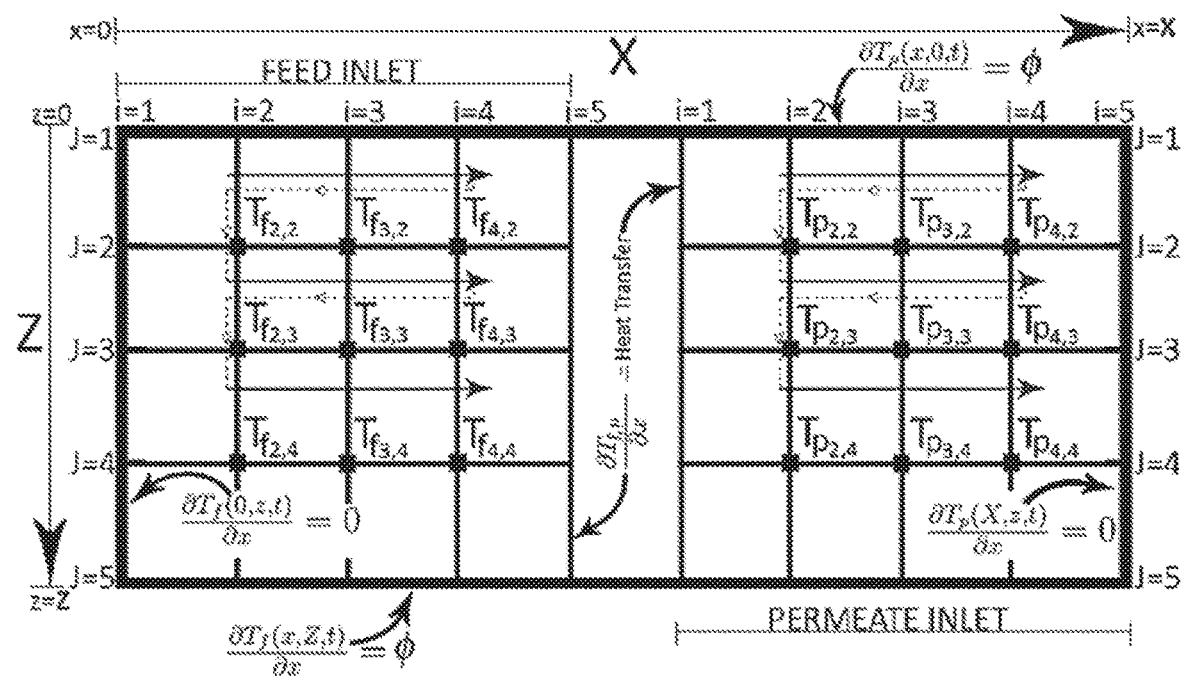
FIG. 3 is an example of a schematic diagram for the grid of discretization with boundary conditions including boundary conditions in accordance with various embodiments of the present disclosure.

The space discretization can be done using finite difference discretization schemes. Based on this, the PDE can be transformed from infinite dimensional problem into a finite dimensional group of ODEs. The convective and diffusive terms can be solved with a first-order upwind scheme and a central differencing scheme, respectively. The upwind scheme warrants the stability and ensures the solution to satisfy the entropy condition. The central difference scheme is suitable for second derivative diffusive terms. Referring to FIG. 2, shown is an example of the preparation of discretization for the feed subsystem 103 and the permeate subsystem 109 of FIG. 1. Each point in the grid 203 depends on itself and the surrounding four points as shown in FIG. 2. Distances between two consecutive points in the same row in the grid is equal to the horizontal axis step size $\Delta x$, where it is equal to $\Delta z$ between two points below each other in the vertical axis. A schematic diagram for the grid of discretization with boundary conditions is shown in FIG. 3. The discretization starts in a row-wise fashion solving for the temperature of the feed subsystem 103 (FIG. 1), then solving for the temperature of permeate subsystem 109 (FIG. 1). The difference between the boundary layer cells drives the trans-membrane heat flux and runs the MD process.

The discrete version of the continuous MD 2D advection diffusion equation (ADE) is a nonlinear high dimension system of ODEs. The discrete model is shown in:

$$\dot{\underline{T}}(x,z,t) = A\underline{T}(x,z,t) + B\underline{U}(t) + \underline{b}(T(x,z,t)), \quad (12)$$

where vector $\underline{T} \in \mathbb{R}^{2n^2 \times 1}$ is the state vector which represents the temperature distribution (at each grid point) inside the feed and the permeate domain ($\underline{T}_f, \underline{T}_p$) for the time evolution, such as in:

$$\underline{T} = \begin{bmatrix} T_f \\ T_p \end{bmatrix}, \quad (13)$$

thus $\underline{T}_f, \underline{T}_p \in \mathbb{R}^{n^2 \times 1}$ with n the number of discretization points in x and z. Matrix $A \in \mathbb{R}^{2n^2 \times 2n^2}$ represents the operator matrix that has the dynamics of the feed and the permeate subsystems 103 and 109 with their couplings on the boundaries as shown by:

$$A = \begin{bmatrix} A_{f_{i,j}} & C_{fp} \\ C_{pf} & A_{p_{i,j}} \end{bmatrix} \quad (14)$$

where $A_f \in \mathbb{R}^{n^2 \times n^2}$, $A_p \in \mathbb{R}^{n^2 \times n^2}$, $C_{fp} \in \mathbb{R}^{n^2 \times n^2}$, and $C_{pf} \in \mathbb{R}^{n^2 \times n^2}$, are given in:

$$A_{f_{i,j}} = \left(-\frac{v_z}{\Delta z} - \frac{v_x}{\Delta x} - \frac{2\alpha_x}{\Delta x^2} - \frac{2\alpha_z}{\Delta z^2}\right)T_{i,j} + \left(\frac{v_z}{\Delta z} + \frac{\alpha_z}{\Delta z^2}\right)T_{i,j-1} + \left(\frac{v_x}{\Delta x} + \frac{\alpha_x}{\Delta x^2}\right)T_{i-1,j} + \left(\frac{\alpha_z}{\Delta z^2}\right)T_{i,j+1} + \left(\frac{\alpha_x}{\Delta x^2}\right)T_{i+1,j}, \quad (15)$$

$$A_{p_{i,j}} = \left(\frac{v_z}{\Delta z} + \frac{v_x}{\Delta x} - \frac{2\alpha_x}{\Delta x^2} - \frac{2\alpha_z}{\Delta z^2}\right)T_{i,j} + \left(-\frac{v_z}{\Delta z} + \frac{\alpha_z}{\Delta z^2}\right)T_{i,j-1} + \left(\frac{\alpha_x}{\Delta x^2}\right)T_{i-1,j} + \left(\frac{\alpha_z}{\Delta z^2}\right)T_{i,j+1} + \left(-\frac{v_x}{\Delta x} + \frac{\alpha_x}{\Delta x^2}\right)T_{i+1,j}, \quad (16)$$

$$C_l = \frac{\alpha_x}{\Delta x^2} \frac{\Delta x k_m}{\delta_m k_l}, \quad l = f, p. \quad (17)$$

The terms $k_f$ and $k_p$ are the thermal conductivity constant of seawater and the fresh water, respectively, the term $\delta_m$ is the membrane thickness, and term $k_m$ is the average thermal conductivity of membrane and vapor.

Matrix $B \in \mathbb{R}^{2n^2 \times 2}$ is the input matrix as shown in:

$$B = \begin{bmatrix} \left(\frac{v_z}{\Delta z} + \frac{\alpha_z}{\Delta z^2}\right)_1 & 0 \\ \vdots & \vdots \\ \left(\frac{v_z}{\Delta z} + \frac{\alpha_z}{\Delta z^2}\right)_n & 0 \\ 0 & 0 \\ \vdots & \vdots \\ 0 & 0 \\ 0 & \left(-\frac{v_z}{\Delta z} + \frac{\alpha_z}{\Delta z^2}\right)_1 \\ 0 & \vdots \\ 0 & \left(-\frac{v_z}{\Delta z} + \frac{\alpha_z}{\Delta z^2}\right)_n \end{bmatrix}, \quad (18)$$

U(t) is the input vector that contains feed and permeate temperature inlets as given in:

$$\underline{U} = \begin{bmatrix} T_{IN_f} \\ T_{IN_p} \end{bmatrix}. \quad (19)$$

Vector $\underline{b}(T) \in \mathbb{R}^{2n^2 \times 1}$ contains the boundary conditions associated with the membrane boundary layer cells for the feed and the permeate subsystems 103 and 109, such that the trans-membrane heat flux and the latent heat of evaporation. Both of them are functions of the membrane boundary layers temperature difference, such as in:

$$\underline{b} = \begin{bmatrix} \zeta_1 \\ \vdots \\ \zeta_n \\ \eta_1 \\ \vdots \\ \eta_n \end{bmatrix}. \quad (20)$$

Vectors $\underline{\zeta}$ and $\underline{\eta}$ in $$\underline{\zeta} = \begin{bmatrix} 0 \\ \vdots \\ 0 \\ \frac{\alpha_x}{\Delta x} \frac{J(T)H(T)}{k_f} \end{bmatrix} \text{ and} \quad (21)$$

$$\underline{\eta} = \begin{bmatrix} -\frac{\alpha_x}{\Delta x} \frac{J(T)H(T)}{k_p} \\ 0 \\ \vdots \\ 0 \end{bmatrix} \quad (22)$$

represent the polynomial nonlinearity structures in the boundary vector. The measured output can be given by $y=C\underline{T}$ with an output matrix of $C=[0 \ldots 0\ 1\ 1\ 0 \ldots 0]\in\mathbb{R}^{1\times 2n^2}$.

Nonlinearity Analysis.

The MD dynamic model is nonlinear, and is originated from the functions $J(T)$ and $H(T)$. However, the present nonlinearity is Lipshitz continuous, and can be proved by examining each function separately. Consequently, $H(T)$ is Lipshitz continuous following the fact that it is a smooth and infinitely differentiable polynomial function. In the other hand, $J(T)$ can be defined as:

$$J(T) = c_1\left(\frac{1}{T}\right)^{\frac{1}{2}} 10^{\frac{-c_2}{T}},$$

where $c_1$, $c_2$ are constants, and $T\in[a, b]$, $b>a>0$. Therefore, $J(T)$ is continuous and differentiable on this interval $[a, b]$, and bounded $\|J(T)\|\leq \mathbb{M}$. As a result, there exists a Lipshitz constant $\lambda$ that satisfies $\|f(T_1)-f(T_2)\|\leq\lambda\|T_1-T_2\|$ and the nonlinearity in the MD dynamic model is Lipshitz continuous.

Controller Design

Nonlinear systems are challenging in terms of stability and control, due to their highly individualistic nature, and high sensitivity to initial and forcing conditions. The operation of heat transfer, inside the MD module, utilizes a sufficient temperature difference along the membrane boundary layers length. This boundary temperature difference is the driving force for the operation, and it causes the heat flux to be transferred from the feed subsystem 103 to the permeate subsystem 109 across the membrane 106 of FIG. 1.

The MD process could be efficient, if the production rate of the clean water is maintained almost constant with relative low energy consumption. This can be done if a controller keeps the temperature difference of the membrane boundary layer within an effective specific range, and the inputs within economic energy supplies.

A Lyapunov-based boundary controller can be used, in order to control the boundary layers temperature differences through the inlet temperatures (and/or the inlet flow rates) for each feed and permeate subsystems 103 and 109. Satisfying the stability conditions of the Lyapunov function guarantees boundedness of trajectories, and hereby the asymptotic convergence of the states. The control law can be limited within a sufficient temperature range for heat flux production, at the same time an economic range is limited for the energy consumption. For such criteria the temperature of both feed and permeate inlets should not fall below 20° C. ($\underline{U}_{min}$) and not to exceed 60° C. ($\underline{U}_{max}$), as shown in:

$$0<\underline{U}_{min}<\underline{U}(t)<\underline{U}_{max}, \forall t>0. \quad (23)$$

The MD model can be rewritten to be affine system as given in:

$$\begin{cases} \underline{\dot{T}} = f(\underline{T}) + B\underline{U}(t), \\ y = C\underline{T}. \end{cases} \quad (24)$$

Hence $f(\underline{T})$ is:

$$f(\underline{T})=A\underline{T}+\underline{b}(\underline{T}). \quad (25)$$

The output of the model $y\in\mathbb{R}^{n\times 1}$ is a linear combination of the difference for the boundary layer temperatures through the output matrix C, where $C\in\mathbb{R}^{n\times 2n^2}$ as given in:

$$C = \begin{bmatrix} 0 & \ldots & 1 & 0 & -1 & \ldots & 0 & \ldots & 0 \\ 0 & \ldots & 0 & 1 & \ldots & -1 & 0 & \ldots & 0 \\ 0 & \ldots & 0 & 0 & \ddots & 0 & \ddots & 0 & 0 \\ 0 & \ldots & 0 & \ldots & 0 & 1 & \ldots & -1 & 0 \end{bmatrix}. \quad (26)$$

Proposition 1: Assume that the temperature difference of the boundary layers obey equations (24) and (25). If the following control input is used:

$$\underline{U}=(CB)^{-1}(-CA\underline{T}-C\underline{b}(T)-k(C\underline{T}-\underline{y}_r)). \quad (27)$$

where $k\in\mathbb{R}^+$, then the closed loop system exhibits asymptotic reference tracking;

$$\lim_{t\to+\infty} \|\underline{e}(t)\| = 0. \quad (28)$$

where the difference between the output of the model y and the desired reference $y_r$, is defined as the reference tracking error, such as given in:

$$\underline{e}(t)=\underline{y}(t)-\underline{y}_r(t). \quad (29)$$

When the reference tracking error is asymptotic stable, the convergence of the states to their equilibrium set can be guaranteed, and so the output should track the desired reference. The analysis of the stability for the reference tracking error function is utilized by the following Lyapunov function:

$$V: R^n \to \mathbb{R}, \quad (30)$$

$$V(t) = \frac{1}{2}\underline{e}(t)^T\underline{e}(t), \quad (31)$$

for which the derivative is expressed by:

$$\begin{aligned} \dot{V}(t) &= \underline{e}(t)^T\underline{\dot{e}}(t) \\ &= (C\underline{T} - \underline{y}_r)^T(C\underline{\dot{T}} - \underline{\dot{y}}_r) \\ &= \underline{e}(t)^T C(f(t) + B\underline{U}(t)) \end{aligned} \quad (32)$$

In the design stage of the Lyapunov-based boundary controller, the derivative of the Lyapunov function in equation (32) should be negative definite for global stability. The derivative of the Lyapunov function is imposed to be equal a negative value, such as given in:

$$\dot{V}(t)=-k\underline{e}^Te, \quad (33)$$

where $k\in\mathbb{R}^+$ is a positive scalar controller gain. Hence, $$\underline{e}(t)^T(CA\underline{T}+C\underline{b}(T)+CB)=-k\underline{e}(t)^T\underline{e}(t). \quad (34)$$

After, an adequate control law input $\underline{U}(t)$ is selected to satisfy (34) such that the control law is defined as:

$$\underline{U}=(CB)^{-1}(-CA\underline{T}-C\underline{b}(T)-k(C\underline{T}-\underline{y}_r)), \quad (35)$$

where applying this control law in equation (35) to equation (34) achieves the asymptotic stability for the predefined reference tracking error, and track the desired reference. Hereby, the derivative of the Lyapunov function is negative definite.

State Transformation.

Consider the following change of variables:

$$\tilde{T} = \mathcal{H} T,  \quad (36)$$

where $\tilde{T} \in \mathbb{R}^{n \times 1}$ is the temperature difference vector along the membrane boundaries. $\mathcal{H} \in \mathbb{R}^{n \times 2n^2}$ is a non-square transformation matrix that forms the difference of each corresponding boundary, such as $$\mathcal{H} = \begin{bmatrix} 0 & \ldots & 1 & 0 & -1 & \ldots & 0 & \ldots & 0 \\ 0 & \ldots & 0 & 1 & \ldots & -1 & 0 & \ldots & 0 \\ 0 & \ldots & 0 & 0 & \ddots & 0 & \ddots & 0 & 0 \\ 0 & \ldots & 0 & \ldots & 0 & 1 & \ldots & -1 & 0 \end{bmatrix}. \quad (37)$$

To overcome any possible numerical issues, consider the right pseudo inverse $\mathcal{H}^{-1} = \mathcal{H}^T \cdot (\mathcal{H} \cdot \mathcal{H}^T)^{-1}$, which as the inverse matrix of the non-square transformation matrix $\mathcal{H}$, and this is because it has low condition number. By substituting equation (36) in equation (12), the structure for the MD dynamic model can be given as:

$$\begin{cases} \dot{\tilde{T}} = \mathcal{H} \dot{T}, \\ \quad = \mathcal{A} \tilde{T} + \mathcal{B} U + \mathcal{F}(\mathcal{H}^{-1} \tilde{T}), \\ y = \mathcal{C} \tilde{T}. \end{cases} \quad (38)$$

where $\mathcal{A} = \mathcal{H} A \mathcal{H}^{-1} \in \mathbb{R}^{n \times n}$ represents the dynamics of the membrane boundaries. $\mathcal{B} = \mathcal{H} B \in \mathbb{R}^{n \times 2}$ is the input matrix. $\mathcal{F}(\mathcal{H}^{-1}\tilde{T}) = \mathcal{H} f(T) \in \mathbb{R}^{n \times 1}$ is the nonlinear effect on the membrane boundaries where $\underline{f}(T) = \underline{b}$ of equation (20), and $\mathcal{C} = C \mathcal{H}^{-1} \in \mathbb{R}^{1 \times n}$ is the output matrix as defined earlier. Accordingly, the structure of the MD process has been reduced, and therefore, will be easier to examine and guarantee the controllability and the observability of the states on the membrane boundaries through the pairs $(\mathcal{A}, \mathcal{B})$ and $(\mathcal{A}, \mathcal{C})$, respectively. Numerical simulations have shown that the controllability and the observability conditions for the MD process are satisfied.

Following Proposition 1 above, if the following control law is applied:

$$U = \mathcal{B}^{-1}(-\kappa(\tilde{T}-y_r) - \mathcal{A}\tilde{T} - \mathcal{F}(\mathcal{H}^{-1}\tilde{T}), \quad (39)$$

where $\kappa \in \mathbb{R}^+$ is the controller gain, then:

$$e(t)^T(\mathcal{A}\tilde{T} + \mathcal{B} U(t) + \mathcal{F}(\mathcal{H}^{-1}\tilde{T})) = -\kappa e(t)^T e(t). \quad (40)$$

After, the control law will be defined as equation (39), hence asymptotic stability for the error and reference tracking is guaranteed.

Nonlinear Observer

A nonlinear observer can be used taking advantage of the well-modeled nonlinearity structure in the process. However, it can be extended to include an online constructive algorithm for finding an adequate observer gain. Consider the nonlinear Lyapunov-based observer in the following form:

$$\dot{\hat{\tilde{T}}} = \mathcal{A}\hat{\tilde{T}} + \mathcal{B} U + \mathcal{F}(\mathcal{H}^{-1}\hat{\tilde{T}}) + L(y - \mathcal{C}\hat{\tilde{T}}), \quad (41)$$

where $\hat{\tilde{T}} \in \mathbb{R}^{2n^2 \times 1}$ is the estimated state vector, and L is the observer gain matrix. Following, the observer error dynamic equation can be formulated as:

$$\dot{\bar{T}} = (\mathcal{A} + L\mathcal{C})\bar{T} + \mathcal{F}(\mathcal{H}^{-1}\tilde{T}) + \mathcal{F}(\mathcal{H}^{-1}\hat{\tilde{T}}), \quad (42)$$

where $\bar{T} = \tilde{T} - \hat{\tilde{T}}$ is the state estimation error. The following provides sufficient conditions for exponential stability of the state observer error of equation (42).

Proposition 2: There exists an exponential stable observer of the form of equation (41), if and only if, there exists a symmetric positive definite matrix, P, such that the following standard algebraic Ricatti equation is satisfied:

$$\mathcal{A} P + P \mathcal{A}^T + PR_1 P + Q_1 = 0, \quad (43)$$

where $$R_1 = \left( \gamma^2 I - \frac{\mathcal{C}^T \mathcal{C}}{\epsilon} \right), Q_1 = I(\epsilon + 1), \epsilon > 0, \epsilon \in \mathbb{R}^+, \quad (44)$$

and the observer gain matrix $L = P\mathcal{C}^T/_{2\epsilon}$.

Figure 4A:
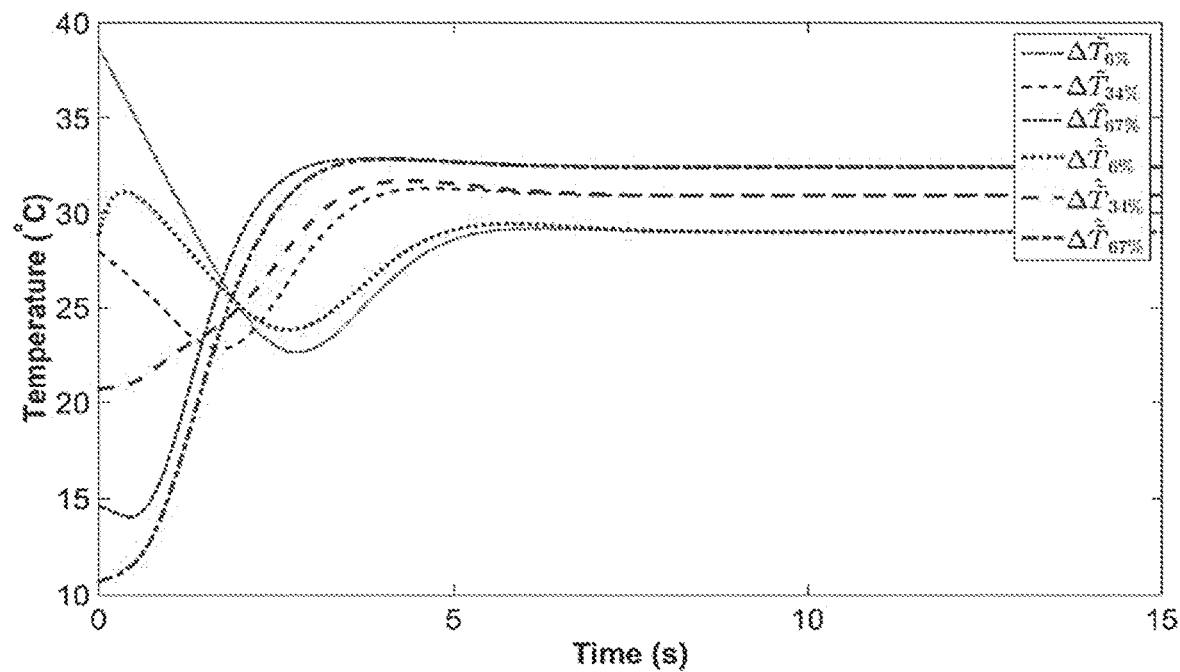
FIGS. 4A and 4B illustrate the convergence and error analysis of a nonlinear Lyapunov-based observer in accordance with various embodiments of the present disclosure.
Figure 4B:
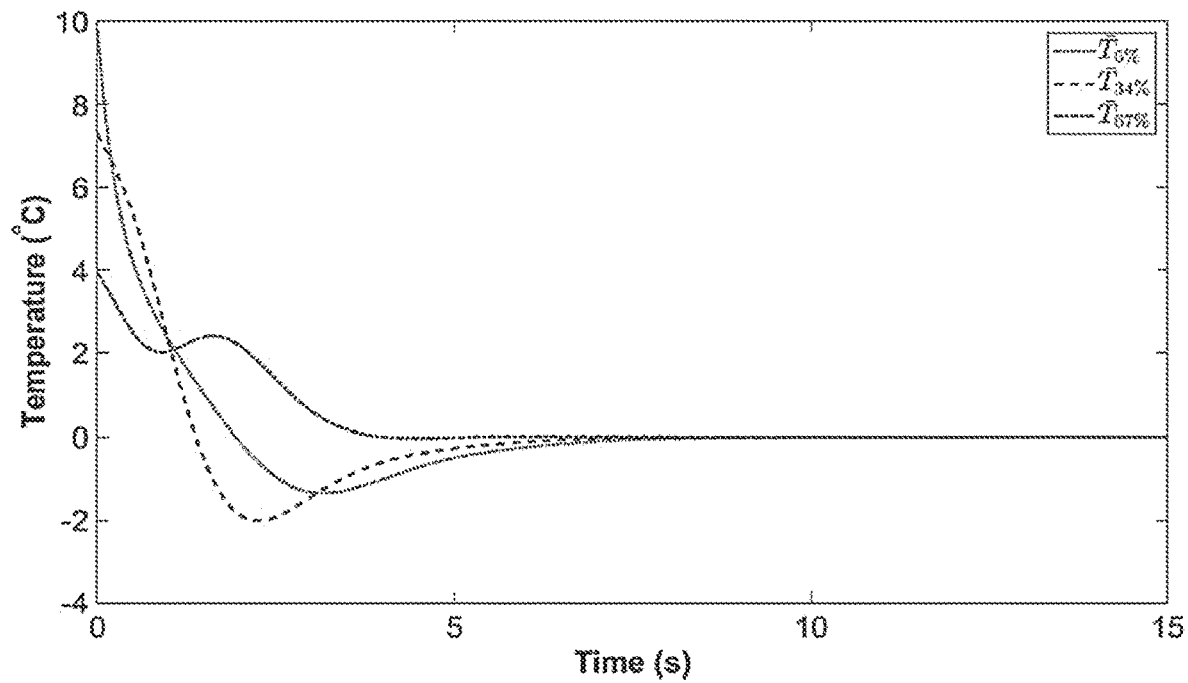

The performance of the nonlinear observer can be tested with the convergence time and error. FIG. 4A illustrates the fast convergence of the estimated states using the nonlinear Lyapunov-based observer for different locations along the membrane length. These locations are marked as a percentage of the total length of the membrane, starting from the top of the membrane to the bottom, therefore the plot shows the observer convergence on the top (6%), the middle (34%) and the bottom (67%) of the whole membrane length. The fast convergence of the observer guaranteed by taking a smaller sampling time. In the same context, the error analysis depicted in FIG. 4B illustrates the exponential convergence of the error to zero.

Nonlinear Observer Based Lyapunov Controller

Following the design of the nonlinear Lyapunov-based observer, the temperature difference along the membrane boundaries is available at each instant of time. Proceeding further, the estimated states can be feed back to a nonlinear Lyapunov controller to operate, which is valid because the observer convergence is fast. Combining the control law in equation (39) with the estimated temperature difference along the membrane boundaries in equation (41), will give the control law:

$$U(t) = \mathcal{B}^{-1}(+\kappa(\hat{\tilde{T}} - y_r) - \mathcal{A}\hat{\tilde{T}} - \mathcal{F}(\mathcal{H}^{-1}\hat{\tilde{T}}). \quad (45)$$

FIG. 5 illustrates an example of the structure of the nonlinear observer-based Lyapunov controller.

The convergence of the combined system can be examined by studying the stability of the augmented system of the dynamics of the tracking reference error e, and the observer error $\bar{T}$. The augmented error matrix is shown in:

$$\begin{pmatrix} \dot{\bar{T}} \\ \dot{e} \end{pmatrix} = \begin{pmatrix} \mathcal{A} - L\mathcal{C} & 0 \\ \mathcal{A} + \hat{K}I & -\hat{K}I \end{pmatrix} \begin{pmatrix} \bar{T} \\ e \end{pmatrix} + \begin{pmatrix} \mathcal{F}(\mathcal{H}^{-1}\tilde{T}) - \mathcal{F}(\mathcal{H}^{-1}\hat{\tilde{T}}) \\ \mathcal{F}(\mathcal{H}^{-1}\tilde{T}) - \mathcal{F}(\mathcal{H}^{-1}\hat{\tilde{T}}) \end{pmatrix}, \quad (46)$$

and can be further simplified to be:

$$\dot{\vartheta} = \mathbb{A}\vartheta + \Phi(H^{-1}, \tilde{T}, \hat{\tilde{T}}), \quad (47)$$

where $$\vartheta \in \mathbb{R}^{n \times 1} = \begin{pmatrix} \tilde{T} \\ e \end{pmatrix} \text{ and } \mathbb{A} \in \mathbb{R}^{n \times n} = \begin{pmatrix} \mathcal{A} - L\mathcal{C} & 0 \\ \mathcal{A} + K_c I & -K_c I \end{pmatrix}$$

represent the error state vector and the dynamics of the error, respectively. The nonlinear terms are represented in:

$$\Phi(\mathcal{H}^{-1}, \tilde{T}, \hat{\tilde{T}}) \in \mathbb{R}^{n \times 1} = \begin{pmatrix} \mathcal{F}(\mathcal{H}^{-1}\tilde{T}) - \mathcal{F}(\mathcal{H}^{-1}\hat{\tilde{T}}) \\ \mathcal{F}(\mathcal{H}^{-1}\tilde{T}) - \mathcal{F}(\mathcal{H}^{-1}\hat{\tilde{T}}) \end{pmatrix}.$$

Sufficient conditions for asymptotic stability for the augmented error matrix are given by the following proposition.

Proposition 3: The augmented error matrix in equation (47) is asymptotic stable, if and only if, there exists matrix $S=S^T>0$, and a positive scalar E such that the following linear matrix inequality (LMI) is satisfied:

$$\begin{bmatrix} \mathbb{A}^T S + S\mathbb{A} + \epsilon \lambda^2 I & S \\ S & -\epsilon^{-1} I \end{bmatrix} < 0. \quad (48)$$

The following shows the asymptotic stability for the error dynamics of the combined system ($\tilde{T} \to 0$, $e \to 0$). It can be shown that if X and Y are real vectors of the same dimension, then for any scalar $\epsilon > 0$, the following inequality holds:

$$X^T Y + Y^T X \le \epsilon X^T X + \epsilon^{-1} Y^T Y. \quad (49)$$

Consider the following Lyapunov function candidate:

$$V = \vartheta^T S \vartheta, S = S^T > 0. \quad (50)$$

Substituting the time derivative of V along the solution trajectories of equation (47) into equation (0) obtains:

$$\dot{V} = \dot{\vartheta}^T S \vartheta + \vartheta^T S \dot{\vartheta},$$
$$= [\mathbb{A}\vartheta + \Phi(\mathcal{H}^{-1}, \tilde{T}, \hat{\tilde{T}})]^T S \vartheta + \vartheta^T S [\mathbb{A}\vartheta + \Phi(\mathcal{H}^{-1}, \tilde{T}, \hat{\tilde{T}})],$$
$$= \vartheta^T [\mathbb{A}^T S + S\mathbb{A}] \vartheta + \Phi(\mathcal{H}^{-1}, \tilde{T}, \hat{\tilde{T}})^T S \vartheta + \vartheta^T S \Phi$$
$$(\mathcal{H}^{-1}, \tilde{T}, \hat{\tilde{T}}).$$

By using the inequality of equation (49) and taking into account the Lipshitz condition $\|f(T_1) - f(T_2)\| \le \lambda \|T_1 - T_2\|$, the following relationship can be obtained:

$$\dot{V} \le \vartheta^T (\mathbb{A}^T S + S\mathbb{A} + \epsilon SS + \epsilon \lambda I) \vartheta, \quad (51)$$

and this will be negative, if and only if:

$$\mathbb{A}^T S + S\mathbb{A} + \epsilon \lambda^2 I + \epsilon^{-1} SS < 0, \quad (52)$$

which implies that the error dynamics are asymptotically stable. Taking into account the inequality in equation (52) and using the Schur complement, the inequality in equation (48) is obtained.

Simulation and Results

Simulations were performed using the model of the MD process to check the behavior of the response, and then to check the effect of the developed controller. The simulations were done with real process parameter values, and implemented over different locations among the process domain.

Model Simulation.

Figure 7:
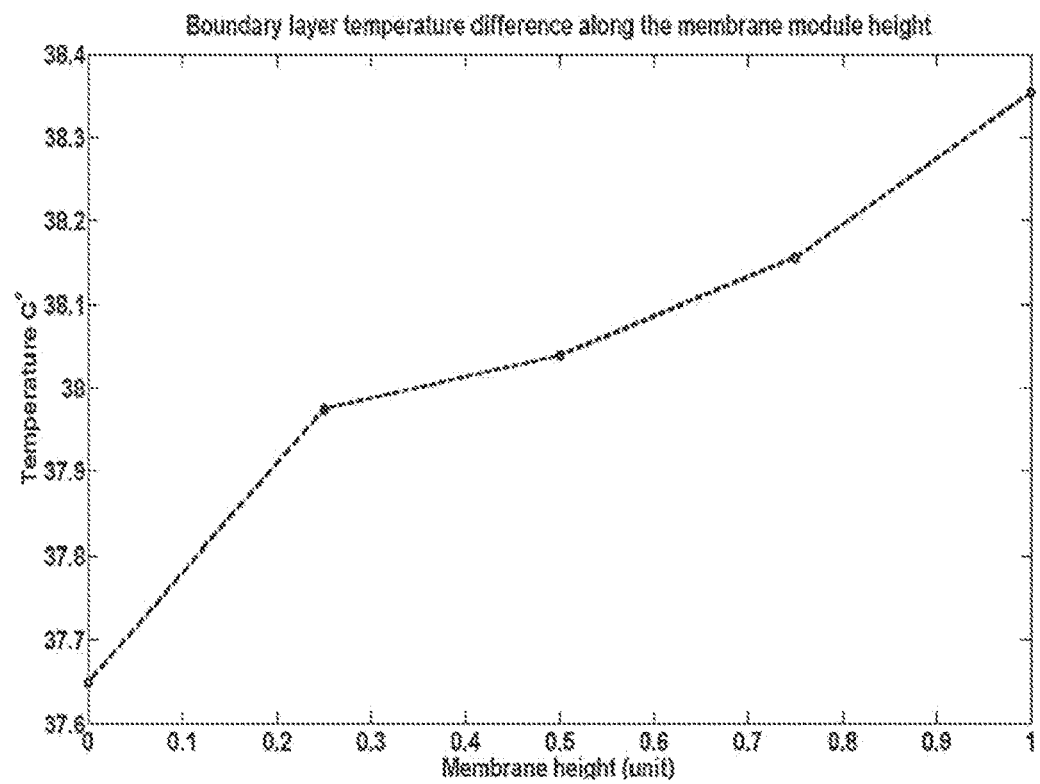
FIG. 7 is a plot illustrating the boundary layer temperature difference along the membrane module height in an open loop MD process in accordance with various embodiments of the present disclosure.

The model was simulated with the real parameter values listed in the table of FIG. 6. The temperature difference between the feed and the permeate subsystems 103 and 109 of FIG. 1 was analyzed, where the inputs are 60° C. for the feed inlet and 20° C. for the permeate inlet. The behavior of the MD process with no imposed control will be unstable, and thus the temperature difference along the membrane boundaries will not be constant and does not fall within practical values. FIG. 7 is a plot of temperature with respect to membrane height illustrating the steady-state response of the open loop system. The temperature difference of the boundary layer temperature without controller function of the membrane module length is shown. The difference evolved with time for different locations along the membrane boundary layer, and thus the trans-membrane heat flux was not fixed along the membrane length. In addition, if the temperature difference is not sufficient, no heat flux will be produced or transferred. The induced fluctuations in the temperature difference along the membrane boundaries can lead to instability in the generated heat flux and consume more energy. The instability of the produced heat flux can cause a fluctuation in the water production as well as significant problems for the process.

Controller Simulation.

Figure 8:
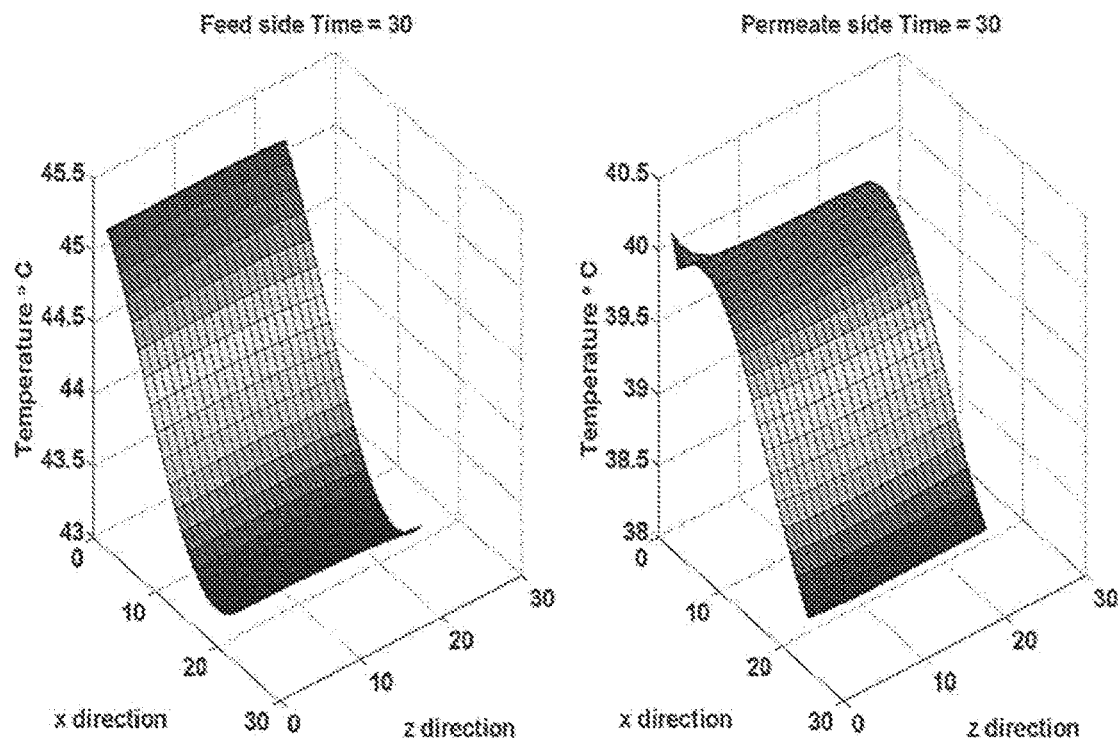
FIG. 8 includes surface plots illustrating examples of the behavior of the MD process at steady-state among the process domain in accordance with various embodiments of the present disclosure.

The role of the nonlinear controller is to maintain the difference temperature along the membrane boundaries to be almost fixed around a desired reference. The value of this reference has been chosen to be within a range of 5° C. to 15° C., following practical guidance for sufficient water production. In the case of the closed loop system, the difference of the boundary layer temperatures was kept fixed at the desired reference (e.g., equal to 5° C. or 10° C. in the simulations). At the same time, the values of the control inputs were physically reasonable and energy saving. Referring to FIG. 8, shown are surface plots illustrating an example of the behavior of the process at steady-state among the process domain. It shows the convergence of the output to the desired reference among all the process domain.

Figure 9A:
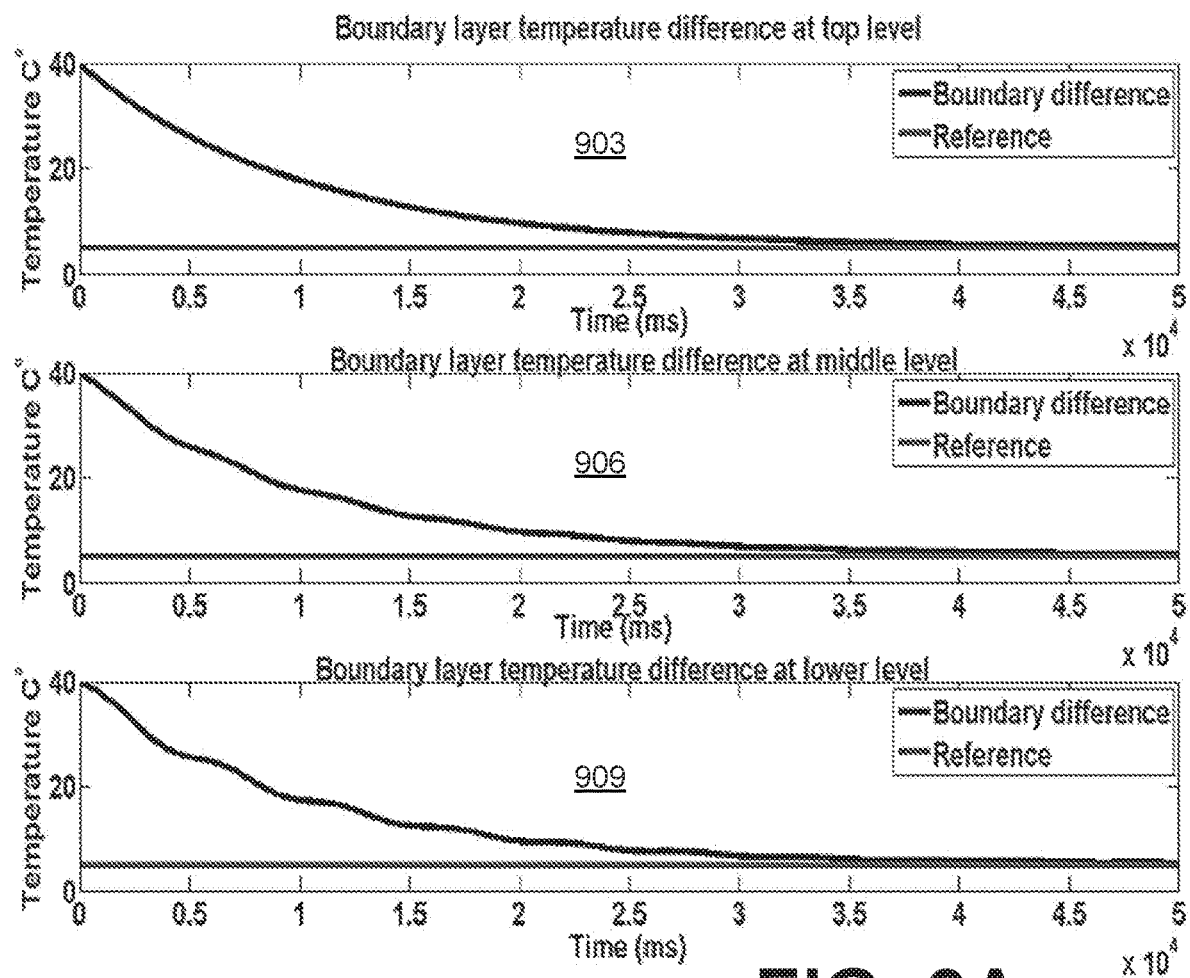
FIGS. 9A and 9B include plots illustrating examples of the temperature difference in different locations along the membrane module length in accordance with various embodiments of the present disclosure.
Figure 9B:
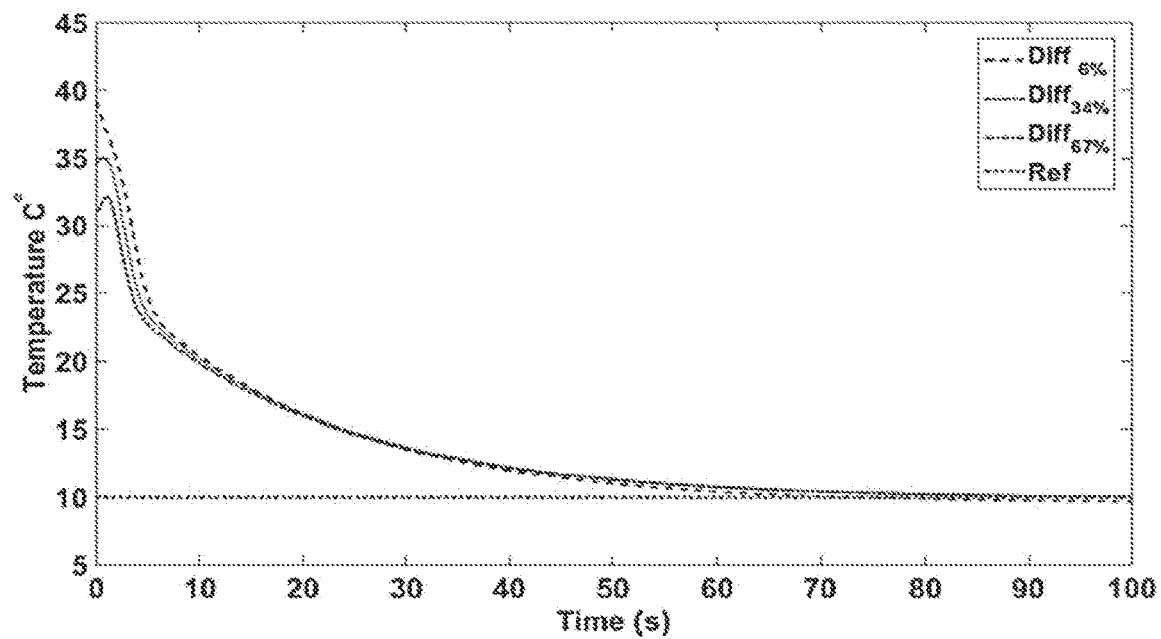

Referring next to FIG. 9A, shown is an example of the temperature difference in different locations along the membrane module length. The first plot 903 shows the temperature difference with respect to a 5° C. reference at the top of the membrane module, where the second plot 906 shows the temperature difference at the middle of the membrane module, and the third plot 909 shows the temperature difference at the bottom of the membrane module for the closed loop response. FIG. 9B shows the convergence of the temperature difference for the top (6%), middle (34%) and bottom (67%) locations on the membrane boundaries to the desired reference of 10° C. The convergence of the temperature difference is accompanied with an acceptable evolution of the control inputs within the predefined range.

Figure 10A:
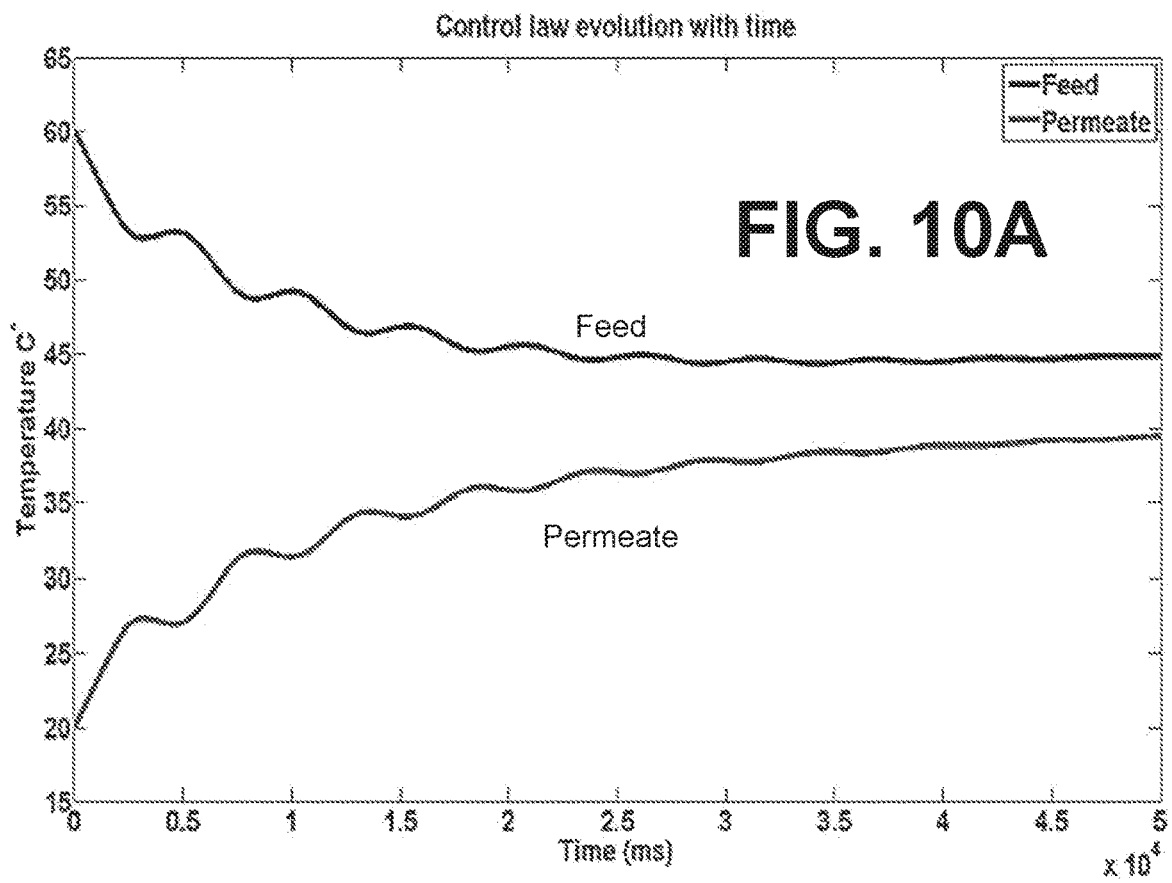
FIGS. 10A through 10C are plots illustrating the evolution of control law inputs and the evolution of the reference tracking error of the MD process with time in accordance with various embodiments of the present disclosure.
Figure 10B:
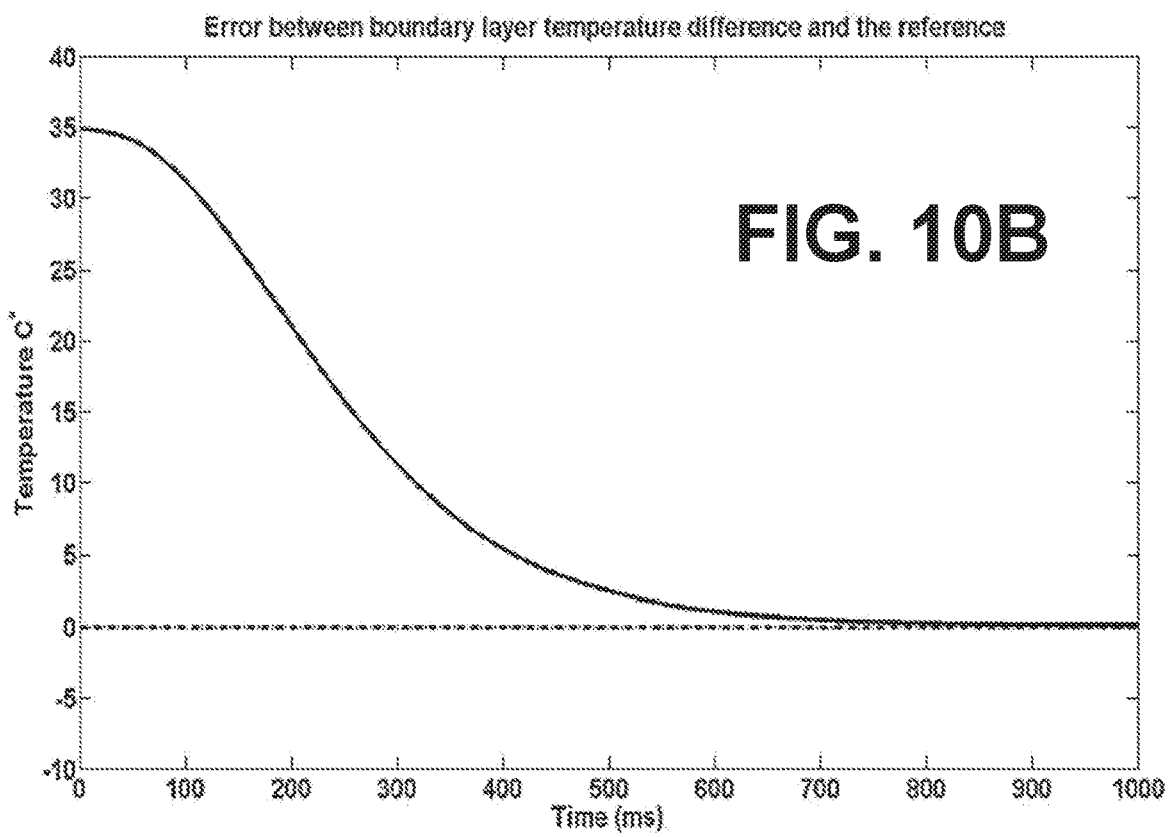
Figure 10C:
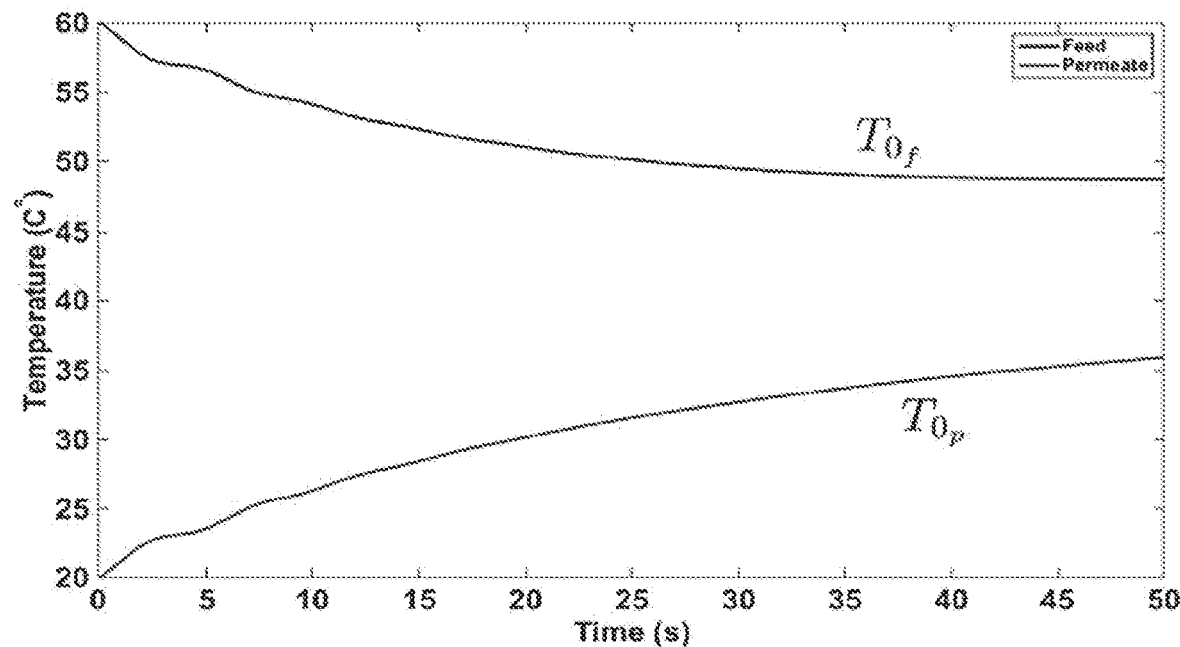
Figure 10D:
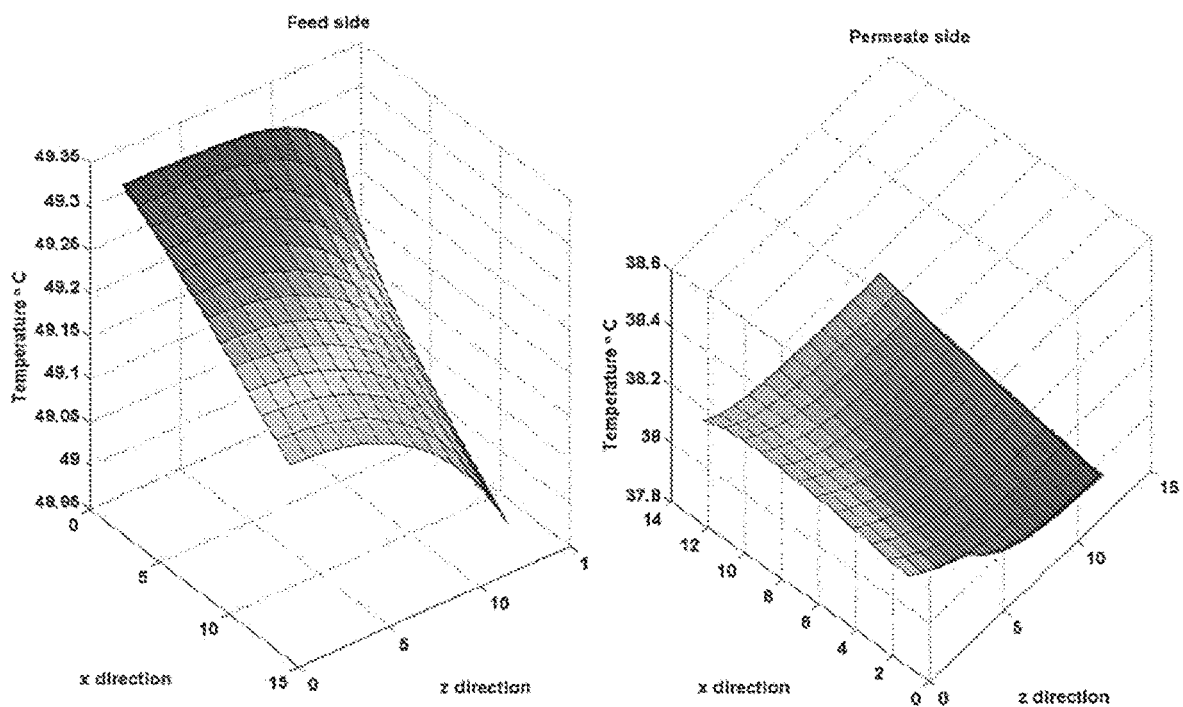
FIG. 10D includes surface plots illustrating examples of the behavior of the MD process at steady-state with the Lyapunov control in accordance with various embodiments of the present disclosure.

FIG. 10A shows the evolution of control law inputs with time for the case with the 5° C. reference. The inputs are within economical energy supply ranges. The evolution of the error with time proves the asymptotic stability achieved in the Lyapunov function derivative. The evolution of the reference tracking error with time, where the response is asymptotically stable using the observer-based nonlinear Lyapunov controller, is shown in FIG. 10B. FIG. 10C depicts the time evolution of the control inputs for the case with the 10° C. reference. Reaching the steady state phase, with no disturbance, the MD process experiences a stable behavior among all its designated domains. FIG. 10D illustrates the effect of the controller on the process during the steady state phase with the 10° C. reference.

Controller Gain Variation.

Figure 11A:
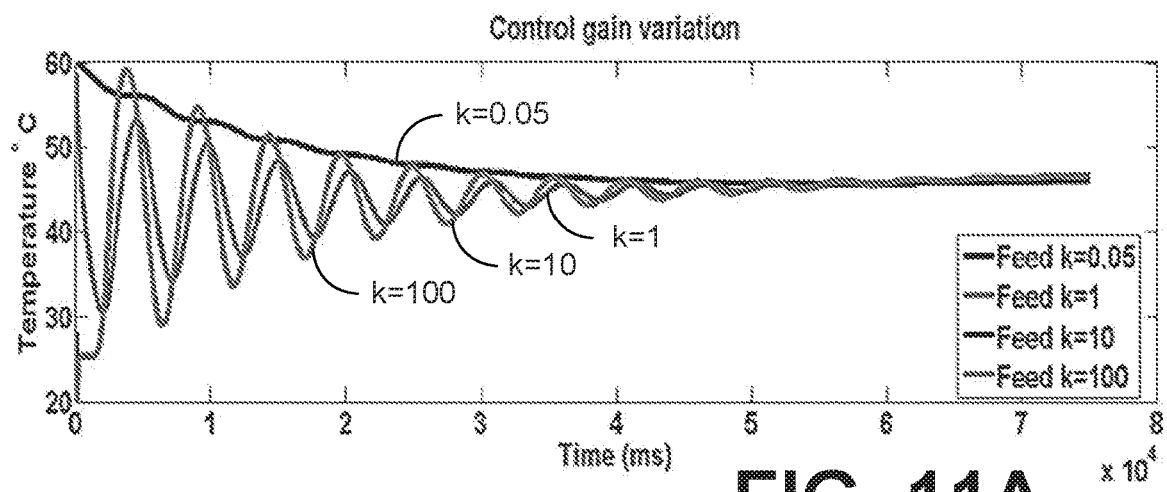
FIGS. 11A and 11B include plots illustrating the effect of the controller gain on the control law in accordance with various embodiments of the present disclosure.
Figure 11B:
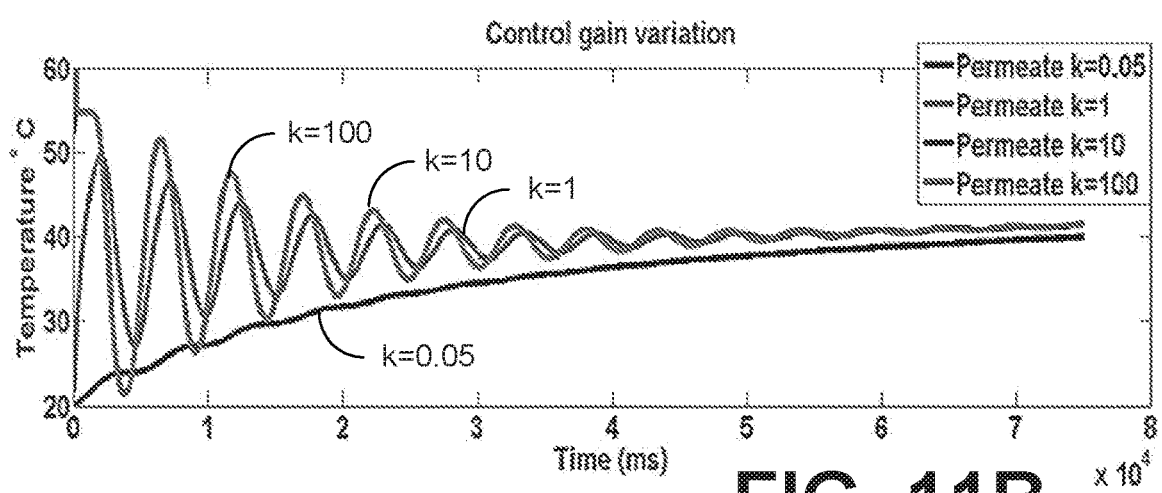

The controller gain is a constant to smooth out the response of the controller, and reduce the oscillations that may occur in the transient response. The controller gain is a tradeoff between the convergence speed to steady state and the smoothness of the response. The effect of the controller gain on the control law is illustrated for the feed and permeate in FIGS. 11A and 11B, where it is noticeable that a low gain gives low oscillation control law. A low gain gives an oscillation free control law response. At the same time, reducing the gain forces the control law to be within the specified economical inputs range, without spikes in the response.

A Lyapunov based boundary controller for the nonlinear membrane distillation model has been presented. The model is based on a 2D advection diffusion equation and extended to be symmetric, and flexible in terms of the boundary conditions. Semi-discretization has been applied over the continuous PDE model, and a system of nonlinear ODEs has been obtained and written in a state-space representation, where it presents the model in a suitable form for control techniques. A good approximation for the continuous model can be granted, in which spatial step sizes have a significant role for stabilizing the numerical solution, and refining the model. The disclosed controller as applied over the state-space representation of the nonlinear model, where the output converges to the desired reference asymptotically. Certain limitations were put over the control law inputs to be within an economic energy saving ranges, and achieve asymptotic stability to the system. The effect of the controller gain was justified to be within small values to avoid oscillations in the responses. The Appendix provides additional description related to the control of the boundary layers temperature differences through the inlet temperatures and/or the inlet flow rates for the feed and permeate subsystems 103 and 109 of the MD process 100 of FIG. 1. In some embodiments, the water production can be maximized (optimized) while decreasing the energy consumption of the MD process 100. In other embodiments, the water production can be maintained at a desired level using the nonlinear Lyapunov controller.

Experiment and Results

Figure 12:
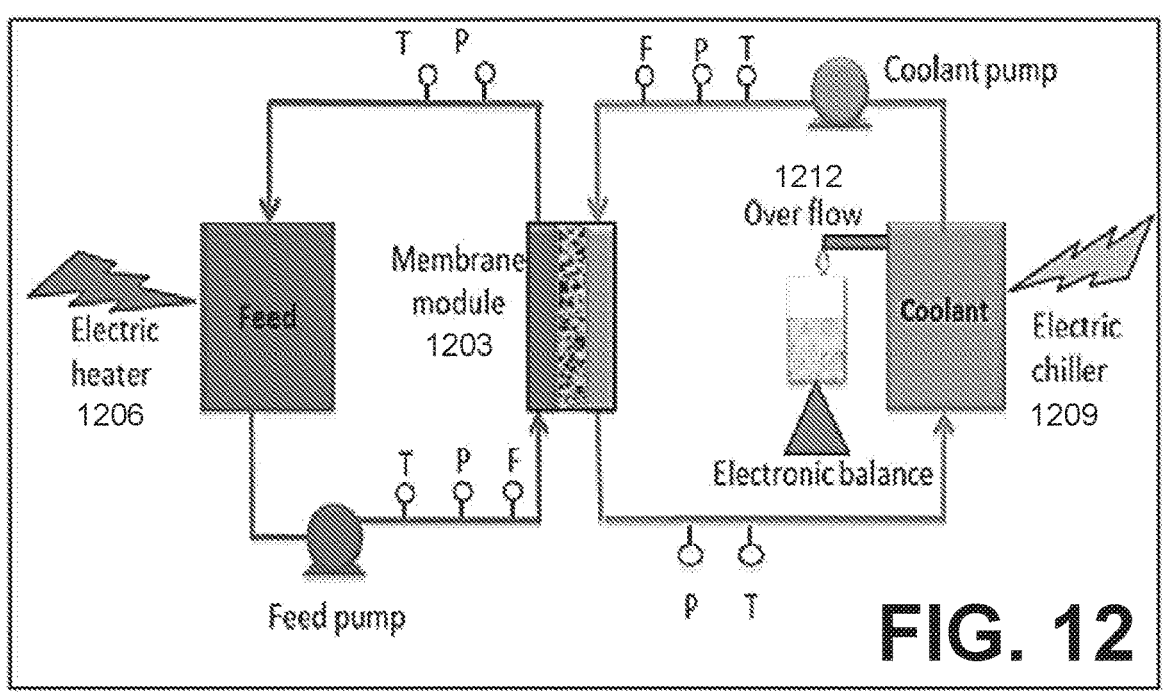
FIG. 12 is a schematic diagram illustrating an experimental set-up in accordance with various embodiments of the present disclosure.

A fully automated DCMD experimental lab scale set-up was locally designed and fabricated. FIG. 12 shows a schematic diagram of the experimental set-up. A flat sheet membrane module 1203 with an active surface area of 0.005 m², with flow channel dimensions of 0.1 m×0.05 m×0.002 m, was designed and fabricated using polymethylmethacrylate (PMMA) material. A composite membrane with a polytetrafluoroethylene (PTFE) active layer and a nonwoven polypropylene support layer was used for MD testing. Details of the membrane characteristics are presented in the table of FIG. 13A and the feed water (Red Sea water) characteristics are presented in the table of FIG. 13B. Red Sea water was preheated to desired temperatures and circulated through the feed side of the membrane module 1203, while de-ionized (DI) water was circulated through the permeate side of the membrane module 1203 simultaneously in a countercurrent mode. Feed and permeate temperatures were controlled using thermoregulators (e.g., electric heater 1206 and electric chiller 1209).

Fresh seawater was used as feed for each experiment. The permeate generated during the MD process resulted in an increase in the volume of coolant and overflow 1212 was allowed to happen through the outlet of the permeate/coolant tank. The overflow permeate was collected in a separate container placed on a weighting balance. The increase in weight of the container was continuously monitored and recorded. Pressure (P), temperature (T) and flow rates (F) were continuously monitored at the inlet and outlet of the membrane module 1203 of both the feed and permeate sides using respective sensors connected to data acquisition unit equipped with a Lab View Software. Conductivities of both permeate and feed solutions were continuously monitored and measured using conductivity meters (e.g., Oakton Eutech Instruments, Malaysia).

The influence of feed water temperature ranging from 40° C. to 70° C. on water vapor flux was studied by maintaining a constant temperature on the permeate side at 20° C. All the data were recorded after reaching the steady state temperature. Similarly, the influence of feed water temperature ranging from 30° C. to 75° C. on trans-membrane flux was also studied by ramping the feed solution temperature at a rate of 0.05° C. per minute. During ramping experiments, the coolant temperature was also maintained at 20° C. Feed and coolant flow rates were kept constant at 90 L/h and 60 L/h, respectively, for all the experiments. The salt rejection was calculated by: $SR=(1-C_p/C_f)*100$, where $C_p$ and $C_f$ are the salt concentrations of permeate and feed solutions, respectively. A salt rejection of 99.99% was observed in all experiments. The water vapor flux was determined by $J_v=mw/At$, where mw is the weight of collected permeate at a particular time interval t, and A is the effective membrane area.

Model Validation.

The ADE model was simulated with a developed MATLAB®-software and validated with experimental data through two sets of experiments. For validation purposes, the same MD parameter values and membrane specifications as well as environment conditions were applied.

Steady-State Validation.

Figure 14A:
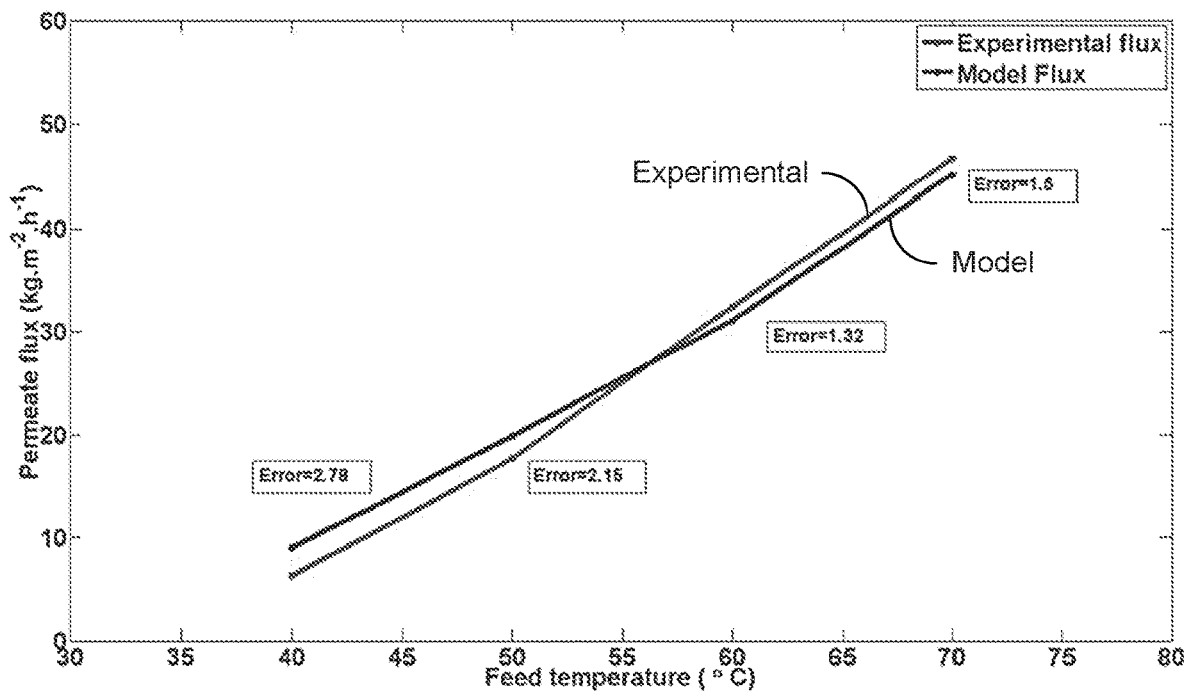

Referring to FIG. 14A, shown is the validation at the steady-state phase between the experimental data and the simulations for different feed inlet temperatures. The absolute error is also presented. The model acts best when compared to experiments at high feed inlet temperatures varying from 55° C. to 70° C., while the absolute error is a bit larger for lower temperatures below 40° C. This may be attributed to the fact that water vapor flux is higher at high feed temperatures, which reduces the errors in measurements compared to the very low flux obtained at low feed inlet temperatures.

Transient Validation.

Figure 14B:
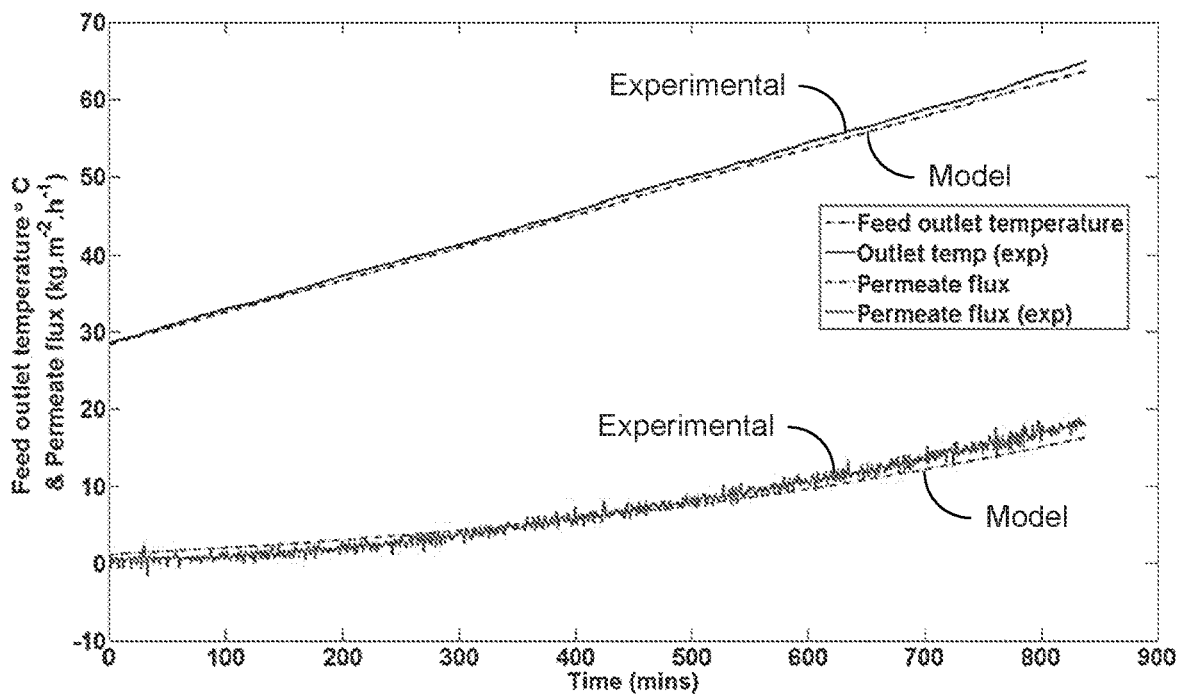

In the other set of experiments, the feed inlet temperature was increased in a ramp fashion from 30° C. to 75° C. The increment was 0.1° C. every 2 minutes, and the outlet feed temperature as well as the permeate flux were recorded. The comparison between the experiments and the model is shown in FIG. 14B. In this observation, the transient response of the outlet feed temperature and the permeate flux showed high consistency with the experimental data. This contributes towards the validity of the dynamic model to be extended to the transient phase.

The MD process is highly sensitive to considerable variations in the membrane parameter values. For example, FIG. 14C shows the effect of the pore size variation on the membrane flux, where it is noticeable that the higher pore size leads to higher permeate flux. At the same time, the Liquid Entry Pressure (LEP) should not be exceeded to ensure no pore wetting is occurring inside the membrane pores. The LEP is equal to 15 PSI for the used membrane, while the actual pressure difference at the liquid-vapor interface ΔP is lower or equal to (7.64-8.33 PSI) for pore size equals to 0.5 μm and along temperature variation between (20° C.-60° C.), respectively. The variation of the membrane parameter values is very likely to happen when manufacturing the membranes, and so it leads introduce some divergence in some cases.

Model Analysis.

The ADE model was applied inside the feed solution as well as the permeate solution. For simulations and up-scaling purposes a software in MATUAB® was developed to solve the dynamic model and obtain behavior plots for analysis and improvement aspects. In the simulations, real numeric values for the membrane parameters were used as listed in the tables in FIGS. 13A and 15. The simulations show the response in transient and steady-state phases. The feed and coolant temperatures were set at 60° C. and 20° C., respectively.

Figure 16A:
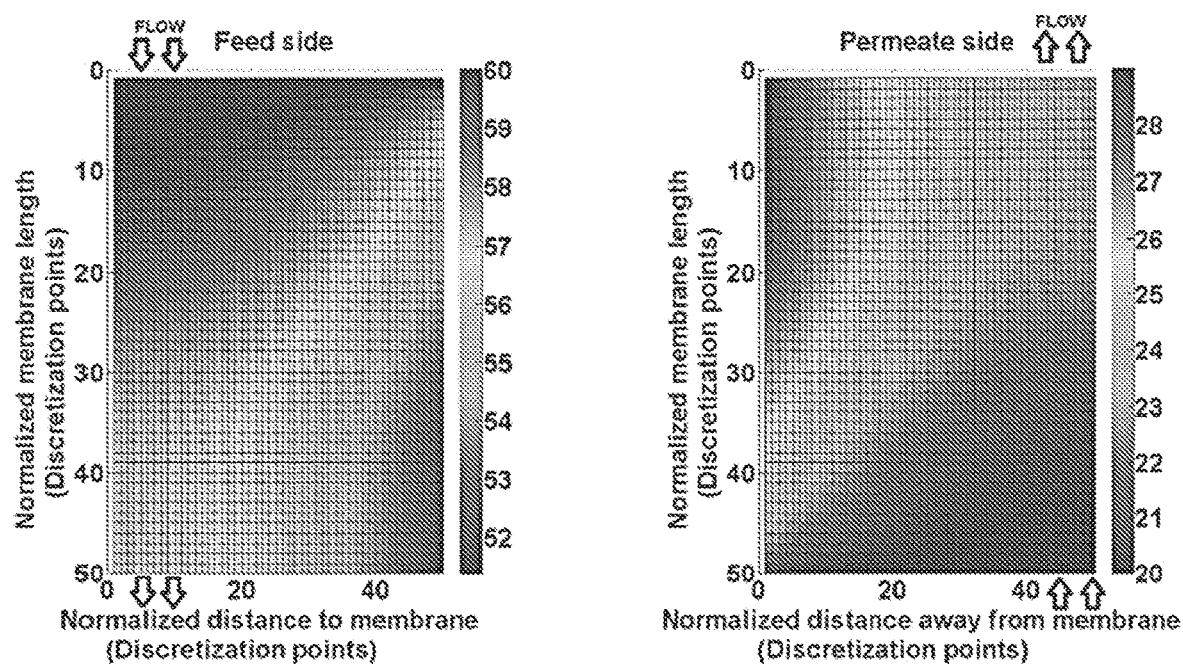
Figure 16B:
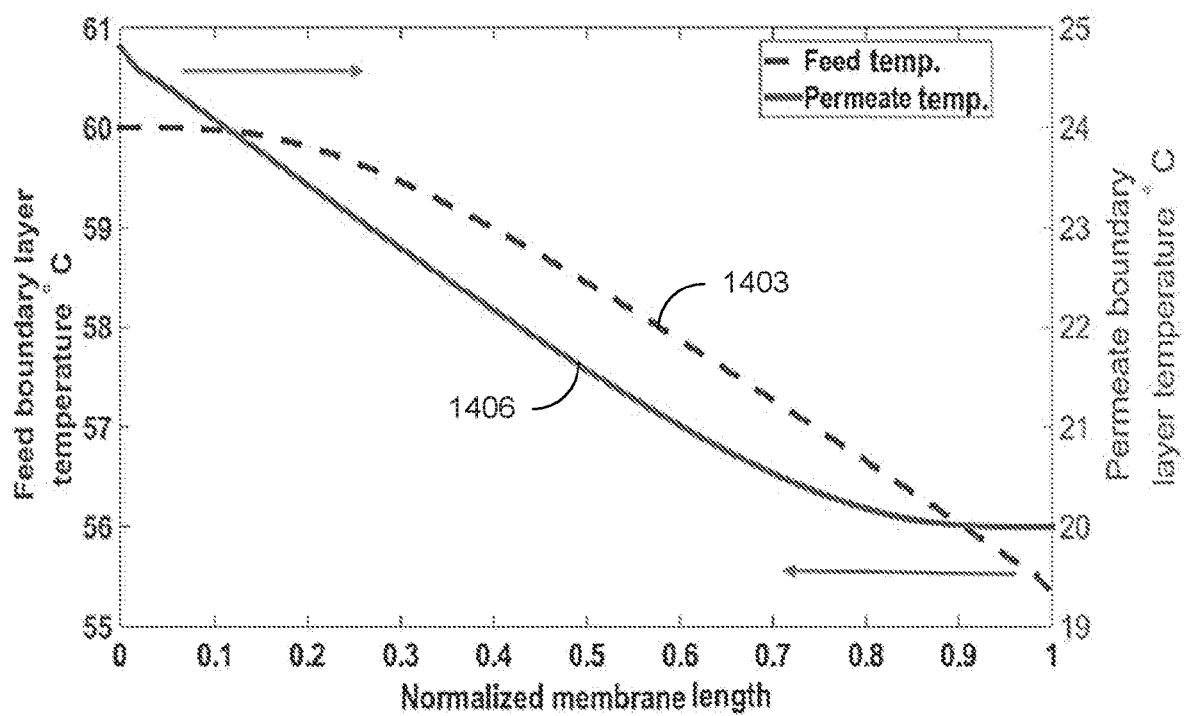
Figure 16C:
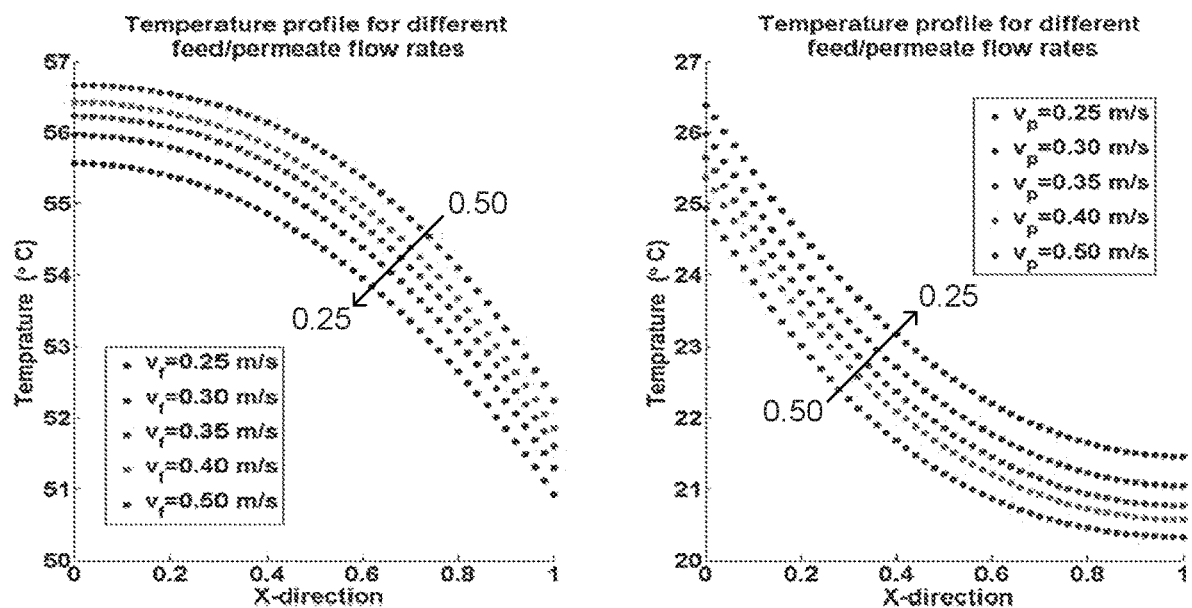

FIG. 16A illustrates the evolution of the feed and permeate solution temperatures at specific instant of time during the transient phase. The left plot of FIG. 16A shows the feed bulk temperature to be higher than the temperature at the membrane boundary layer from the feed side, and in a same manner the right plot of FIG. 16A shows that the temperature of the membrane boundary layer from the permeate has a higher temperature than permeate bulk. It also shows that the difference of temperature between the two sides of the membrane (the driving force) is higher at the top side of the module (feed inlet side) and decreases gradually towards the bottom side (feed outlet side), which is in agreement with the experimental data. FIG. 16B shows the evolution of temperature at the membrane interfaces, where the feed interface (curve 1403) ranges between 55° C. and 60° C. and the permeate interface (curve 1406) ranges between 20° C. and 25° C.

The flow rate of the feed and the permeate streams have a significant role in managing the heat transfer inside the MD module 1203 (FIG. 12). The flow rate controls the amount of the convective heat that transfers throughout the bulk solution, in which increasing its value makes the heat transfer via convection in the bulk solution more than the conduction through membrane pores. It is useful to have high convection effect, however continuous increasing in the flow rate is unprofitable, because the heat flux would saturate eventually. A smart compromise can take place between convection and conduction mechanisms. The relation between the feed flow rate and the temperature for different flow rates is illustrated in FIG. 16O. Temperature of water molecules near the inlet increases rapidly while increasing flow rate, and therefore, temperature polarization and residence time decrease, while energy consumed by the flow pumps increases.

The temperature polarization was simulated to check the time evolution of its coefficient (TPC). The formula of the TPC is:

$$TPC = \frac{T_{mf} - T_{mp}}{T_{bf} - T_{bp}}. \quad (53)$$

Figure 16D:
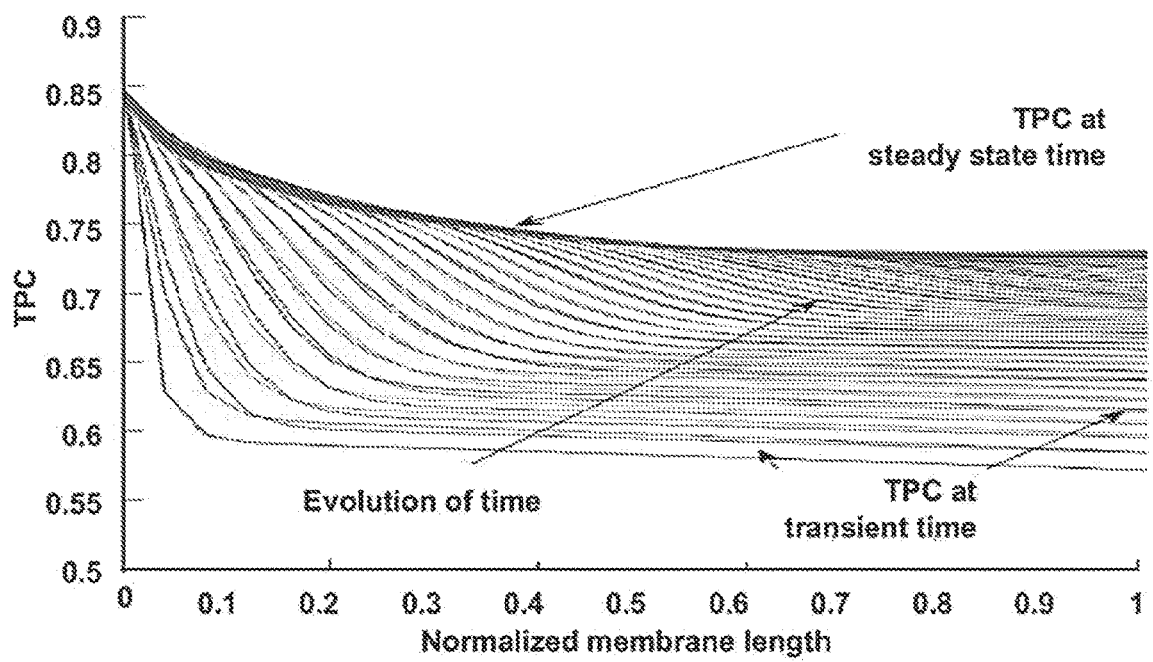

The value of TPC varies from zero for systems that suffer from large boundary layer resistances to unity for well-designed systems. FIG. 16D shows the evolution of TPC with time. During the transient phase of the process the amount of heat transfer through the membrane is low due to the starting of heat accumulation, and then it magnifies and increases after reaching steady-state phase.

A dynamic Lyapunov-based model was validated for control of the MD process. The mechanisms of heat transfer that occur in the feed and permeate solutions were modeled with a 2D Advection-Diffusion Equation (ADE) model. The model is able to describe the behavior of the MD process in a transient phase as well as in a steady-state phase. The model predictions were strongly correlated with experimental data in both steady state and transient phases, with model predictions being within ±5% of the experimentally obtained values.

Extremum Seeking Control (ESC)

The use of a perturbation-based extremum seeking control (PESC) scheme is proposed, with no loss of generality to all ESC schemes, to maximize the clean water production of a MD process with respect to the lowest energy consumption. The principal idea of the ESC is achieved by finding suitable operating set-points that are able to maximize or minimize a desired performance function. The PESC scheme can be used to simultaneously identify and regulate the MD process dynamic model to generate maximum permeate flux subjected to the minimum energy consumption of either the feed pump flow rate alone with constant permeate pump flow rate, or both the feed and the permeate pumps flow rates. The dynamic model for the MD process based on the 2D ADE can be used. Moreover, the fact that the MD process is nonlinear with most states inaccessible, the nonlinear Lyapunov-based observer can be used to provide the PESC with an accurate estimate of the process states using the available measurements.

Perturbation Based ESC.

Figure 17A:
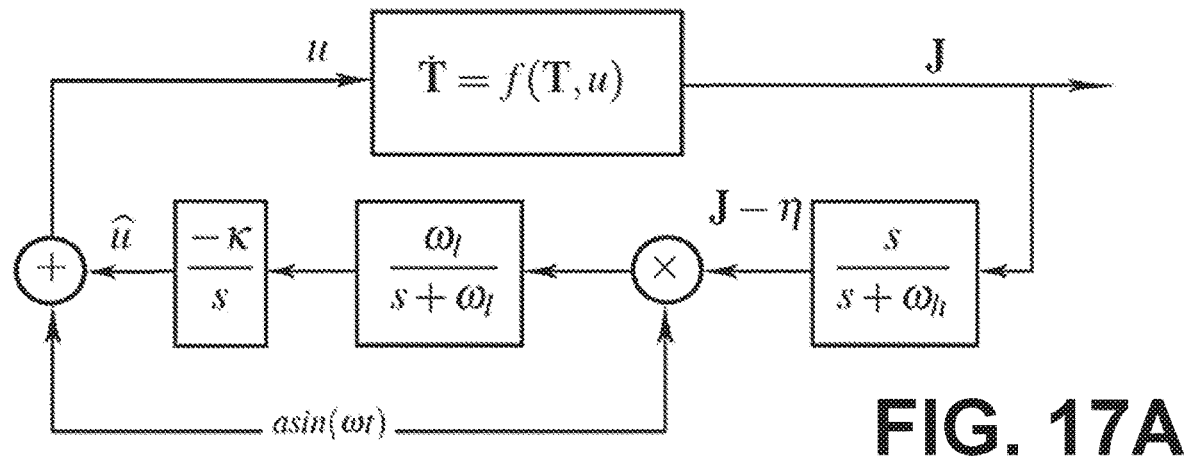
FIGS. 17A through 17C are schematic diagrams illustrating examples of perturbation-based extremum seeking control (PESC) in accordance with various embodiments of the present disclosure.

PESC is a scheme for the extremum seeking control (ESC). It has the advantage of performing continuous gradient type optimization with fast adaptation and easy implementation. PESC uses a dither signal (e.g., a sine wave) to perturb the performance function and estimates its gradient. Then, the gradient estimation is used to drive the process to a desired extremum using an integrator and the same dither signal. FIG. 17A illustrates an example of the components of a basic PESC scheme. A wash out filter is one of the components that is used to kill the DC component of the signal J. Despite the fact that multiplying the signal y with a zero mean dither signal sin($\omega$t) performs the same role, the wash out filter is more effective and does not require the dither frequency $\omega$ to be relatively high. The low pass filter is not a necessary component for the PESC design, however it can be important for filtering out cos(2$\omega$t) signals.

Figure 17B:
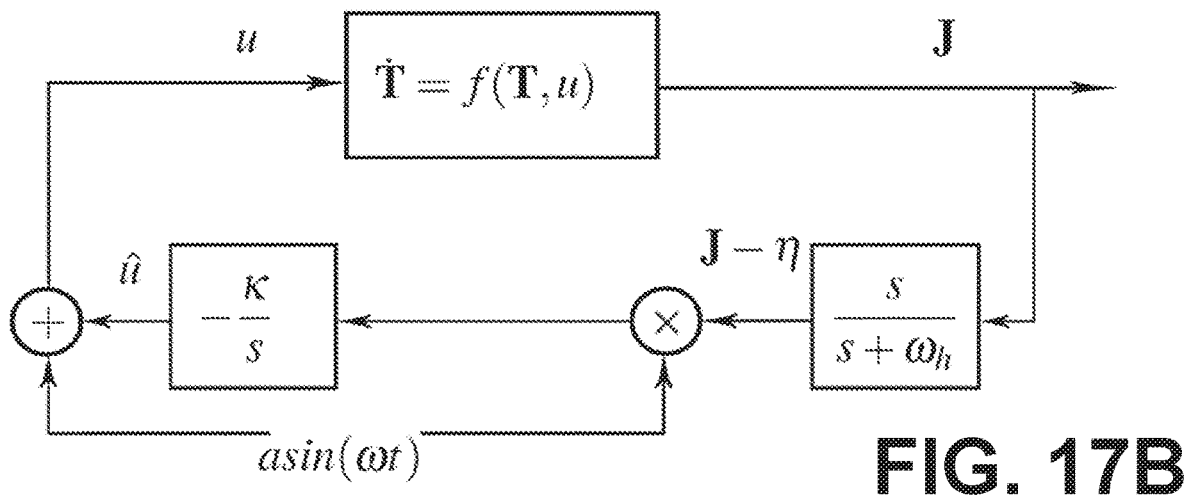

The PESC scheme in FIG. 17B provides few design parameters (e.g., a, κ, $\omega$, $\omega_l$ and $\omega_h$) to tune during the setting of the process. Some recommendations for tuning these parameters are include a smaller amplitude a can lead to smaller residual error at the minimum, but it may also lead to being stuck at a local minimum, and the converse can also be true. Moreover, the amplitude a jointly with the gain κ can control the convergence speed of the scheme. Wash out and low pass cut-off frequencies $\omega_h$ and $\omega_l$, respectively, should be smaller than the dither signal frequency $\omega$, so the filter kills the DC component of the signal J without distortion to the gradient estimation.

Problem Formulation.

Consider the MD process dynamic discrete model given by:

$$\begin{cases} \dot{T}(x, z, t) = A(u)T(x, z, t) + f(T(x, z, t)) \\ y = CT \end{cases} \quad (54)$$

where vecto $T \in \mathbb{R}^{2n^2 \times 1}$r is the state vector which represents the temperature distribution at each grid point) inside the feed and the permeate domain ($T_f$, $T_p$) for the time evolution as described with respect to equations (12)-(17), and the generated performance function:

$$J(T, u) = -|\mathcal{J}(T)| + \frac{1}{2}\mu|\rho u| \quad (55)$$

for optimization. The performance function, J, is a function of the temperature distribution inside the designated process domain T via the permeate vapor flux $\mathcal{J}$ (T), especially the ones associated with boundary layers of the membrane, and $u \in [u_f, u_p]^T$, which represents the pumps flow rates for either the feed container or both the feed and the permeate containers. $\rho$ is the water density, and it is used to fix the unit consistency for the performance function. $\mu$ is a regularization coefficient that is used to adjust the weight of each term in the performance function. During the process simulations, it is possible to shed more light on certain cases where one term is more dominant over the other. $|\mathcal{J}(T)|$ is the absolute value of the permeate vapor flux as in the Knudsen diffusion model for the mass transfer coefficient given above, where the negative sign indicates the maximization.

Single Parameter PESC.

Consider optimizing the performance function in equation (55) to be subject only to the feed pump flow rate. Consequently, permeate pump flow rate $u_p$ is kept constant, while $u = u_f$ is the control. Note that in practice, the feed pump flow rate has significant influence on the process performance more than the permeate pump flow rate.

The PESC scheme is applied to equation (55), where the permeate flux function is evaluated simultaneously with the evaluation of the temperature distribution (T) using the 2D ADE model. Afterwards, the DC content inside the performance function in (55) is eliminated using the wash out high pass filter, as shown in:

$$(J-\eta)(s+\omega_h) = Js,$$

$$\dot{\eta} = -\omega_h J + \omega_h \eta. \quad (56)$$

Then it is multiplied with the dither signal a sin($\omega$t) that has a small amplitude a, and an integrator with gain $\kappa$ to extract the gradient direction.

$$\dot{\hat{u}} = a\kappa \sin(\omega t)\hat{u} - a\kappa J \sin(\omega t). \quad (57)$$

The adaptation signal, $\hat{u}$, shifts the dither towards the gradient direction, as described in:

$$u = \hat{u} + a \sin(\omega t). \quad (58)$$

It is recommended that the cut-off frequency of the wash out high pass filter $\omega_h$, to be smaller than the frequency of the dither signal $\omega$, and the amplitude of the dither signal a and the gain $\kappa$ be small as well. FIG. 17B illustrates the principal steps that the PESC follows to update the control.

Multiple-Parameter PESC.

To further broaden the optimization analysis on the MD process, consider optimizing the performance function in (55) to be subject to both the feed and the permeate pumps flow rates to be control inputs. This would considerably highlight on the impact of the feed pump flow rate and the permeate pump flow rate on the process production, and the interference between them.

The optimization procedure is similar to the single parameter case, however the multiple-parameter PESC considers each control input in a separate loop with a specific dither signal that has some phase shifts (e.g. 0 and $\pi/2$). These phase shifts are introduced to compensate for the delays provided by the plant dynamics and the performance function J(T,u) in equations (54) and (55), respectively. The design parameters are set for each input independently, and then the whole process is tuned out to have an optimized behavior. The following equations show the dynamic representation for the feed and the permeate pumps flow rates.

$$\dot{\hat{u}}_f = a_2 \kappa_2 \sin(\omega_2 t - \phi_2)(\eta_2 - J) \quad (59)$$

$$\dot{\hat{u}}_p = a_1 \kappa_1 \sin(\omega_1 t - \phi_1)(\eta_1 - J) \quad (60)$$

$$\dot{\eta}_2 = -\omega_{h2}\eta_2 + \omega_{h2}J \quad (61)$$

$$\dot{\eta}_1 = -\omega_{h1}\eta_1 + \omega_{h1}J \quad (61)$$

Afterwards, each control inputs will consist of the adaptation signal in addition to the dither signal.

$$u_f = \hat{u}_f + a_2 \sin(\omega_2 t) \quad (63)$$

$$u_p = \hat{u}_p + a_1 \sin(\omega_1 t) \quad (64)$$

Figure 17C:
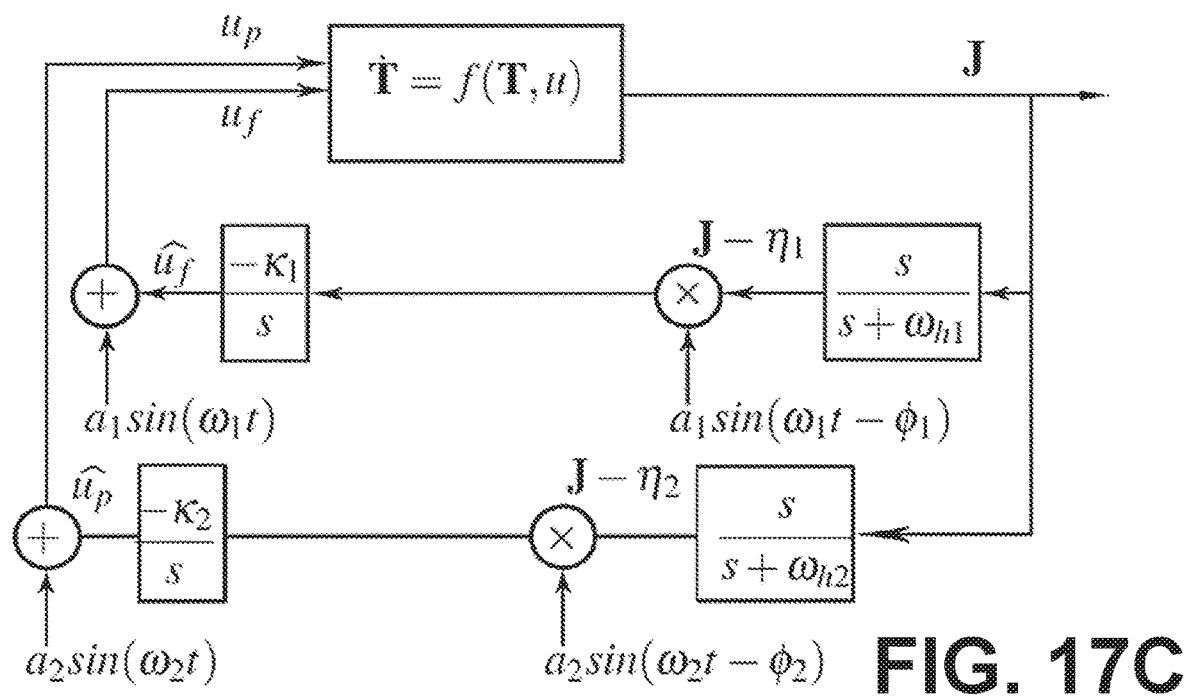

FIG. 17C illustrates a diagram of the main components for the multiple-parameter PESC.

Anti-Windup PESC.

The presence of an integrator in any PESC causes, in some occasions, the control inputs to wander outside their acceptable and feasible domain. This may facilitate the actual inputs to saturate on the actuators (e.g., pumps) domain boundary. This phenomenon is similar to the integrator wind-up in classic control. Consider an anti-windup technique to overcome input saturation phenomenon. This technique is preferable over dealing with the saturation as constant, since the process is dynamic and more likely to have input saturation. This technique allows the imposition of certain constraints on the control inputs to bound them with physical limits. Technically, it drives the actuator back to the unsaturated mode when input saturation is about to happen by using a penalty-like scheme to prevent or overcome saturation.

Combine the anti-windup technique along with the PESC scheme, and define a saturation function as in:

$$sat(u, u_s) = \begin{cases} u_{max} & \text{if } u \geq u_{max} \\ u & \text{if } u_{min} \leq u \leq u_{max}, \\ u_{min} & \text{if } u \leq u_{max} \end{cases} \quad (65)$$

where $u_s = [u_{max}, u_{min}]^T$ and $u_{max}$ and $u_{min}$ are the upper input limit and the lower input limit, respectively. $K_{aw}$ is a design parameter that adds more significance to the saturation function weight. The saturation function is placed before the process model, and defines an appropriate input v for a feedback. FIG. 17D shows a diagram for a single parameter PESC with anti-windup technique.

Similar to the previous cases, the adaptation signal is evaluated, however in this case, it includes the effect of the anti-windup. Following equations present the adaptation signal.

$$\dot{\hat{u}} = a\kappa\eta\sin(\omega t)\hat{u} - aJ\kappa\sin(\omega t) + K_{aw}(sat(u, u_s) - u), \quad (66)$$

$$\dot{\eta} = -\omega_h J \quad (67)$$

The same procedures are applicable to multiple-parameter PESC, however the anti-windup model is added to each control input channel to prevent input saturation.

Observer Based PESC

The MD process model is observable, and the present nonlinearity is Lipshitz continuous. For these reasons, an observer can be used to provide an estimate of the MD process states and feed them to the PESC. The observer is nonlinear due to the presence of nonlinearity in the process model of equation (54).

Nonlinear Lyapunov-Based Observer Design.

The advantage of having a good model for the present nonlinearity enables consideration of a nonlinear observer that can be modified with an algorithm to find an adequate observer gain. Therefore, the MD process nonlinear model in equation (54) can be extended and adapted, where the stability proof of the observer was done for a class of nonlinear systems given by:

$$\dot{T} = AT + Bu + f(T). \quad (68)$$

where A is the dynamics matrix, B is the input matrix, f(T) is the nonlinearity vector in the model and T is the state vector. For the observer design, consider the nonlinear Lyapunov-based observer in the following form:

$$\dot{\hat{T}}(x,z,t) = A(u)\hat{T}(x,z,t) + f(\hat{T})(x,z,t)) + L(y - C\hat{T}). \quad (69)$$

where $\hat{T} \in \mathbb{R}^{2n^2 \times 1}$ is the estimated state vector, and L is an observer gain matrix. Then, the observer error dynamic equation is given by:

$$\dot{\tilde{T}} = (A - LC)\tilde{T} + f(T) - f(\hat{T}), \quad (70)$$

where $\tilde{T} = T - \hat{T}$ is the state estimation error. Considering Proposition 2, the following provides sufficient conditions for exponential stability of the state observer error of equation (70).

It can be shown that if X and Y are real vectors of the same dimension, then the following inequality holds:

$$XY \leq \frac{X^2}{4} + Y^2. \quad (71)$$

Define $A_0 = A(u) - LC$, which is valid since A(u) is constant for the observer use, and a Lyapunov function as:

$$V = \tilde{T}^T P \tilde{T}, \quad (72)$$

for the stability, and its derivative as:

$$\dot{V} = -\tilde{T}^T [A_0^T P + P A_0] \tilde{T} + 2\tilde{T}^T P [f(T) - f(\hat{T})], \quad (73)$$

where $P \in \mathbb{R}^{2n^2 \times 2n^2}$ is any arbitrary symmetric positive definite matrix. Then, the following is valid since f(T) is Lipshitz.

$$2\tilde{T}^T P[f(T) - f(\hat{T})] \leq 2|P\tilde{T}|\gamma|\tilde{T}|. \quad (74)$$

Using the inequality of equation (71), define:

$$\begin{cases} X = 2\gamma |P\tilde{T}| \\ Y = \tilde{T} \end{cases}. \quad (75)$$

Then, $$2\gamma |P\tilde{T}||\tilde{T}| \leq \gamma^2 \tilde{T}^T PP\tilde{T}^T + \tilde{T}^T \tilde{T}, \quad (76)$$

$$\dot{V} \leq \tilde{T}^T [A_0^T P + PA_0 + \gamma^2 PP + I]\tilde{T}. \quad (77)$$

Note that if $[A_0^T P_1 + P_1 A_0 + \gamma^2 PP + I]$ is negative definite, then there exists a $P_2$ such that:

$$[A_0^T P_2 + P_2 A_0 + \gamma^2 P_2 P_2 + I] < 0. \quad (78)$$

Let:

$$[A_0^T P + PA_0 + \gamma^2 PP + I] = -\varepsilon I. \quad (79)$$

Then:

$$\dot{V} \leq -\varepsilon \tilde{T}^T \tilde{T} < 0 \text{ so } \tilde{T} \to 0 \text{ exponentially}, \quad (80)$$

$$(A(u) - LC)P + P(A(u) - LC)^T + \gamma^2 PP + I(\varepsilon + 1) = 0 \quad (81)$$

By setting the terms as described in Proposition 2, a standard algebraic Ricatti equation is obtained that has a solution if P is a symmetric and positive definite matrix.

Figure 18A:
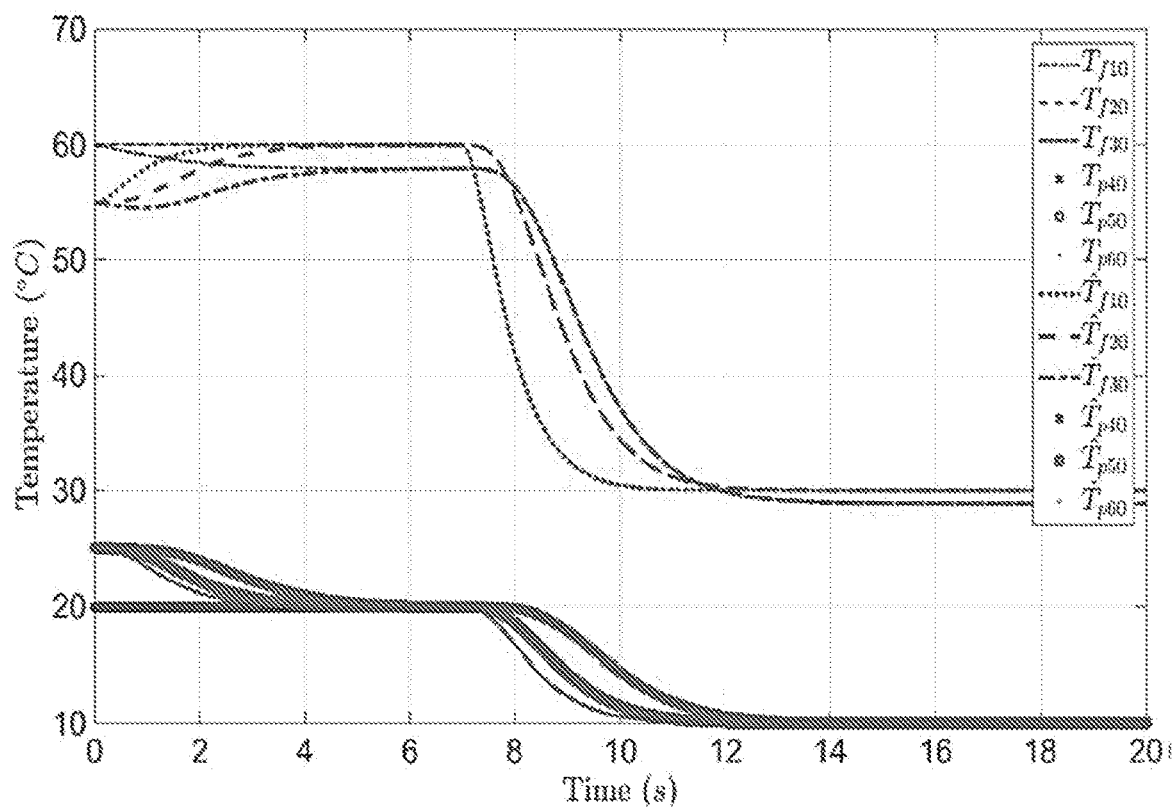
FIGS. 18A and 18B illustrate the convergence and error of the feed and permeate states with PESC in accordance with various embodiments of the present disclosure.
Figure 18B:
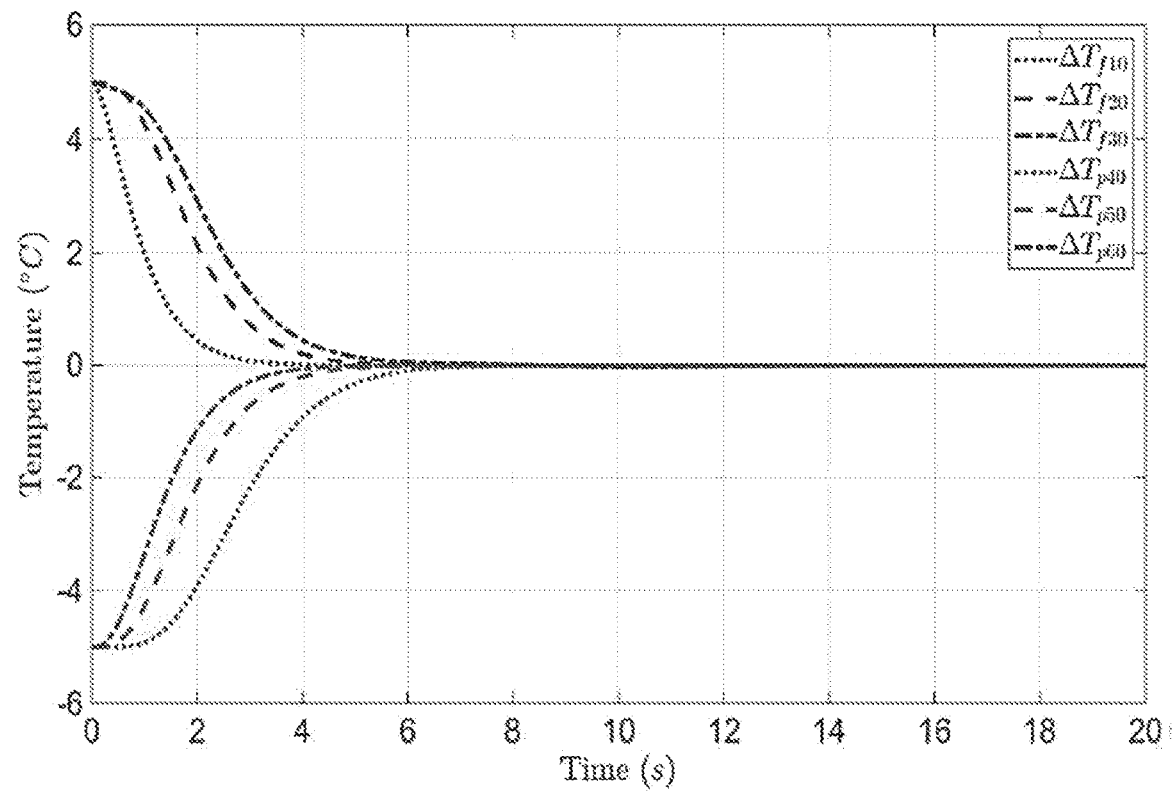

FIG. 18A shows the fast convergence of the estimated feed ($T_f$) and permeate ($T_p$) states using the nonlinear Lyapunov-based observer for different locations in the MD discretization grid. FIG. 18A also shows how the nonlinear observer is robust to any sudden changes in the process. The fast convergence of the observer is guaranteed by taking smaller sampling time. In the same context, the error analysis depicted in FIG. 18B illustrates the exponential convergence of the error ($\Delta T$) to zero.

Observer Based PESC Structure.

Following the design of the nonlinear Lyapunov-based observer, the temperature distribution all along the designated process domain can be available at each instant of time. Proceeding further, these estimates can be provided to the PESC to optimize the performance function in equation (55), without the need to directly access the inaccessible process states. This is valid, when the observer convergence is fast.

Figures 19, 20:
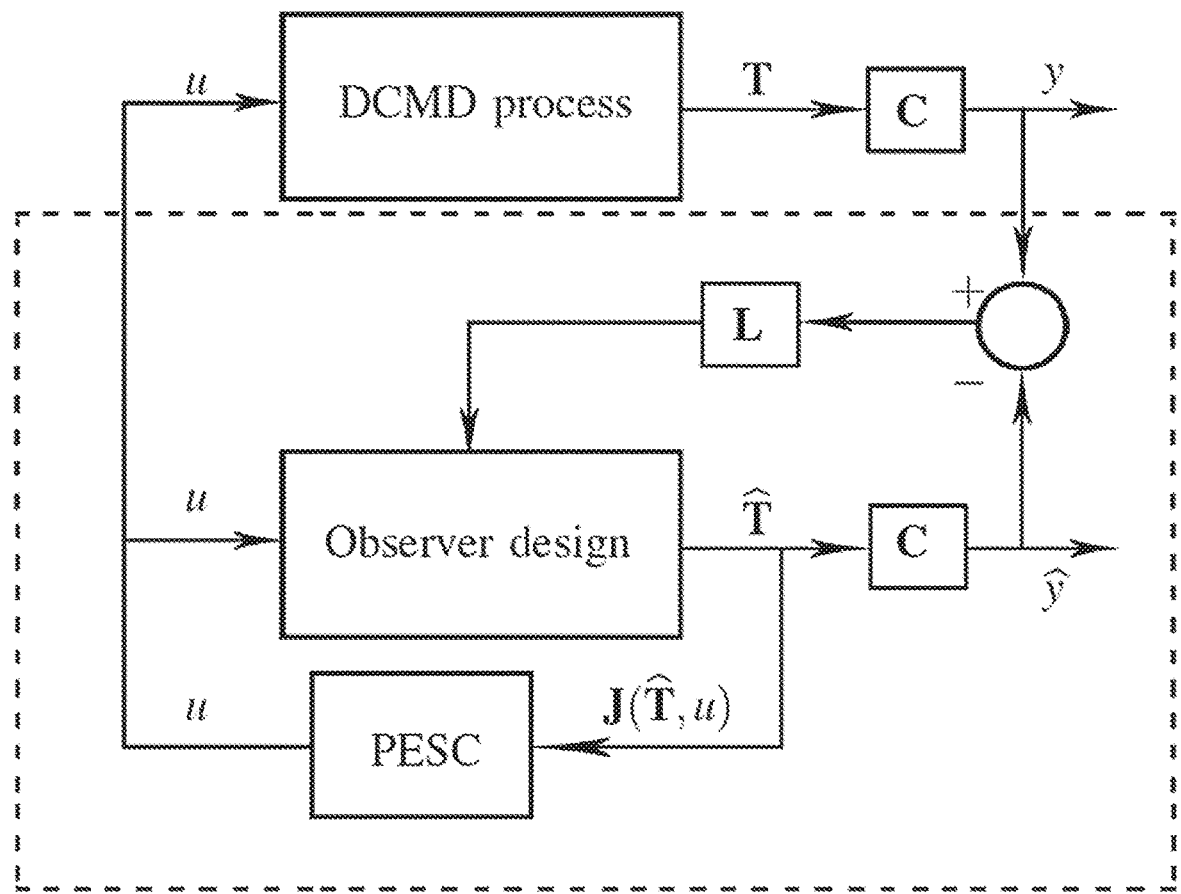
FIG. 19 is a block diagram illustrating an example of the structure of a PESC controller in accordance with various embodiments of the present disclosure.
FIG. 20 includes a table indicating characteristics of the membrane used in simulations of the PESC in accordance with various embodiments of the present disclosure.

Considering the single parameter PESC, the structure of the performance function would be given by:

$$J(\hat{T}, u) = -|\mathcal{J}(\hat{T})| + \frac{1}{2}\Gamma|\rho u|, \quad (82)$$

and the PESC structure would depend only on the estimate of the temperature distribution (T). FIG. 19 illustrates an example of the structure of the observer based single parameter PESC.

Simulation and Results

Analysis for the observer based PESC scheme will now be discussed through numerical simulations using the MD process dynamic model in equation (54) for each input case. The PESC scheme was equipped with anti-windup technique to prevent input saturation. All fabrication parameters of the employed membrane were realistic, and are listed in the table of FIG. 20. For the single parameter case, we consider the feed pump flow rate ($u=u_f$) as the only control input, while keeping the permeate pump flow rate constant at $u_p$=0.2 (m/s). From a practical perspective, $u_f$ should be bounded with minimum and maximum values to reflect the pump's physical limitations and energy management, as given by 0.1 (m/s)≤$u_f$≤0.4 (m/s).

Figure 21A:
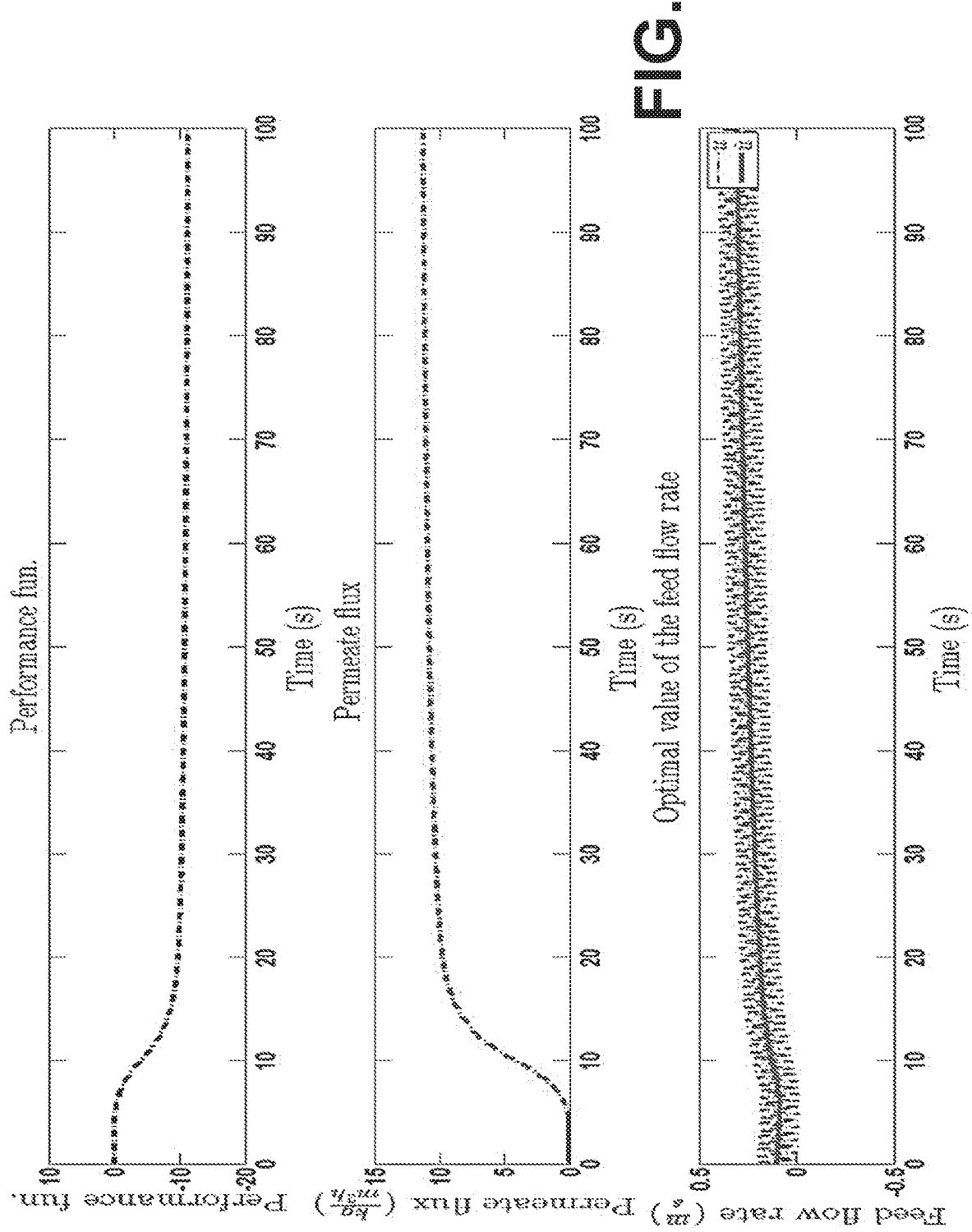
FIGS. 21A through 21C illustrates simulation results of PESC implementations in accordance with various embodiments of the present disclosure.

The simulation results of the single parameter PESC with anti-windup technique is depicted in FIG. 21A, where it illustrates the time evolution of the performance function, the permeate flux and the optimized feed pump flow rate ($u_f$). It can be seen that the permeate flux reaches its maximum value (about 12 kg/m²·h), and the control input oscillates in a small neighborhood around the optimal value, which is less than its maximum bound.

Figure 21B:
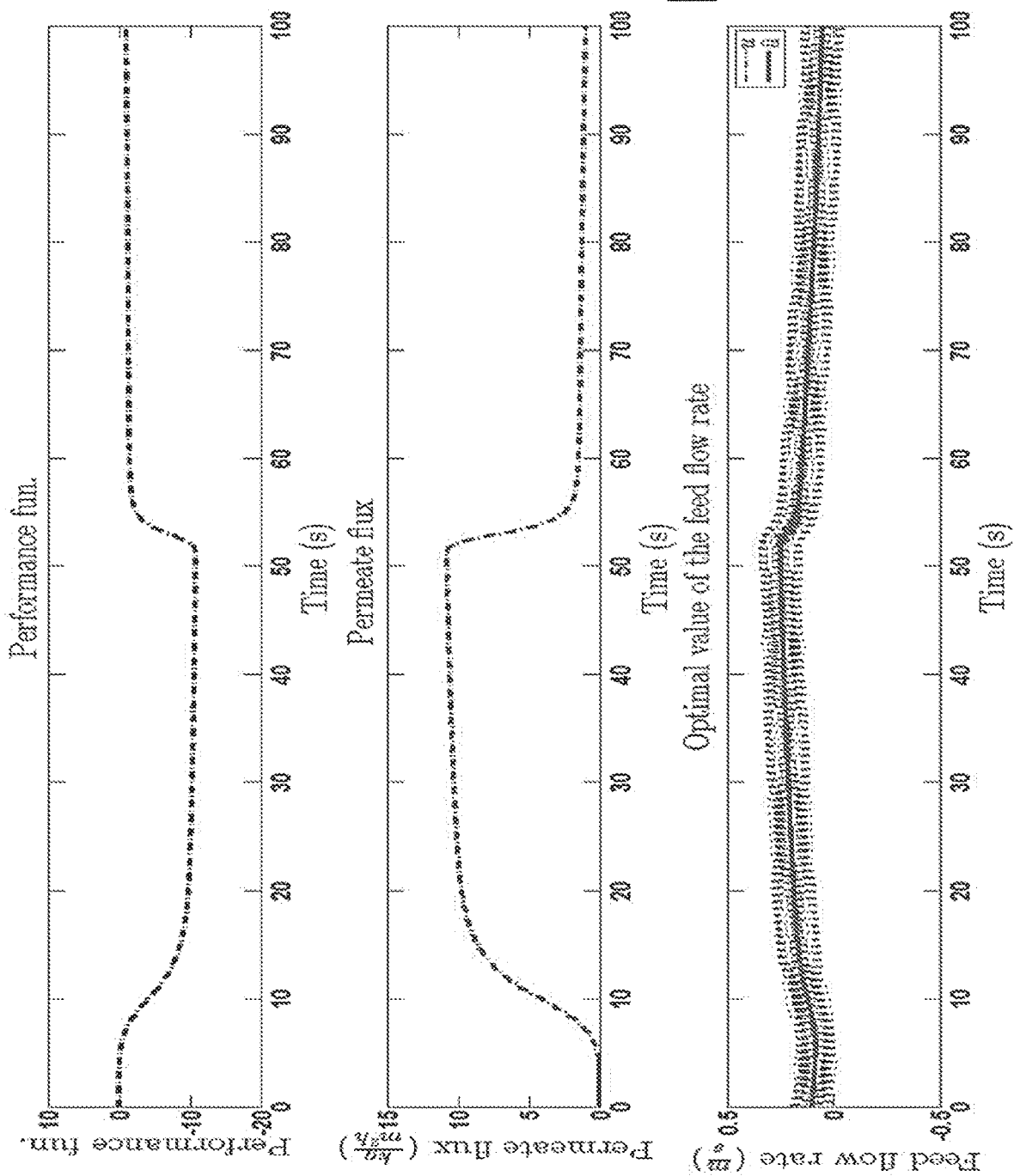

Referring next to FIG. 21B, shown are the simulation results when a sudden disturbance is introduced to the MD process to assess the sensitivity as well as the adaptability of the PESC scheme. The disturbance happens at the middle of the simulation by lowering the feed inlet temperature from 60° C. to 30° C. at t=50 s. FIG. 21B shows the response of the control input to the disturbance. Note that the generated permeate flux is more significant at high temperature, and this may explain the low generation of permeate flux at 30° C.

Figure 21C:
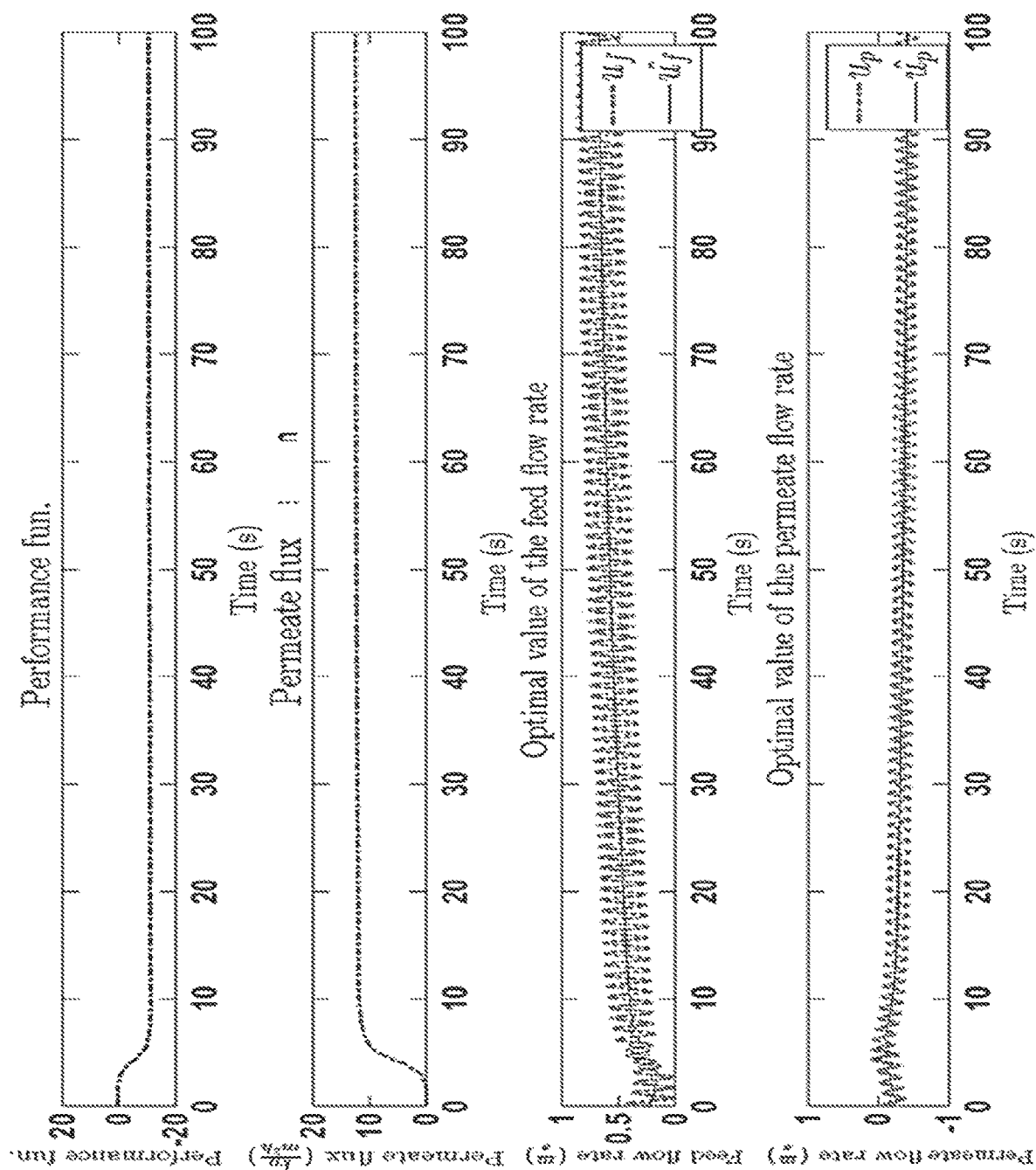

For the multiple-parameter case, the performance function was optimized considering the feed and the permeate pumps flow rates as control inputs, where u=$[u_f, u_p]^T$. FIG. 21C demonstrates the time evolution of the performance function, the permeate flux and the optimized feed and permeate control inputs, FIG. 21C also shows the rapid convergence of the permeate flux to its maximum value, and the saturation of the control inputs. It can be seen from the simulations results, that the permeate flux in the multiple-parameter case reaches a similar level as the single parameter case (around about 12 kg/m²·h), but with higher pump flow rates. This may be attributed to the additional degrees of freedom that are provided to the process, by assigning a second control input, where the newly added design parameters can be elaborately tuned, and therefore, contribute toward fast convergence for the performance function.

An observer based PESC for a MD process has been examined. The process can be modeled with a dynamic 2D ADE model. It is possible for the controller to maximize the permeate vapor flux while at the same time to minimize the consumed energy via the feed and permeate pumps flow rates. For this, a nonlinear Lyapunov-based observer was used to provide an estimate for the temperature distribution among the domain of the MD process and feed the estimates to the PESC. Two sets of control inputs were considered for the PESC scheme: single control input of the feed pump flow rate, and multiple control inputs of both feed and permeate pumps flow rates. They were provided with an anti-windup technique to prevent actual input saturation. Simulations show the time evolution of the control inputs and support the feasibility of their energy consumption.

Multivariable Esc of Solar Powered MD Process

A real time multivariable optimal controller is disclosed for a solar powered direct contact membrane distillation (DCMD) process using Newton-based extremum seeking control (ESC). This controller takes into account the varying feed inlet temperature, due to the dynamic nature of the sun. Moreover, since ESC is non-model based, the controller design is robust against plant-model mismatch. For this work, a multivariable Newton-based ESC is described for the optimization of a solar powered MD water desalination plant. The dynamic model of the heat and mass transfer in the MD process along with the solar powered MD optimal control problem formulation will be presented.

Figure 22:
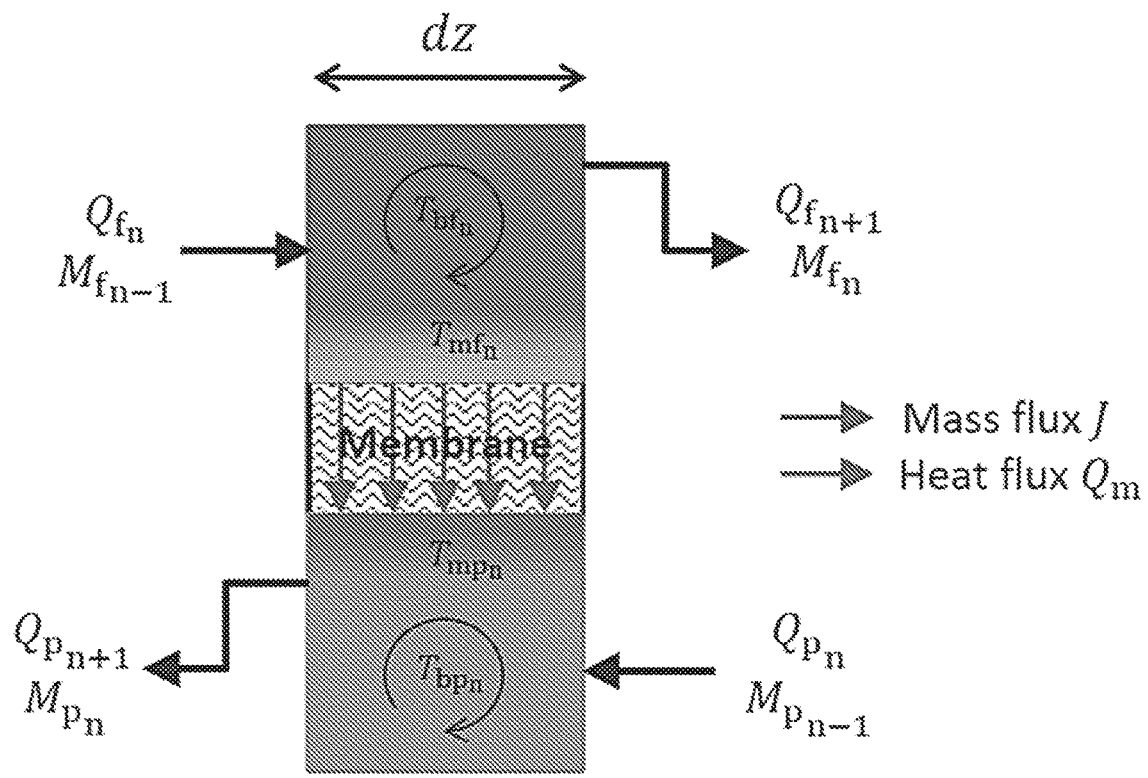
FIG. 22 is a schematic diagram illustrating an example of a MD cell in accordance with various embodiments of the present disclosure.

First consider the MD module illustrated in FIG. 22. In this configuration, hot water passes along the hydrophobic membrane on one side, which is called the feed side, and cold water flows in the counter direction along the other side, which is called the permeate side. Water vapor is driven from the feed side across the membrane and into the permeate side by the induced vapor pressure difference. Both heat and mass transfer processes occur simultaneously as water evaporates at the feed-membrane interface and condenses at the permeate-membrane interface. As a result, the temperature at the membrane boundary layers differs from the bulk temperature of the feed and permeate streams. The MD module can be divided into N control volume cells, where individual cells can have a uniform bulk temperatures ($T_{bf_n}$, $T_{bp_n}$) except at the boundary layers where the temperatures are ($T_{mf_n}$, $T_{mp_n}$), as shown in FIG. 22 for the $n^{th}$ cell.

Mass Transfer in DCMD.

The transport phenomena is described by the classic gas permeation and heat transfer theories. The mass flux (J) in DCMD is related to the saturated vapor pressure difference across the membrane (ΔP) through the membrane mass transfer coefficient ($B_m$) as follows $$J = B_m \Delta P = B_m(P_{mf} - P_{mp}). \tag{83}$$

The saturated vapor pressure of pure water ($P_w^{sat}[T]$) as a function of temperature is given by the Antoine equation:

$$P_w^{sat}[T] = \exp\left(23.1964 - \frac{3816.44}{T + 227.02}\right). \tag{84}$$

Dissolved salt in the feed stream reduces the saturated vapor pressure, therefore to compensate for this the following relation was proposed in:

$$P_{mf} = (1 - x_{NaCl})(1 - 0.5 x_{NaCl} - 10 x_{NaCl}^2) P_w^{sat}[T_{mf}], \tag{85}$$

where $x_{NaCl}$ is the mole fraction of NaCl in the feed stream. However, permeate and the saturated vapor at the membrane-permeate interface is pure water. Thus, $P_{mp} = P_w^{sat}[T_{mp}]$.

Heat Transfer in DCMD.

Figure 23:
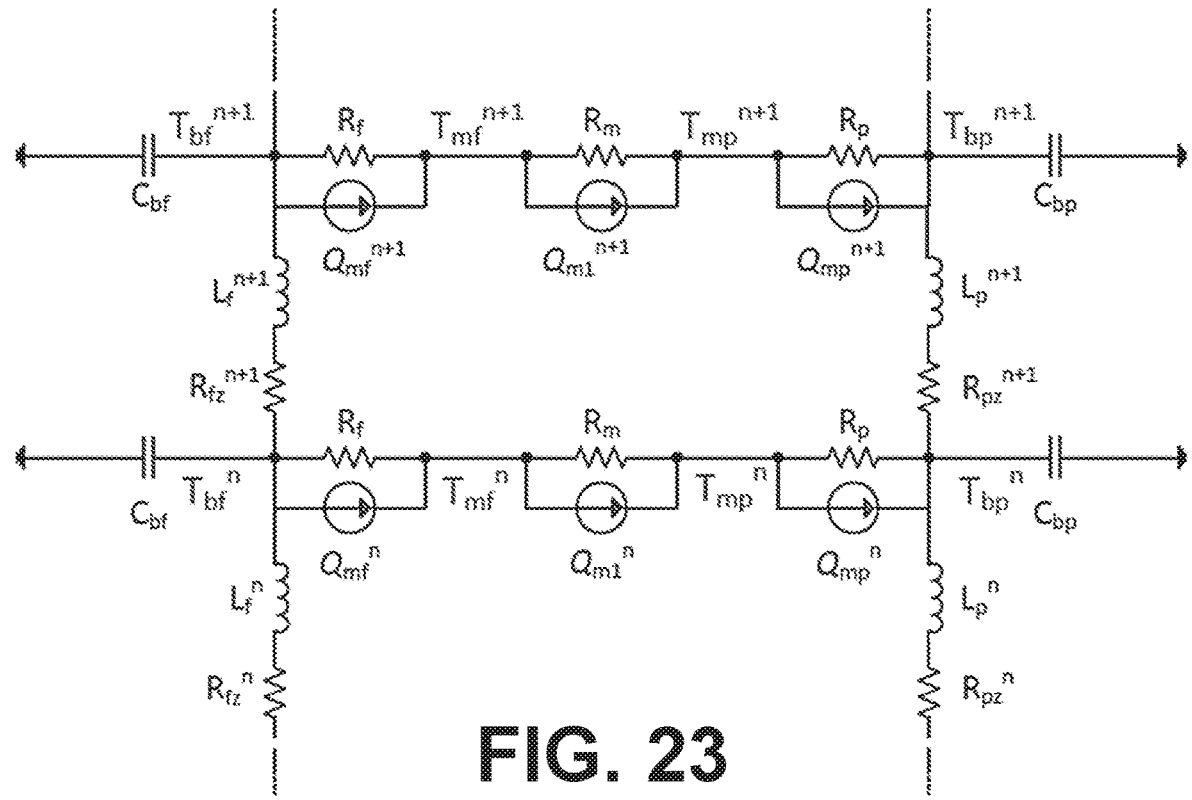
FIG. 23 is a schematic diagram illustrating an electrical analog circuit for a MD module including the MD cells of FIG. 22 in accordance with various embodiments of the present disclosure.

Heat transfer in DCMD is a spatially and temporally distributed phenomena. A dynamical model, based on an electrical analogy to thermal systems, can be used for both transient and steady-state response. The resulting model can be a system of differential-algebraic equations (DAE) or a descriptor system. The schematic diagram for the electrical analog circuit for the DCMD module is shown in FIG. 23. By applying Kirchoff's electrical laws (KCL and KVL) to the analog circuit for the DCMD, the following equations can be obtained. On the feed side, the rate of change of the heat transfer rate from the n−1 cell to the $n^{th}$ cell is proportional to the temperature difference between them. Taking into consideration the series impedance $Z_n^f$, this can be expressed as:

$$\frac{dQ_{f_n}}{dt} = \frac{1}{L_f^n} T_{bf_{n-1}} - \frac{R_{fz}^n}{L_f^n} Q_{f_n} - \frac{1}{L_f^n} T_{bf_n}. \tag{86}$$

Using Kirchoff's current law at the $n^{th}$ feed node, it follows that the rate of change for the bulk feed temperature ($T_{bf_n}$) is:

$$\frac{dT_{bf_n}}{dt} = \frac{1}{C_{bf}} Q_{f_n} - \frac{1}{C_{bf}} \left( \frac{1}{R_f} + J_n A_m c_p \right) T_{bf_n} - \frac{1}{C_{bf}} Q_{f_{n+1}} + \frac{1}{C_{bf} R_f} T_{mf_n}. \quad (87)$$

Equation (86) describes the dynamics of the heat transfer rates into and out of the $n^{th}$ feed cell ($Q_{f_n}$ and $Q_{f_{n+1}}$, respectively).

On the permeate side, the rate of change of the heat transfer rate ($Q_{p_n}$) is:

$$\frac{dQ_{p_n}}{dt} = \frac{1}{L_p^n} T_{bp_{n-1}} - \frac{R_{pz}^n}{L_p^n} Q_{p_n} - \frac{1}{L_p^n} T_{bp_n}, \quad (87)$$

And the dynamics of the bulk permeate temperature ($T_{bp_n}$) is?

$$\frac{dT_{bp_n}}{dt} = \frac{1}{C_{bp}} Q_{p_n} - \frac{1}{C_{bp} R_p} T_{bp_n} - \frac{1}{C_{bp}} Q_{p_{n+1}} + \frac{1}{C_{bp}} \left( \frac{1}{R_p} + J_n A_m c_p \right) T_{mp_n}. \quad (88)$$

The coupling between the feed and the permeate dynamics in the $n^{th}$ cell can be written in residue form as:

$$0 = \left( \frac{1}{R_f} + J_n A_m c_p \right) T_{bf_n} - \frac{1}{R_f} T_{mf_n} - \left( \frac{1}{R_p} + J_n A_m c_p \right) T_{mp_n} + \frac{1}{R_p} T_{bp_n}, \quad (89)$$

$$0 = \left( \frac{1}{R_m} + \frac{1}{R_p} + J_n A_m c_p \right) T_{mp_n} - \frac{1}{R_p} T_{bp_n} - J_n A_m H_v [T_{mf_n}] - \frac{1}{R_m} T_{mf_n}. \quad (90)$$

The outlet temperatures at the terminal cells of the feed and permeate analog are also given by the algebraic equations, where are respectively:

$$0 = T_{f_{out}} - T_{p_{in}} - R_{f_{term}} Q_{f_{n+1}}, \quad (91)$$

$$0 = T_{p_{out}} - T_{f_{in}} + R_{p_{term}} Q_{p_1}. \quad (92)$$

The heat and mass transfer equations (86)-(92) represent a nonlinear differential-algebraic system. When considering N number of interconnected cells, the resultant equations can be expressed as a nonlinear descriptor system of the form:

$$E\dot{X}(t) = F(X(t), u(t)) \quad (93)$$

$$J = g(x) \quad (94)$$

where $X \in \mathbb{R}^{6N+4}$ represents the differential and algebraic states $\dot{X}$ refers to the time derivative of the state vector, $E \in \mathbb{R}^{6N+4 \times 6N+4}$ is a singular matrix, $F(X(t), u(t))$ is a nonlinear function of the states and input, $u(t) = [M_{f_{in}}, M_{p_{in}}]$ represents the inlet feed and permeate mass flow rates respectively, the distilled water flux J is also given by a nonlinear function of the state $g(X)$. With the dynamical model of DCMD described, next consider the complete setup of the solar powered DCMD water desalination system.

Figure 24:
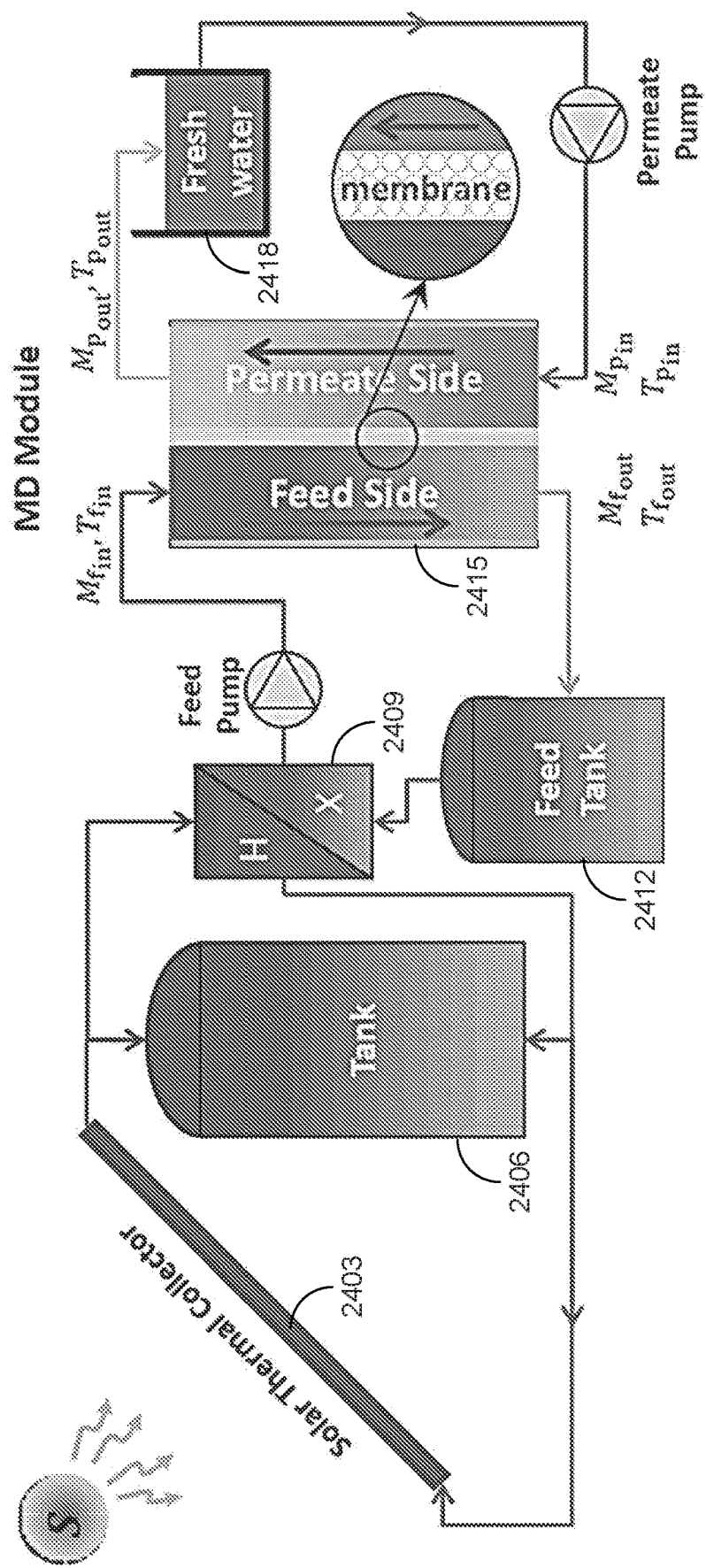
FIG. 24 is a schematic diagram illustrating an example of a solar powered MD process in accordance with various embodiments of the present disclosure.

Optimal control problem of solar powered DCMD. Referring to FIG. 24, shown is an example of a solar powered MD process. The solar powered DCMD water desalination setup comprises a solar thermal collector 2403 connected a storage tank 2406 and a heat exchanger 2409. The feed water is circulated from a feed tank 2412 through the heat exchanger 2409 to the DCMD module 2415 and back to the feed tank 2412. The permeate is pumped from a fresh water tank 2418 into the DCMD module 2415, where it collects the distilled water flux and flows back into the fresh water tank 2418. The control inputs are the mass flow rates of feed and permeate sides. The feed inlet temperature ($T_{f_{in}}$) will vary according to the solar radiation throughout the day, which affects the distilled water flux. An optimal control strategy can be used to ensure the efficiency of the process under disturbed operating conditions. One way to optimize the process is by maximizing the following objective function Y, which minimizes the feed/permeate inlet mass flow rates and maximizes the distilled water flux (J):

$$\max \mathcal{Y} = \max(\alpha_1 J - (\alpha_2 M_{f_{in}} + \alpha_3 M_{p_{in}})). \quad (95)$$

Figure 25A:
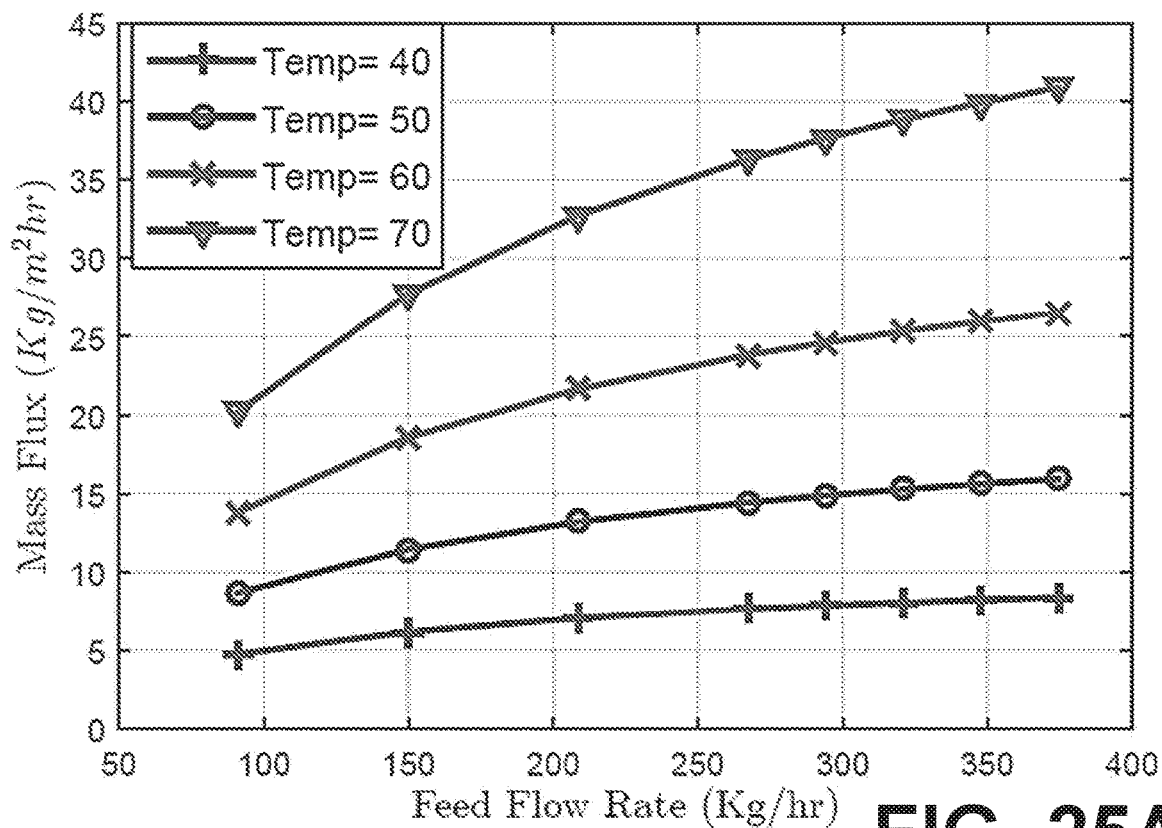
FIGS. 25A and 25B illustrate simulation results for the MD process of FIG. 24 in accordance with various embodiments of the present disclosure.
Figure 25B:
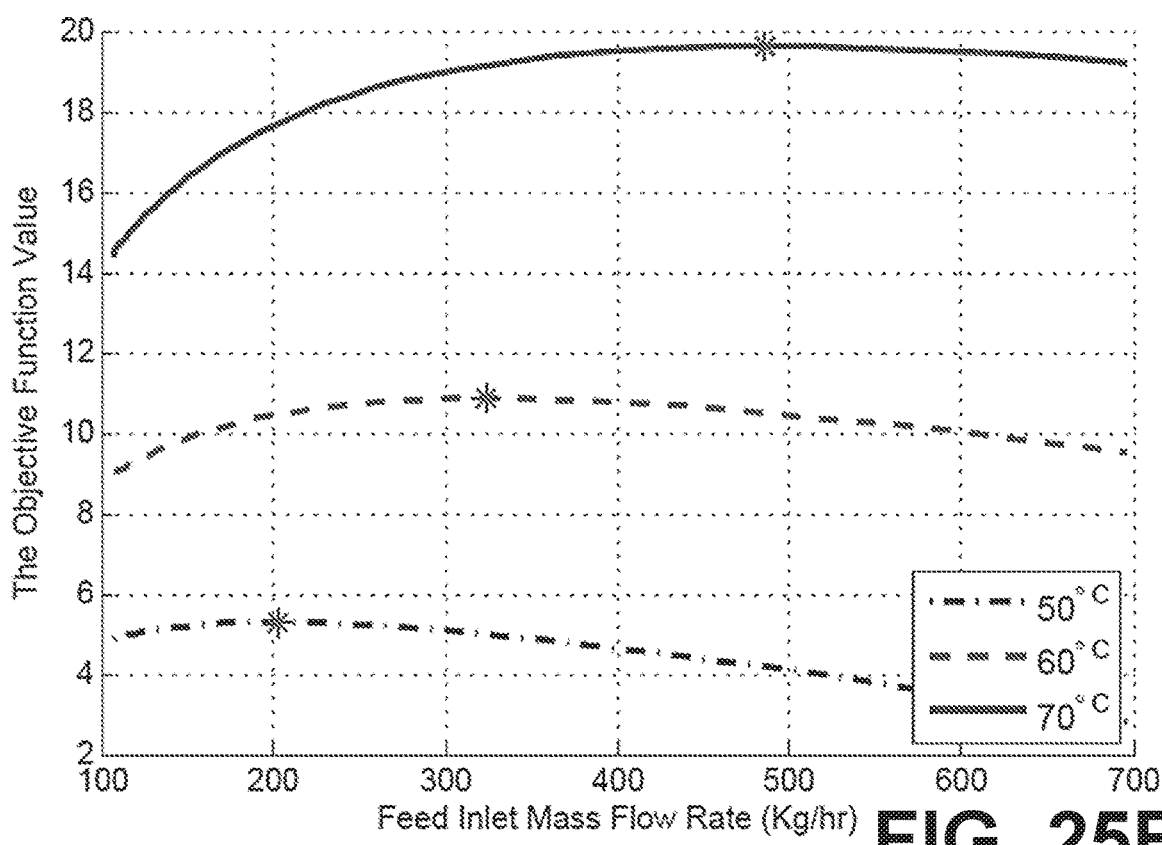

FIG. 25A shows the response of the DCMD process under various feed inlet temperatures and feed inlet mass flow rates. In this simulation, the permeate inlet mass flow rate was kept constant at 256 Kg/hr, while the feed inlet mass flow rate was increased from 90 Kg/hr to 375 Kg/hr. This was repeated for 5 feed inlet temperatures. As demonstrated in FIG. 25A, increasing the feed inlet temperature increased the distilled water flux. While increasing the feed inlet mass flow rate increases the flux, the flux reached saturation values at high feed inlet mass flow rates. As shown in FIG. 25B, the objective function of equation (95) has a maximum that varies for different feed inlet temperature. Similar characteristics are exhibited for the objective function with respect to the inlet permeate mass flow rate. Therefore, the controller can automatically track the peak of the objective function by manipulating the inlet feed and permeate mass flow rates.

Multivariable ESC for Real Time Optimization

Extremum seeking is a real time optimization method, which is particularly useful to keep the reference-to-output map at its extremum (maximum or minimum). This extremum might shift with the process parameters or under disturbance influence and it's the job of the ESC to track the extremum as it shifts. Newton-based multivariable ESC can rely on sinusoidal perturbation signals to estimate the gradient and the Hessian of the objective function by using low and high pass filters. It has been shown that the objective function has a ($T_{f_{in}}$) dependent peak, therefore it can be assumed that there exists $u^* = [M_{f_{in}}^*, M_{p_{in}}^*]^T$ such that:

$$\nabla y(u^*) = 0 \quad (96)$$

$$\frac{\partial^2 y(u^*)}{\partial u^2} = H < 0, \quad (97)$$

where $H = H^T$.

Figures 26, 27:
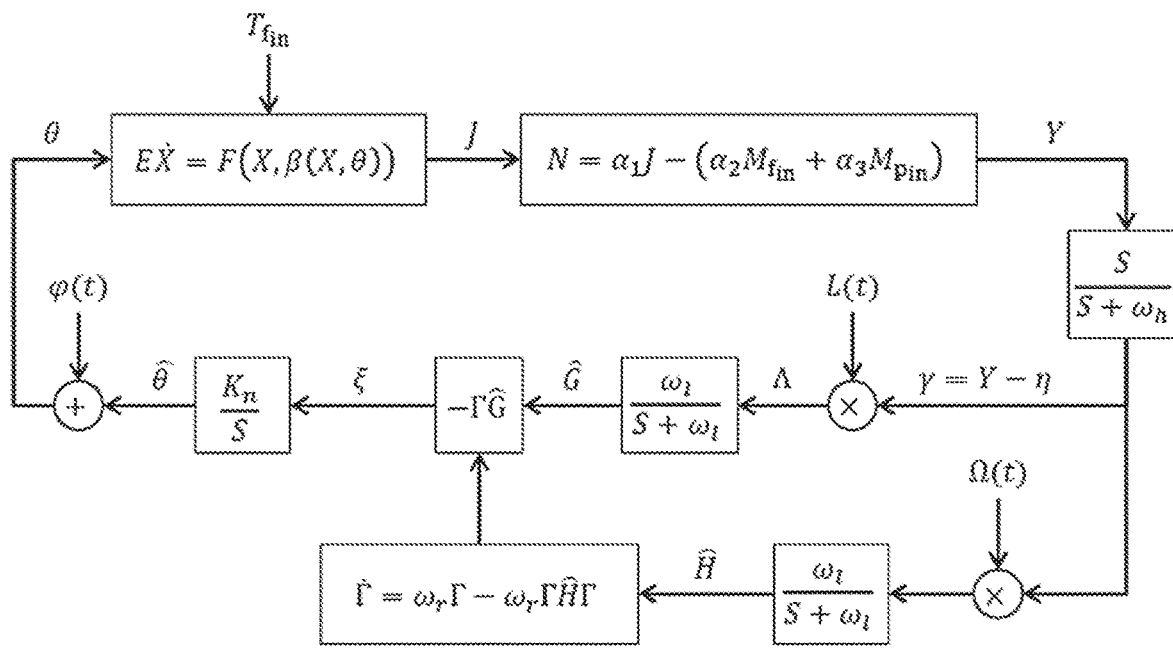
FIG. 26 is a schematic diagram illustrating an example of Newton-based multivariable ESC in accordance with various embodiments of the present disclosure.
FIG. 27 is a table indicating characteristics of a MD module used in the simulation of the MD process of FIG. 24 in accordance with various embodiments of the present disclosure.

Suppose that the control input is given by $u = \beta(X, \theta)$, which is a smooth function of the states and the parameters $\theta = [\theta_1, \theta_2]^T$. Then, the closed loop system is given by $E\dot{X} = F(X, \beta(X, \theta))$. The objective of the ESC is to maximize the value of Y. The block diagram of the Newton-based ESC is shown in FIG. 26, where $K_n$ is a positive diagonal matrix, and the perturbation matrices ($L(t) \in \mathbb{R}^{2 \times 1}$, $\Omega(t) \in \mathbb{R}^{2 \times 2}$, and $\phi(t) \in \mathbb{R}^{2 \times 1}$) are defined as:

$$L(t) = \left[\frac{2}{c_1}\sin(\omega_1 t), \frac{2}{c_2}\sin(\omega_2 t)\right]^T, \quad (98)$$

$$\Omega(t) = \Omega^T(t), \quad (99)$$

$$\Omega_{i,i} = \frac{16}{c_i^2}\left(\sin^2(\omega_i t) - \frac{1}{2}\right), \quad (100)$$

$$\Omega_{i,k} = \frac{4}{c_i c_k}(\sin(\omega_i t)\ \sin(\omega_k t)),\ i \neq k, \quad (101)$$

$$\varphi(t) = [c_1\sin(\omega_1 t), c_2\sin(\omega_2 t)]^T, \quad (102)$$

where $\omega_i \neq \omega_k$ and such that $\omega_i/\omega_k$ is a rational number, and $c_1$, $c_2$ are real positive numbers. The cut-off frequencies for the low and high pass filters, $\omega_l$ and $\omega_h$ respectively, can be designed appropriately according to:

$$w_l \ll \min\{\omega_i, |\omega_i - \omega_k|, |2\omega_i - \omega_k|\}, \quad (103)$$

$$\omega_h > \omega_i, \forall i,k | i \neq k. \quad (104)$$

This design derives an estimate of the gradient vector $\hat{G}$ a and the Hessian by adding the perturbation signal $\varphi(t)$ to the estimated optimal input $\hat{\theta}$. The estimate of the Hessian matrix is inverted by the dynamical system given by:

$$\dot{\Gamma} = \omega_r \Gamma - \omega_r \Gamma \hat{H}\Gamma, \quad (105)$$

where $\Gamma = \hat{H}^{-1}$, to avoid difficulties of algebraically inverting $\hat{H}$ when it is close to singular. To summarize the dynamical system shown in FIG. 26, the following equations are presented:

$$E\dot{X} = F(X, \beta(X, \theta)),$$

$$\dot{\eta} = -\omega_h \eta + \omega_h \gamma,$$

$$\dot{\hat{G}} = -\omega_l \hat{G} + \omega_l \Lambda,$$

$$\dot{\hat{\theta}} = K_n \xi,$$

$$\dot{\hat{H}} = \omega_l \hat{H} + \omega_l \Omega(t)(\gamma - \eta),$$

$$\dot{\Gamma} = \omega_r \Gamma - \omega_r \Gamma \hat{H}\Gamma,$$

where $$\begin{bmatrix}\xi_1 \\ \xi_2\end{bmatrix} = -\begin{bmatrix}\Gamma_{11} & \Gamma_{12} \\ \Gamma_{21} & \Gamma_{22}\end{bmatrix}\begin{bmatrix}\hat{G}_1 \\ \hat{G}_2\end{bmatrix}, \text{ and } \begin{bmatrix}\Lambda_1 \\ \Lambda_2\end{bmatrix} = \begin{bmatrix}L_1(t) \\ L_2(t)\end{bmatrix}(y - \eta).$$

Simulation and Results

Simulations were carried out in order to demonstrate the effectiveness of the ES controller to optimize the solar powered DCMD water desalination process. For this purpose, realistic membrane parameters were used as listed in the table of FIG. 27. The design parameters for the Newton-based ESC were: $c_1 = c_2 = 0.15$, $\omega_1 = 3$ rad/s, $\omega_2 = 2$ rad/s, $\omega_l = 0.1$ rad/s, $\omega_h = 4$ rad/s, $K_n = \text{diag}([0.05, 0.05])$, $\omega_r = 0.0008$.

Figure 28A:
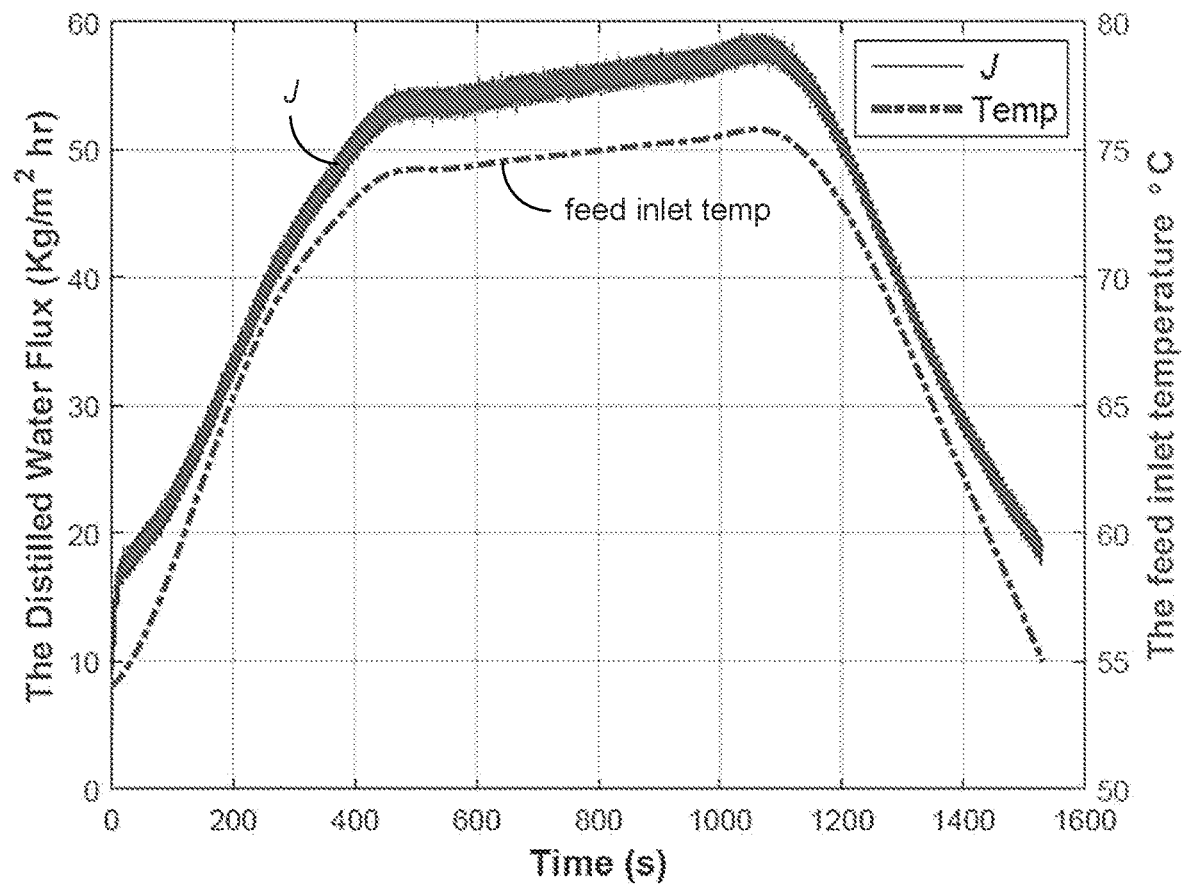
FIGS. 28A and 28B are simulation results for the Newton-based multivariable ESC in accordance with various embodiments of the present disclosure.
Figure 28B:
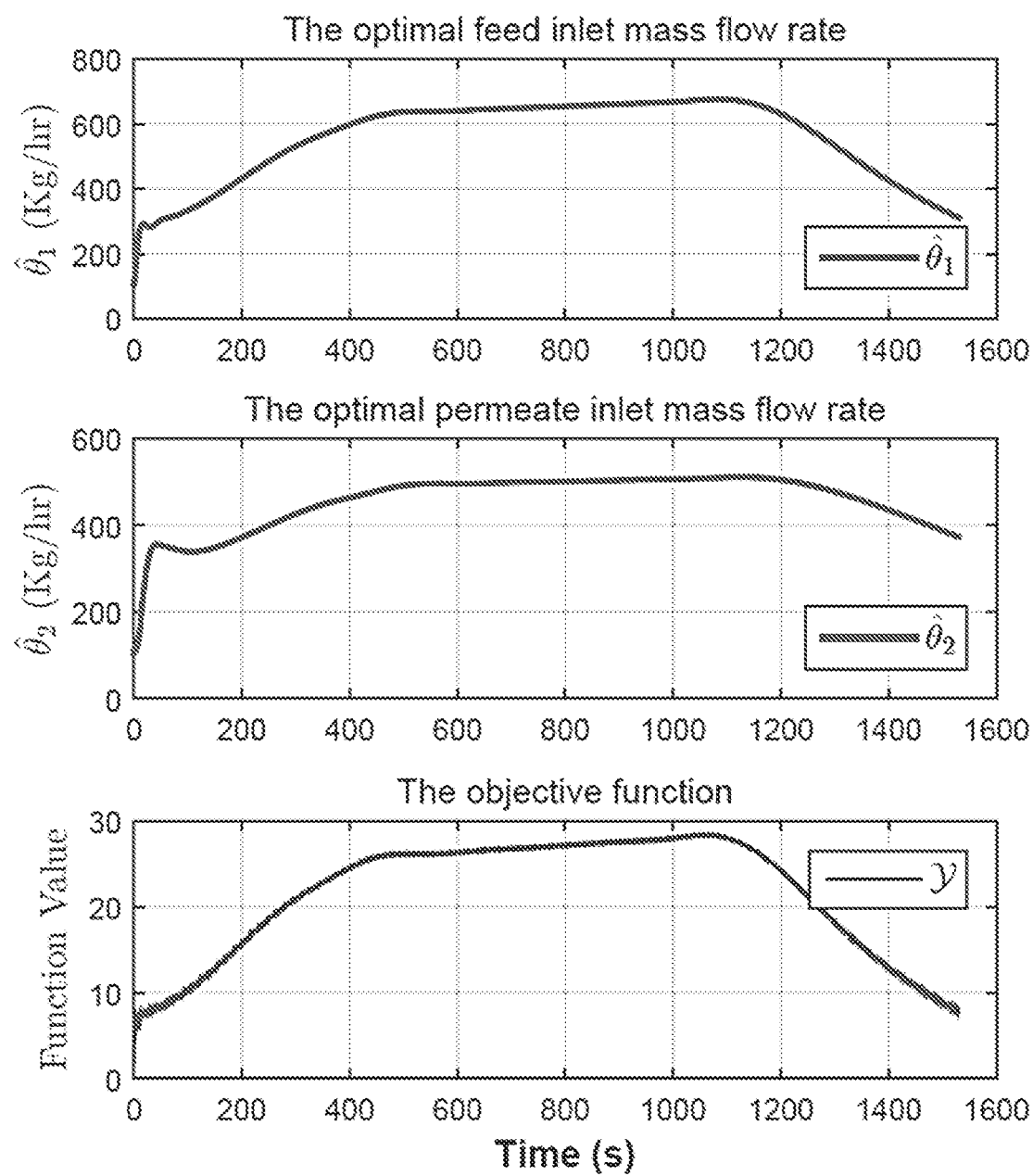

The feed inlet temperature profile depicted in FIG. 28A was designed to reflect a realistic behavior. The permeate inlet temperature was kept constant throughout the simulation at 20° C. As the feed inlet temperature increases, the distilled water flux (J) is optimized taking into account the feed and permeate inlet mass flow rates, as shown in FIG. 28A. FIG. 28B shows the estimated optimal inlet mass flow rages for the feed and permeate sides along the objective function value. The ESC dynamics takes about 50 seconds to converge to the optimal estimated input $\hat{\theta}$ as shown in FIG. 28B. After that, the controller tracks the peak of the objective function with smooth transitions as it varies with the feed inlet temperature. As the temperature drops, the ESC quickly adjusts the inputs.

The optimization of the solar powered DCMD water desalination process was presented. The optimization problem addressed maximizing the distilled water flux while minimizing the feed and permeate inlet mass flow rates, which are highly related to the energy being used to pump water. The multivariable Newton-based ES controller was used for real time optimization. A dynamic model of the process was used to carry out the simulation. The simulation results show that the ESC was able to track the peak of the objective function as it varied with the feed inlet temperature.

Figure 29:
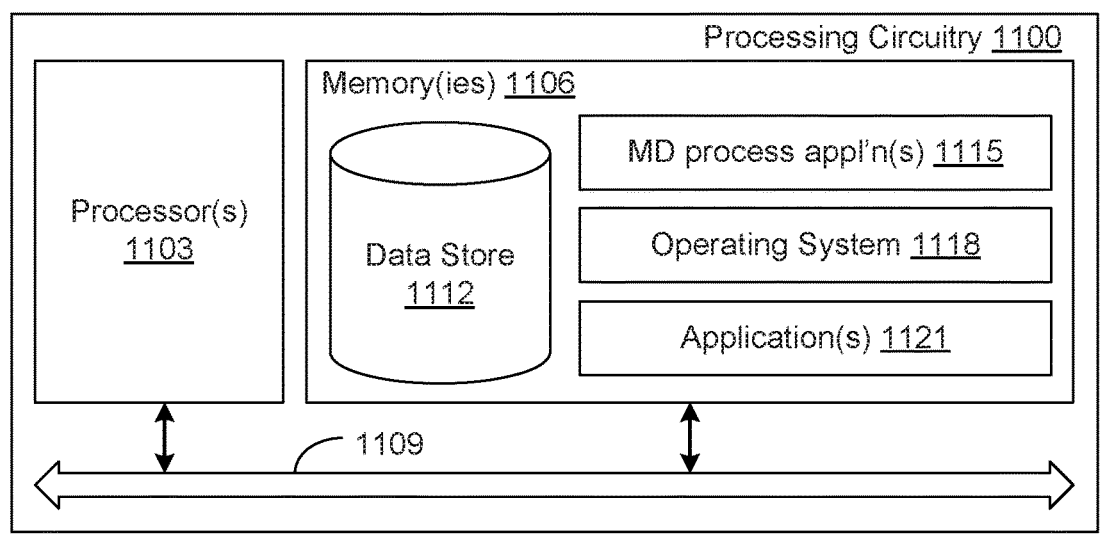
FIG. 29 is a schematic block diagram that illustrates an example of processing circuitry employed in the membrane distillation (MD) process of FIG. 1 in accordance with various embodiments of the present disclosure.

With reference now to FIG. 29, shown is a schematic block diagram of an example of processing circuitry 1100 that may be used to implement various portions of the control of the membrane distillation (MD) process 100 of FIG. 1 in accordance with various embodiments of the present disclosure. The processing circuitry 1100 includes at least one processor circuit, for example, having a processor 1103 and a memory 1106, both of which are coupled to a local interface 1109. To this end, the processing circuitry 1100 may be implemented using one or more circuits, one or more microprocessors, microcontrollers, application specific integrated circuits, dedicated hardware, digital signal processors, microcomputers, central processing units, field programmable gate arrays, programmable logic devices, state machines, or any combination thereof. The local interface 1109 may comprise, for example, a data bus with an accompanying address/control bus or other bus structure as can be appreciated. The processing circuitry 1100 can include a display for rendering of generated graphics such as, e.g., a user interface and an input interface such, e.g., a keypad or touch screen to allow for user input. In addition, the processing circuitry 1100 can include communication interfaces (not shown) that allow the processing circuitry 1100 to communicatively couple with other communication devices. The communication interfaces may include one or more wireless connection(s) such as, e.g., Bluetooth or other radio frequency (RF) connection and/or one or more wired connection(s).

Stored in the memory 1106 are both data and several components that are executable by the processor 1103. In particular, stored in the memory 1106 and executable by the processor 1103 are MD process application(s) 1115, an operating system 1118, and/or other applications 1121. MD process applications 1115 can include applications that support, e.g., controllers for control of the operation of the MD process 100 and/or observers for estimation of states of the MD process 100. It is understood that there may be other applications that are stored in the memory 1106 and are executable by the processor 1103 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, LabVIEW® or other programming languages.

A number of software components are stored in the memory 1106 and are executable by the processor 1103. In this respect, the term "executable" means a program file that is in a form that can ultimately be run by the processor 1103. Examples of executable programs may be, for example, a compiled program that can be translated into machine code in a format that can be loaded into a random access portion of the memory 1106 and run by the processor 1103, source code that may be expressed in proper format such as object code that is capable of being loaded into a random access portion of the memory 1106 and executed by the processor 1103, or source code that may be interpreted by another executable program to generate instructions in a random access portion of the memory 1106 to be executed by the processor 1103, etc. An executable program may be stored in any portion or component of the memory 1106 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1106 is defined herein as including both volatile and nonvolatile memory and data storage components. Volatile components are those that do not retain data values upon loss of power. Nonvolatile components are those that retain data upon a loss of power. Thus, the memory 1106 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1103 may represent multiple processors 1103 and the memory 1106 may represent multiple memories 1106 that operate in parallel processing circuits, respectively. In such a case, the local interface 1109 may be an appropriate network that facilitates communication between any two of the multiple processors 1103, between any processor 1103 and any of the memories 1106, or between any two of the memories 1106, etc. The local interface 1109 may comprise additional systems designed to coordinate this communication, including, for example, performing load balancing. The processor 1103 may be of electrical or of some other available construction.

Although the MD process application(s) 1115, the operating system 1118, application(s) 1121, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application described herein, including the MD process application(s) 1115 and/or application(s) 1121, that comprises software or code can be embodied in any non-transitory computer-readable medium for use by or in connection with an instruction execution system such as, for example, a processor 1103 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A system, comprising:
    a membrane distillation (MD) system comprising a feed side and a permeate side separated by a membrane, wherein each of the feed side and permeate side include a membrane boundary layer; and
    processing circuitry for maintaining a water production rate of the MD system,
    wherein the processing circuitry is configured (1) to use a model y to estimate temperature states at plural points along the membrane boundary layer in the feed side and along the membrane boundary layer in the permeate side, and (2) to apply a non-linear Lyapunov-based control to adjust one or more of an inlet temperature and inlet flow rate for the feed side and the permeate side, based at least on the estimated temperature states of the MD system, wherein the non-linear Lyapunov-based control includes a reference tracking error that is asymptotically stable, and wherein the reference tracking error is defined as a difference between an output of the model y and a reference $y_r$.

2. The system of claim 1, wherein the nonlinear Lyapunov-based boundary control is defined as a product of (i) a transpose of the reference tracking error and (ii) the reference tracking error.

3. The system of claim 1, wherein a temperature difference of the membrane boundary layers is controlled by a perturbation-based extremum seeking control (PESC).

4. The system of claim 1, wherein a temperature difference of the membrane boundary layers is controlled by a Newton-based multivariable extremum seeking control (ESC).

5. The system of claim 1, wherein the processing circuitry monitors inlet temperatures of the feed side and the permeate side to maintain the water production rate of the MD system.

6. The system of claim 5, wherein the inlet temperatures of the feed side and the permeate side are bounded by a defined minimum temperature and a defined maximum temperature.

7. The system of claim 1, wherein the processing circuitry monitors inlet flow rates of the feed side and the permeate side to maintain the water production rate of the MD system.

8. A method of controlling a production rate of a membrane distillation (MD) system, comprising:

determining a plurality of estimated temperature states of the MD system based on a model y, wherein the MD system comprises a feed side and a permeate side separated by a membrane, wherein each of the feed side and permeate side include a membrane boundary layer and the plurality of estimated temperature states correspond to plural points along the membrane boundary layer in the feed side and along the membrane boundary layer in the permeate side; and adjusting, with a non-linear Lyapunov-based control, an inlet flow rate or inlet temperature of at least one of the feed side or the permeate side based at least on the determined plurality of estimated temperature states, wherein the non-linear Lyapunov-based control includes a reference tracking error that is asymptotically stable, and wherein the reference tracking error is defined as a difference between an output of the model y and a reference $y_r$.

9. The method of claim 8, wherein the nonlinear Lyapunov-based boundary control is defined as a product of (i) a transpose of the reference tracking error and (ii) the reference tracking error.

10. The method of claim 8, wherein a temperature difference of the membrane boundary layers is controlled by a perturbation-based extremum seeking control (PESC).

11. The method of claim 8, wherein a temperature difference of the membrane boundary layers is controlled by a Newton-based multivariable extremum seeking control (ESC).

12. The method of claim 8, wherein a difference temperature along the membrane boundary layer is determined based upon temperature estimates generated by a non-linear observer.

13. The method of claim 8, further comprising:

adjusting a combination of inlet flow rate and inlet temperature of the feed side or the permeate side to control the water production rate of the MD system.

14. The system of claim 1, wherein a temperature difference between the membrane boundary layers is controlled about a defined reference temperature range.

15. The system of claim 1, wherein the model y uses a 2D advection diffusion equation to describe a heat transfer mechanism of the MD system.

16. The system of claim 15, wherein the 2D advection diffusion equation is applied to a semi-discretized model.

17. The system of claim 1, wherein the processing circuitry is configured to maintain the water production rate at a rate that is about constant.

\* \* \* \* \*